(12) United States Patent  
Alexander et al.

(10) Patent No.: US 11,768,137 B2  
(45) Date of Patent: Sep. 26, 2023

(54) SIZE-BASED SEPARATION OF DISSOCIATED FIXED TISSUES

(71) Applicant: VENTANA MEDICAL SYSTEMS, INC., Tucson, AZ (US)

(72) Inventors: Nelson Alexander, Marana, AZ (US); Aoune Barhoumi, Oro Valley, AZ (US); Lisa Gallegos, Tucson, AZ (US); Stacey Stanislaw, Tucson, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 806 days.

(21) Appl. No.: 16/571,785

(22) Filed: Sep. 16, 2019

(65) Prior Publication Data  
US 2020/0011775 A1 Jan. 9, 2020

Related U.S. Application Data

(63) Continuation of application No. PCT/EP2018/058809, filed on Apr. 6, 2018.  
(Continued)

(51) Int. Cl.  
*G01N 1/40* (2006.01)  
*B01L 3/00* (2006.01)  
*C12Q 1/6886* (2018.01)  
*G01N 1/28* (2006.01)  
*G01N 33/574* (2006.01)

(52) U.S. Cl.  
CPC ...... *G01N 1/4077* (2013.01); *B01L 3/502753* (2013.01); *B01L 3/502761* (2013.01); *C12Q 1/6886* (2013.01); *G01N 1/286* (2013.01); *G01N 33/57496* (2013.01); *B01L 2200/0652* (2013.01); *B01L 2300/0681* (2013.01); *B01L 2400/0403* (2013.01); *B01L 2400/086* (2013.01); *G01N 2001/2866* (2013.01); *G01N 2001/4088* (2013.01)

(58) Field of Classification Search  
None  
See application file for complete search history.

(56) References Cited

U.S. PATENT DOCUMENTS

2003/0059764 A1* 3/2003 Ravkin ............... B01J 19/0046  
435/7.21  
2007/0196820 A1 8/2007 Kapur et al.  
(Continued)

FOREIGN PATENT DOCUMENTS

CN 101305087 A 11/2008  
JP 2013042689 A 3/2013  
(Continued)

OTHER PUBLICATIONS

A Lee et al, "All-in-One Centrifugal Microfluidic Device for Size-Selective Circulating Tumor Cell Isolation with High Purity", Analytical Chemistry, vol. 86, No. 22, 2014, p. 11349-11356, XP055488124.  
(Continued)

*Primary Examiner* — Lore R Jarrett  
(74) *Attorney, Agent, or Firm* — Charney IP Law LLC; Thomas M. Finetti

(57) ABSTRACT

The present disclosure provides a method of separating cellular particles from a tissue sample and then sorting the cellular particles into two or more cellular particle populations.

21 Claims, 25 Drawing Sheets

Related U.S. Application Data

(60) Provisional application No. 62/485,550, filed on Apr. 14, 2017.

(56) References Cited

U.S. PATENT DOCUMENTS

| | | | |
|---|---|---|---|
| 2010/0139377 A1* | 6/2010 | Huang | C02F 1/688 73/61.75 |
| 2011/0020459 A1 | 1/2011 | Achrol et al. | |
| 2014/0008307 A1* | 1/2014 | Guldiken | B01L 3/502761 422/502 |
| 2014/0248621 A1* | 9/2014 | Collins | G01N 33/4833 435/6.12 |
| 2015/0104845 A1* | 4/2015 | Huang | B01L 3/502761 435/173.9 |
| 2021/0154668 A1* | 5/2021 | Huang | G01N 29/222 |

FOREIGN PATENT DOCUMENTS

| | | |
|---|---|---|
| JP | 2016503489 A | 2/2016 |
| WO | 2013181532 A1 | 12/2013 |
| WO | 2016172623 A1 | 10/2016 |
| WO | 2017079763 A1 | 5/2017 |

OTHER PUBLICATIONS

C F Duffy et al, "Fast electrophoretic analysis of individual mitochondria using microchip capillary electrophoresis with laser induced fluorescence detection", Lab on a Chip, vol. 6, No. 8, 2006, p. 1007, XP055488484.

Aaheli Roy Choudhury, "Cell Isolation and Separation Techniques", Apr. 10, 2017 (Apr. 10, 2017), vol. 7, p. 2260.

Gi-Hun Lee et al, "Separation and sorting of cells in microsystems using physical principles", Journal of Micromechanics & Microengineering, vol. 26, No. 1, 2015, p. 13003, XP020292087.

International Search Report and Written Opinion for PCT/EP2018/058809 dated Oct. 15, 20219.

International Preliminary Report on Patentability for PCT/EP2018/058809, dated Oct. 15, 2019.

International Search Report for PCT/EP2018/058809, dated Sep. 10, 2018.

Lee et al., All-in-One Centrifugal Microfluidic Device for Size-Selective Circulating Tumor Cell Isolation with High Purity, Anal. Chem. 2014, 86, 11349-11356.

Duffy et al., Fast electrophoretic analysis of individual mitochondria using microchip capillary electrophoresis with laser induced fluorescence detection, Lab Chip, 2006, 6, 1007-1011, 1007.

Choudhury, Cell Isolation and Separation Techniques, Mater Methods 2017;7:2260.

Lee at al., Separation and sorting of cells in microsystems using physical principles, J. Micromech. Microeng. 26 (2016)013003 (15pp).

Toyama, "Development of Microfluidic Cell Nucleus Separator Employing Rapid Chemical Treatment," 2010 International Symposium on Micro-NanoMechatronics and Human Science, Nov. 7-10, 2010, DOI: 10.1109/MHS.2010.5669584; Electronic ISBN:978-1-4244-7997-9.

Tesauro, "Isolation of functional mitochondira by interial microfluidics— a new method to sort intracellular organelles form a small scale biological sample," RSC Adv., 2017, 7, 23735.

Lee, "Separation and sorting of cells in microsystems using physical principles," J. Micromech. Microeng. 26 (2016) 013003 (15pp).

Lee, "All-in-One Centrifugal Microfluidic Device for Size-Selective Circulating Tumor Cell Isolation with High Purity," dx.doi.org/10.1021/ac5035049 | Anal. Chem. 2014, 86, 11349-11356.

Duffy, Fast electrophoretic analysis of individual mitochondria using microchip capillary electrophoresis with laser induced fluorescence detection, Lab Chip, 2006, 6, 1007-1011.

Choudhury, "A comprehensive review of cell isolation methods," Mater Methods 2017;7:2260, //dx.doi.org/10.13070/mm.en.7.2260.

\* cited by examiner

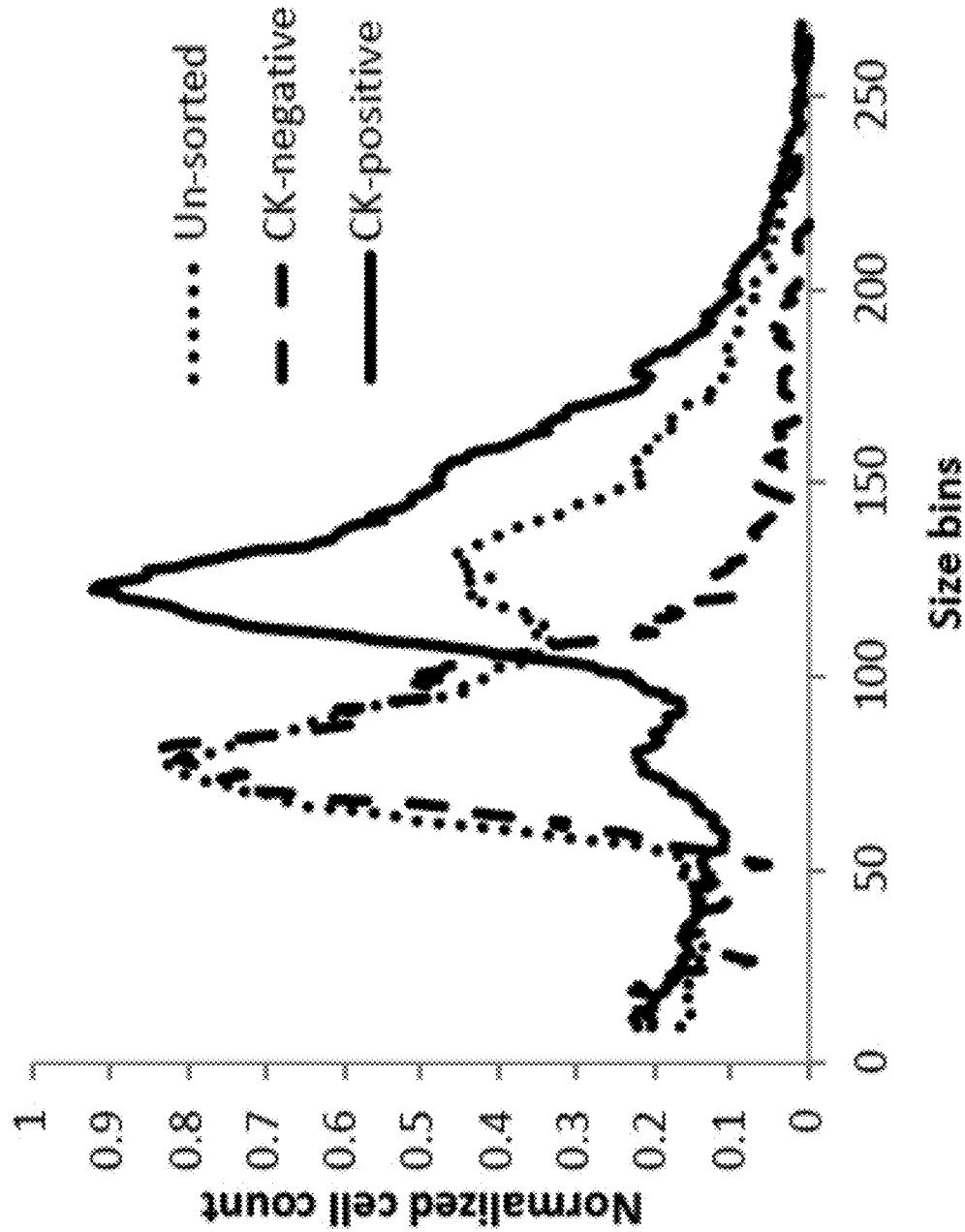

FIG. 15D

| Flow Sorted MAF% | Homogenate MAF% | Gene | AAChange.refGene |
|---|---|---|---|
| 41.38% | 17% | APC | APC:NM_001127511:exon14:c.C6916T:p.P2306S |
| 47.13% | 27% | BRAF | BRAF:NM_004333:exon15:c.T1799A:p.V600E |

SIZE-BASED SEPARATION OF DISSOCIATED FIXED TISSUES

CROSS REFERENCE TO RELATED APPLICATIONS

The present application is a continuation of International Application No. PCT/EP2018/058809, filed on Apr. 6, 2018, which application claims the benefit of the filing date of U.S. Provisional Patent Application No. 62/485,550 filed on Apr. 14, 2017, the disclosures of which are hereby incorporated herein by reference herein in their entireties.

BACKGROUND OF THE DISCLOSURE

Cancer is a disease marked by the uncontrolled proliferation of abnormal cells. In normal tissue, cells divide and organize within the tissue in response to signals from surrounding cells, resulting in normal cellular behavior that is carefully orchestrated by the tissue context. Cancer cells do not respond to growth-limiting contextual cues from the surrounding tissue, and they often harbor genetic alterations that drive them to proliferate and, in many organs, form a tumor. As the growth of a tumor progresses, genetic and phenotypic alterations continue to accumulate, allowing populations of cancer cells to overcome additional "checkpoints," such as an anti-tumor immune response, and manifesting as a more aggressive growth phenotype of the cancer cells. If left untreated, metastasis, the spread of cancer cells to distant areas of the body by way of the lymphatic system or bloodstream, may ensue. Metastasis results in the formation of secondary tumors at multiple sites, damaging healthy tissue. Most cancer death is caused by such secondary tumors.

Despite decades of advances in cancer diagnosis and therapy, many cancers continue to go undetected until late in their development. As a result, many solid tumors at the initial site of growth contain genetically and/or phenotypically heterogeneous tumor cell populations that are often spatially segregated. One or more of these cancer cell populations within the primary tumor may give rise to the secondary metastatic tumors. In addition, the tumor mass often consists of normal cells that are either recruited by the tumor to form a supportive environment (e.g. blood vessels) or were initially drawn to the tumor as a defensive mechanism by the host (e.g. immune cells) but were later overcome as the cancer evolved.

BRIEF SUMMARY OF THE DISCLOSURE

In one aspect of the present disclosure is a method of segregating cellular particles from a tissue sample, comprising: (i) homogenizing the tissue sample to provide a homogenized tissue sample; (ii) dissociating the homogenized sample into discrete cellular particles; and (iii) sorting cellular particles within the homogenized tissue sample into at least a first cellular particle population and a second cellular particle population, wherein the difference in size distribution of the two populations forms the underlying basis for their separation. In some embodiments, the sorting of the cellular particles is accomplished with a microfluidic device. In some embodiments, no staining is conducted prior to sorting. In some embodiments, staining is conducted prior to staining (e.g. staining using an antibody and then adding a secondary antibody connected to a bead that enhances a size difference). In some embodiments, the cellular particles are cells, and wherein the first cellular particle population comprises normal cells and the second cellular particle population comprises tumor cells. In some embodiments, the normal cells have an average diameter of less than 12 µm and the tumor cells have an average diameter of greater than 12 µm. In some embodiments, the tumor cells are derived from at least one of a whole tumor, a partial tumor, a metastatic tumor, a partial metastatic tumor, or lymph nodes.

In some embodiments, the cellular particles are nuclei, and wherein the first cellular particle population comprises normal nuclei and the second cellular particle population comprises tumor nuclei. In some embodiments, the normal nuclei have an average diameter of less than 8.5 µm and the tumor nuclei have an average diameter of greater than 8.5 µm.

In some embodiments, the tissue sample is derived from at least one of residual surgical material or a biopsy sample. In some embodiments, the tissue sample is one that was fixed in a crosslinking solution. In some embodiments, the tissue sample is derived from a fixed sample embedded in paraffin. In some embodiments, the homogenized sample is further processed prior to sorting, wherein the further processing comprises at least one of digesting proteins within the homogenized sample, heating the sample, or filtering the homogenized sample.

In some embodiments, a microfluidic device is used to separate the populations of cellular particles. In some embodiments, the microfluidic device is a deterministic lateral displacement device. In some embodiments, the microfluidic device is a hydrophoretic filtration device. In some embodiments the microfluidic device is a hydrodynamic filtration device. In some embodiments the microfluidic device utilizes inertial focusing in curved channels. In some embodiments the microfluidic device utilizes inertial focusing in straight channels. In some embodiments inertial focusing in straight channels comprises one of a pinched flow fractionation process or a hydrodynamic spreading process.

In some embodiments, the method further comprises the step of assaying the cellular particles within the first or second cellular particle populations for a first biomarker. In some embodiments, presence of the first biomarker is indicative of cancer, or otherwise informative concerning the clinical progression of the cancer patient. In some embodiments, first biomarker is an immune cell marker. In some embodiments, the method further comprises analyzing the first and second cellular particle populations for an RNA biomarker. For example, RNA expression analysis of the first cellular particle population, comprising primarily normal cells, may be used to identify the types of immune cell populations found amongst the infiltrating immune cells. In some embodiments, the method further comprises analyzing the first and second cellular particle populations for a protein biomarker.

In some embodiments, each of the first and second cellular particle populations are independently sequenced using next-generation sequencing. In some embodiments, each of the first and second cellular particles populations are independently analyzed using flow cytometry. In some embodiments, the first and second cellular particle populations provide matched tumor and normal samples for a patient. In some embodiments, the matched tumor and normal samples are analyzed to identify somatic mutations, copy number variations, or other genetic alterations.

In another aspect of the present disclosure is a method of segregating cells from a tissue sample comprising: homogenizing the tissue sample to provide a homogenized tissue sample; and sorting cells in the homogenized sample by size using a sorting device, wherein the cells are sorted into at least first and second cell populations, the first cell population enriched in cells having an average diameter ranging from about 5 μm to about 12 μm, and the second cell population enriched in cells having an average diameter ranging from about 12 μm to about 50 μm. In some embodiments, the first population of cells is enriched with non-tumor cells, and wherein the second population of cells is enriched with tumor cells.

In some embodiments, at least 80% of the cells in the first cell population have an average diameter ranging from about 5 μm to about 12 μm, and wherein at least 80% of the cells in the second cell population have an average diameter ranging from about 12 μm to about 50 μm (i.e. that sorting through the device results in a sample containing 80% of the target population). In some embodiments, at least 90% of the cells in the first cell population have an average diameter ranging from about 5 μm to about 12 μm, and wherein at least 90% of the cells in the second cell population have an average diameter ranging from about 12 μm to about 50 μm.

In some embodiments, the first or second cell population is rare (lower than 10%), and the successful outcome of sorting would be enrichment of that population to at least 20%, at least 30%, at least 40%, at least 50%, at least 60%, at least 70%, or at least 80%. In some embodiments, sorting facilitates a doubling of the percentage amount of any target population (e.g. enriching a target population from about 20% to about 40%).

In some embodiments, each of the at least first and second cell populations are independently sequenced using next-generation sequencing. In some embodiments, the at least first and second cell populations provide matched tumor and normal cell samples for a patient. In some embodiments, the matched tumor and normal cells are analyzed to identify somatic mutations, copy number variations, or other genetic alterations.

In some embodiments, the tissue sample is derived from a whole tumor, a partial tumor, and/or lymph nodes. In some embodiments, the tumor sample is derived from residual surgical material or a biopsy sample. In some embodiments, the tumor sample is derived from a sample embedded in paraffin. In some embodiments, the tissue sample is a fixed tissue sample, a fresh tissue sample, or any combination thereof.

In some embodiments, the homogenized tissue sample is further processed prior to sorting. In some embodiments, the further processing comprises the steps of digesting proteins within the homogenized sample and filtering the homogenized sample.

In some embodiments, the sorting device is a microfluidic device. In some embodiments, the microfluidic device is a deterministic lateral displacement device. In some embodiments, cells within the homogenized tissue sample having a critical diameter of less than about 12 μm move with a convective flow of the fluid passing through the device, while cells within the homogenized sample having a critical diameter of greater than about 12 μm move in a direction dictated by an arrangement of arrays. In some embodiments, nuclei within the homogenized tissue sample having a critical diameter of less than about 8.5 μm move with a convective flow of the fluid passing through the device, while nuclei within the homogenized sample having a critical diameter of greater than about 8.5 μm move in a direction dictated by an arrangement of arrays. In some embodiments, the microfluidic device is a hydrophoretic filtration device. In some embodiments, the microfluidic device is a hydrodynamic filtration device. In some embodiments, the microfluidic device employs inertial focusing in curved channels. In some embodiments, the microfluidic device employs inertial focusing in straight channels. In some embodiments, inertial focusing in straight channels comprises one of a pinched flow fractionation process or a hydrodynamic spreading process. In some embodiments, the sorting device does not require the step of staining the cells or nuclei.

In some embodiments, the method further comprises the step of assaying the cells within the first or second population for a first biomarker. In some embodiments, the first biomarker being one that, if present, is indicative of a cancer. In some embodiments, the first biomarker is an immune cell marker. In some embodiments, the method further comprises analyzing the first and second cellular particle populations for an RNA biomarker. In some embodiments, the method further comprises analyzing the first and second cellular particle populations for a protein biomarker.

In another aspect of the present disclosure is a method of segregating cells from a fresh tissue sample comprising: homogenizing a fresh tissue sample to provide a homogenized tissue ample; sorting cells in the homogenized tissue sample by size using a sorting device, wherein the cells are sorted into at least first and second cell populations, the first cell population enriched in cells having an average diameter ranging from about 6 μm to 12 μm, and the second cell population enriched in cells having an average diameter of greater than 12 μm. In some embodiments, staining is conducted prior to sorting. In some embodiments, staining is not conducted prior to sorting.

In some embodiments, the sorting device is a microfluidic device. In some embodiments, the microfluidic device is a deterministic lateral displacement device. In some embodiments, cells within the homogenized sample having a critical diameter of less than about 6 μm move with a convective flow of the fluid passing through the device, while cells within the homogenized sample having a critical diameter of greater than about 6 μm move in a direction dictated by an arrangement of arrays. In some embodiments, the microfluidic device is a hydrophoretic filtration device. In some embodiments, the microfluidic device is a hydrodynamic filtration device. In some embodiments, the microfluidic device utilizes inertial focusing in curved channels. In some embodiments, the microfluidic device utilizes inertial focusing in straight channels. In some embodiments, inertial focusing in straight channels comprises one of a pinched flow fractionation process or a hydrodynamic spreading process. In some embodiments, sorting device does not require the step of staining the cells.

In another aspect of the present disclosure is a method of sequencing genomic material within a sample comprising: homogenizing a tissue sample to provide a homogenized tissue sample; and sequencing at least a first population of cells or cell nuclei derived from the homogenized tissue sample which are enriched with tumor cells or tumor nuclei. In some embodiments, cells or cell nuclei within the homogenized tumor sample are sorted with a microfluidic device to provide two populations of cells or cell nuclei. In some embodiments, at least 70% of the cells or cell nuclei within the first population of cells are tumor cells. In some embodiments, at least 70% of the cells or cell nuclei within the first population of cells have a size greater than 12 μm (cells) or 8.5 μm (nuclei). In some embodiments, at least 80% of the cells or cell nuclei within a first population of cells are tumor cells or tumor nuclei.

In some embodiments, the cells or cell nuclei derived from the homogenized tissue sample are sorted according to their hydrodynamic size. In some embodiments, the cells or cell nuclei are sorted with a microfluidic device. In some embodiments, the microfluidic device does not require staining of the cells or cell nuclei prior to sorting. In some embodiments, microfluidic device employs one of deterministic lateral displacement, hydrophoretic filtration, hydrodynamic filtration, inertial focusing in curved channels, and inertial focusing in straight channels.

In some embodiments, the first population of cells or cell nuclei comprises at least 0.05 micrograms of genomic material for sequencing. In some embodiments, the first population of cells or cell nuclei comprises at least 0.1 micrograms of genomic material for sequencing. In some embodiments, the first population of cells or cell nuclei comprises at least 0.5 micrograms of genomic material for sequencing. In some embodiments, the sequencing method comprises at most 4 amplification cycles prior to sequencing. In some embodiments, the sequencing method comprises at most 6 amplification cycles prior to sequencing. In some embodiments, the sequencing method comprises at most 8 amplification cycles prior to sequencing. In some embodiments, no amplification cycles are needed prior to sequencing.

In another aspect of the present disclosure is a method of deriving an enriched population of tumor nuclei and an enriched population of normal nuclei from a tumor sample, comprising dissociating tumor and normal nuclei from the tumor sample; and sorting the tumor and normal nuclei by size with a microfluidic sorting device, where the microfluidic sorting device does not require a step of staining or biomarker analysis prior to sorting. In some embodiments, the enriched population of tumor nuclei comprises at least 85% tumor nuclei; and wherein the enriched population of normal nuclei comprises at least 85% normal nuclei. In some embodiments, the tumor nuclei within the enriched population of tumor nuclei comprises an average nucleus size of greater than 8.5 µm. In some embodiments, the normal nuclei within the enriched population of normal nuclei comprises an average nucleus size of less than 8.5 µm. In some embodiments, sorting facilitates a doubling of the percentage amount of any target population (e.g. enriching a target population from about 20% to about 40%).

In some embodiments, the method further comprises the step of separately sequencing the enriched population of tumor nuclei and the enriched population of normal nuclei. In some embodiments, at least one of somatic mutations, copy number variations, or other genetic alterations are identified in the enriched population of tumor nuclei.

In some embodiments, the tumor sample is derived from a whole tumor, a partial tumor, one or more lymph nodes, and/or a sample embedded in paraffin. In some embodiments, the tumor sample comprises freshly dissociated tissue.

In another aspect of the present disclosure is a method of treating cancer by identifying cancer subtypes responsive to a particular treatment or active pharmaceutical ingredient, wherein the cancer subtype is identified by sequencing a sample enriched in tumor cells, wherein the sample is enriched in tumor cells or tumor nuclei by homogenizing an input tissue (e.g. a sample comprising at least one of a tumor, one or more lymph nodes, or blood); and sorting the tumor cells or tumor nuclei from normal cells or normal nuclei in the homogenized sample with a size-based sorting device, and where the size-based sorting device does not require staining the tumor cells or tumor nuclei prior to sorting. In some embodiments, staining is performed prior to sorting. In some embodiments, the population of cells enriched in tumor cells or tumor nuclei comprises a sufficient amount of genomic material such that at most four amplification cycles are conducted prior to sequencing.

In some embodiments, at most 2 amplification cycles are conducted prior to sequencing. In some embodiments, the quantity of genomic material is at least 0.01 micrograms. In some embodiments, the quantity of genomic material is at least 0.1 micrograms. In some embodiments, the quantity of genomic material is at least 0.2 micrograms. In some embodiments, quantity of genomic material is at least 0.5 micrograms. In some embodiments, following identification of the cancer subtype, a course of treatment is provided to a patient from which the sample was derived. In some embodiments, the size-based sorting device does not require any step of staining prior to sorting. In some embodiments, the staining is conducted prior to sorting.

In another aspect of the present disclosure is a method of treating cancer by identifying somatic mutations in tumor cells or tumor nuclei comprising homogenizing a tissue sample derived from a patient; dissociating cells within the homogenized tissue sample; and separating tumor cells or tumor nuclei from normal cells or normal nuclei in the dissociated tissue sample with a microfluidic device to provide a first population enriched with tumor cells or tumor nuclei having an average diameter ranging from about 5 µm to about 12 µm (cells) or 4 µm to about 8.5 µm (nuclei), and a second population enriched with normal cells or normal nuclei having an average diameter ranging from about 12 µm to about 50 µm (cells) or 8.5 µm to about 25 µm (nuclei), wherein the microfluidic device does not require staining or labeling prior to sorting. In some embodiments, the microfluidic device employs one of deterministic lateral displacement, hydrophoretic filtration, hydrodynamic filtration, inertial focusing in curved channels, and inertial focusing in straight channels. In some embodiments, the cell populations are enriched without first staining the cells.

In another aspect of the present disclosure is a method of segregating cells, nuclei, or tissue aggregates from a tissue sample to facilitate downstream analysis comprising: separating the cells, nuclei, or tissue aggregates from the tissue sample to provide a separated sample; sorting the cells, nuclei, or tissue aggregates in the separated sample by size using a sorting device, wherein the cells, nuclei, or tissue aggregates are sorted into first and second populations, the first population having a first cell, nuclei, or tissue aggregate average diameter and the second population having a second cell, nuclei, or tissue aggregate average diameter. In some embodiments, the sorting device is a microfluidic device. In some embodiments, the microfluidic device employs one of deterministic lateral displacement, hydrophoretic filtration, hydrodynamic filtration, inertial focusing in curved channels, and inertial focusing in straight channels. In some embodiments, the method further comprises the step of performing a genomic analysis on at least one of the first or second populations. In some embodiments, the method further comprises the step of performing a flow cytometry analysis on at least one of the first or second populations. In some embodiments, the method further comprises the step of staining at least one of the first or second populations for the presence of at least one biomarker.

In another aspect of the present disclosure is a composition enriched with tumor cells, the tumor cells having a size greater than 12 µm, wherein the tumor cells were separated from normal cells without first staining either the tumor or normal cells. In another aspect of the present disclosure is a composition enriched with tumor nuclei, the tumor nuclei having a size greater than 8.5 µm, wherein the tumor nuclei were separated from normal nuclei without first staining either the tumor or normal nuclei. In some embodiments, at least 40% of the composition comprises tumor cells or nuclei. In some embodiments, at least 50% of the composition comprises tumor cells or nuclei. In some embodiments, at least 60% of the composition comprises tumor cells or nuclei. In some embodiments, at least 70% of the composition comprises tumor cells or nuclei. In some embodiments, at least 80% of the composition comprises tumor cells or nuclei. In some embodiments, at least 90% of the composition comprises tumor cells or nuclei. In some embodiments, at least 95% of the composition comprises tumor cells or nuclei. In some embodiments, the tumor population is rare (lower than 10%), and the composition after sorting would be enrichment of that population to at least 20%, at least 30%, at least 40%, at least 50%, at least 60%, at least 70%, or at least 80%. In some embodiments, composition of the enriched sample is a doubling of the initial percentage of the tumor population.

In another aspect of the present disclosure is a kit comprising a first population of cells and a second population of cells, the first population of cells substantially enriched with tumor cells having a size greater than 12 μm, the second population of cells substantially enriched with normal cells having a size less than 12 μm, the first and second population of cells are derived from the same tumor sample, and wherein the tumor cells and normal cells are unstained. In another aspect of the present disclosure is a kit comprising a first population of nuclei and a second population of nuclei, the first population of nuclei substantially enriched with tumor nuclei having a size greater than 8.5 μm, the second population of nuclei substantially enriched with normal cells having a size less than 8.5 μm, the first and second population of nuclei are derived from the same tumor sample, and wherein the tumor nuclei and normal nuclei are unstained.

Current diagnostic tools face a significant hurdle in sufficiently representing genetically heterogeneous cancer cells and different cell types comprising a tumor mass, largely because current tumor sampling schemes only use a very small, localized fraction of each tumor for all of the diagnostic tests. Applicants have developed a new approach to sample tumors such that meaningful information may be derived from the sampled tumor. Achieving this goal allows for a more accurate snapshot of the alterations driving the cancer, better therapeutic approaches for the patient, and a better prediction of potential mechanisms of therapeutic resistance as detailed herein.

It is believed that isolating and sorting cells from complex, heterogeneous mixtures represent a critical task in many areas of biology, biotechnology, and medicine. Indeed, it is believed that different tumors have varying percentages of tumor cells and normal cells. As a result, representative samples from tumors with higher percentages of contaminating normal tissue (e.g. due to immune infiltration) are believed to be more costly to sequence since a portion of the reads will be "wasted" on normal DNA. As used herein a "read" refers to the sequence of a cluster that is obtained after the end of the sequencing process which is ultimately the sequence of a section of a unique fragment of a fragmented nucleic acid sequence. Current clinical sequencing from tumor tissue curls from blocks also inadvertently waste reads on contaminating normal tissue (as used herein, "tissue curls" refer to sections of tissue of a defined thickness cut from an FFPE block, usually with a microtome). Thus, it is believed that the mixture of tumor and normal (immune) cells, in both representative samples and archival tissue samples from blocks, poses challenges for sequencing tumor tissue In addition, it is often important to sequence a separate non-malignant tissue source from the same patient in order to define true somatic mutations apart from genetic polymorphisms present in the non-malignant tissue. For archival tumor blocks, these non-malignant tissues may not have been collected. Furthermore, there may be sequencing applications for which it is critical to isolate the immune component from the tumor tissue. In view of this, there exists a need to enrich normal tissue from representative samples and tissue blocks.

Analysis of dissociated representative samples by flow cytometry is also made more difficult by the mixture of tumor cells and normal (immune) cells, which often express biomarkers that are unique to each type of tissue. The ability to separate the different cell types prior to downstream analysis would, it is believed, enable a more straightforward analysis of dissociated fixed tissue samples by flow cytometry.

In view of the foregoing, Applicants have developed a method of sorting whereby a heterogeneous mixture of tumor cellular particles and normal cellular particles may be enriched or purified into one or more well-defined populations (e.g. a tumor population or a normal cell population) so as to enhance efficiency in research, tumor analysis, and other downstream processing tasks (e.g. genome sequencing, FACS analysis, RNA or protein biomarker analysis). In some embodiments, the method developed by Applicants does not require the staining or labeling of cells or nuclei prior to sorting and thus establishes a superior method of sorting as compared with fluorescence-activated cell sorting (FACS) or methods employing magnetic-activated cell sorting (although, staining may be employed prior to sorting). Moreover, the methods of generating enriched populations of cellular particles (e.g. cells or cell nuclei) according to the present disclosure allow, it is believed, for a reduction in the costs of genome sequencing. Applicants also submit that the methods disclosed herein may be used to generate matched tumor and normal cell populations from a single patient sample, such as from residual surgical material or extracted archival samples from paraffin blocks.

Applicants have also discovered that the sorting devices described herein facilitate the provision of a matched tumor sample and normal sample for each patient, enabling the identification of true somatic mutations through sequencing, especially for archival samples that lack a non-malignant tissue sample from the same patient. It is believed that enrichment of tumor and normal populations may also reduce the cost of sequencing and potentially simplify analysis by flow cytometry.

BRIEF DESCRIPTION OF THE FIGURES

FIG. 7B sets forth a size distribution of sorted nuclei from representative lung squamous cell carcinoma tumor samples. The graphs show Coulter counter analysis, with traces smoothed using a moving average. Dotted traces correspond to unsorted nuclei; dashed traces correspond to cytokeratin (CK)-negative nuclei sorted using FACS; black traces correspond to cytokeratin (CK)-positive nuclei sorted using FACS.

FIG. 15D illustrates sequencing data for FACS-enriched tumor samples, where large cells are identified as tumor cells based upon an increased allele fraction of clonal tumor mutations. The chart shows allele frequencies of two clonal drivers in the homogenate vs. FACS sorted nuclei. Note that for FACS-sorted tumor nuclei, the mutant allele frequency (MAF %) approaches 50%, which is the upper limit expected for a dominant clonal driver mutation.

DETAILED DESCRIPTION

Overview

Figure 1:
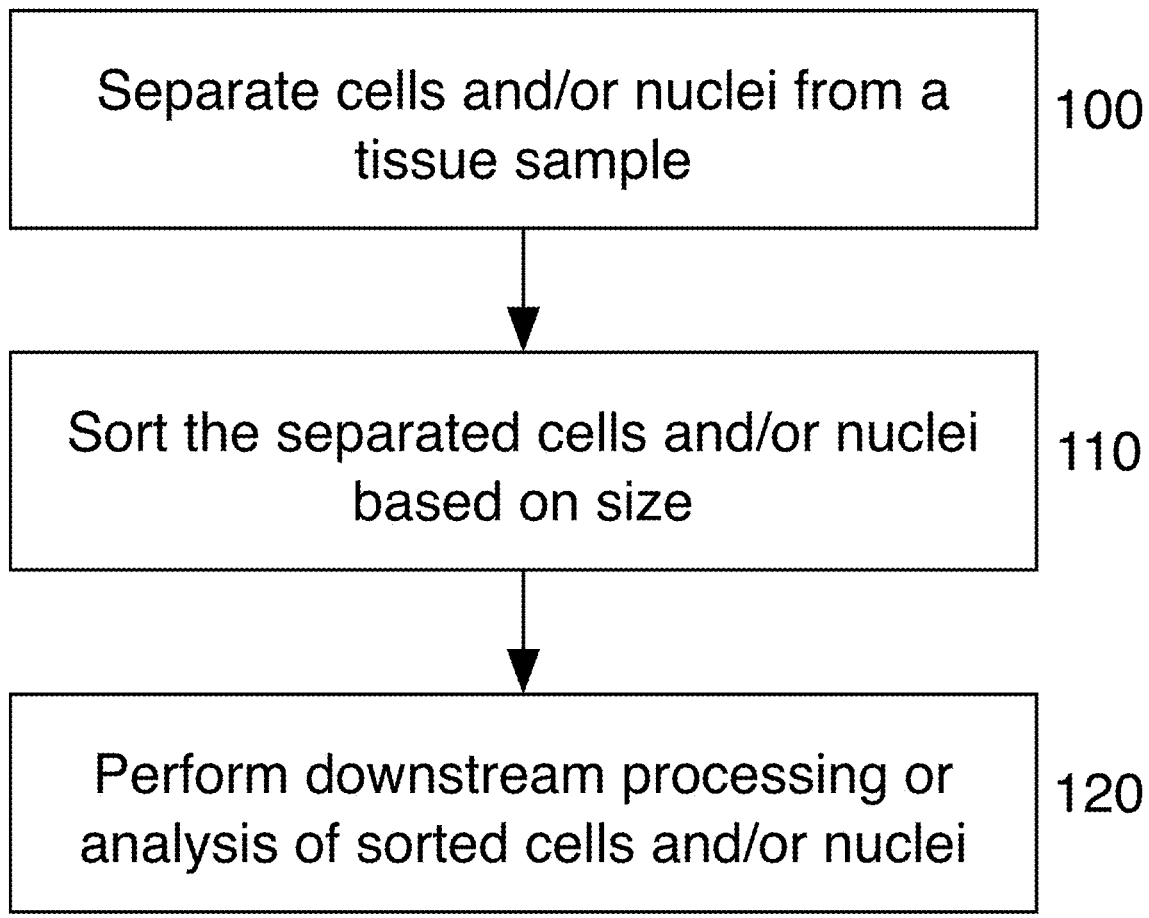
FIG. 1 sets forth a flow chart illustrating a method according to one embodiment of the present disclosure.

In general, the present disclosure provides a method of separating or segregating cellular particles (e.g. cells, nuclei) and/or small tissue aggregates from a tissue sample (step 100) (e.g. a tumor sample, a lymph node sample, etc.) and then sorting the cellular particles and/or small tissue aggregates, such as by size or hydrodynamic size (step 110), into two or more populations (e.g. a tumor cellular particle population, a normal cellular particle population), such that each population of cellular particles and/or small tissue aggregates may be analyzed (step 120) (see FIG. 1). As such, the present disclosure enables an approach for fractionation of fixed dissociated tissue upstream of sequencing and/or protein or RNA biomarker analysis. In some embodiments, each cellular particle population or sorted fraction thereof is enriched with a particular type of cellular particle (e.g. tumor cells, normal cells, tumor nuclei, normal nuclei) or tumor tissue aggregates or normal tissue aggregates.

The present disclosure also provides devices, e.g. microfluidic devices, and methods of using such devices for enriching and analyzing subpopulations of tumor cellular particles and normal cellular particles (e.g. tumor cells, normal cells, tumor nuclei, normal nuclei). In some embodiments, the devices of the present disclosure incorporate arrays, such as arrays of obstacles, that allow displacement of cells, nuclei, or tissue aggregates having a predetermined size, thereby offering a mechanism of providing a sample enriched in a certain population of cells, nuclei, or tissue aggregates. In some embodiments, the arrays are sized according the sizes typically associated with normal cells or tumor cells, such as disclosed herein.

The present disclosure further provides methods of diagnosing a condition in a subject, e.g., cancer, by analyzing a sample from the subject (step 120), the sample being separated from tissue (step 100) and then sorted (step 110), such as with a microfluidic sorting device, prior to analysis (step 120). In some embodiments, the present disclosure provides a method of analyzing cancer cells or nuclei in a cellular sample by introducing the cellular sample into a device having at least one channel including a structure that directs the cancer cells or nuclei in a first direction to produce a first output sample enriched in the cancer cells or nuclei and directs non-cancerous cells or nuclei in a second direction to produce a second output sample enriched in the non-cancerous cells or nuclei; and performing an analysis of the population enriched in cancer cells or nuclei, e.g. a genomic analysis. In some embodiments, a genomic analysis is performed for both the cancerous and non-cancerous cell or nuclei populations.

In some embodiments, the methods allow for the provision of tumor-enriched tissue matched to enriched normal tissue so as to reduce sequencing costs and enable bioinformatics analysis.

Definitions

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary. The term "amplification," as used herein, refers to a process of multiplying an original quantity of a nucleic acid template in order to obtain greater quantities of the original nucleic acid.

Likewise, the term "amplifying" refers to a process whereby a portion of a nucleic acid is replicated using, for example, any of a broad range of primer extension reactions. Exemplary primer extension reactions include, but are not limited to, polymerase chain reaction (PCR). Unless specifically stated, "amplifying" refers to a single replication or to an arithmetic, logarithmic, or exponential amplification. In general, PCR is a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured, and the primers are then annealed to their complementary sequences within the target molecule. Following annealing, the primers are extended with a polymerase (e.g. DNA polymerase) so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment (the amplicon) of the desired target sequence. The length of the amplified segment of the desired target sequence is determined by the relative positions of the primers with respect to each other, and therefore, this length is a controllable parameter. Polymerase chain reaction ("PCR") is described, for example, in U.S. Pat. Nos. 4,683, 202; 4,683,195; 4,000,159; 4,965,188; 5,176,995), the disclosures of each are hereby incorporated by reference herein in their entirety.

As used herein, the term "biological sample" or "tissue sample" refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "biomarker" refers to a biological molecule found in blood, other body fluids, or tissues that is a sign of a normal or abnormal process, or of a condition or disease (such as cancer). A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in non-invasively collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT(Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the term "enriched sample" means a sample comprising components that has been processed to increase the relative population of components of interest relative to other components typically present in a sample. In some embodiments, the methods disclosed herein utilize devices to enrich or sort at least one type of cell from others in a stream comprising a mixture of cell types (e.g. tumor cells and normal cells). As used herein, the term "enrich" (and similarly the terms "isolate" or "sort") does not mean that the enriched target cells, nuclei, or tissue aggregates are 100% isolated from other non-target cells, nuclei, or tissue aggregates but simply that the mixture has experienced some amount of enrichment as compared to the starting mixture. For example, samples can be enriched by increasing the relative population of cells of interest by at least 10%, 25%, 50%, 75%, 100% or by a factor of at least 10, 100, 1,000, 10,000, 100,000, 1,000,000, 10,000,000, or even 100,000,000.

As used herein, the term "cellular particle" refers to an individual cell or an organelle released from the cell. In some embodiments, the organelle released from the cell is a cell nucleus. In other embodiments, the organelle released from the cell is a cell nucleus containing remnants of cytoplasmic material that may be used to identify the cell of origin of the nucleus. For example, cytokeratin may remain attached to the nucleus and be used as a protein marker for nuclei originating from a tumor cell.

As used herein, the term "fixed" refers to a tissue sample that has been incubated in a crosslinking solution with the goal of preserving the cellular and/or architectural integrity of the tissue sample. Common examples of crosslinking solutions include neutral buffered formalin, methanol, alcoholic formalin, bouins, etc.

As used herein, the term "H&E" refers to staining with the primary stains hematoxylin and eosin.

As used herein, the term "hydrodynamic size" is meant the effective size of a particle when interacting with a flow, obstacles, or other particles. It is used as a general term for particle volume, shape, and deformability in the flow.

As used herein, the term "homogenizing" refers to a process whereby a biological sample is brought to a state such that all fractions of the sample are equal in composition. In the present disclosure, the "homogenization" will in general preserve the integrity of the majority of the cells within the sample, e.g., at least 50, 80, 85, 90, 95, 96, 97, 98, 99, 99.9% or greater percentage of the cells in the sample will not be ruptured or lysed as a result of the homogenization process. The homogenates may be substantially dissociated into individual cells (or clusters of cells) and the resultant homogenate or homogenates are substantially homogeneous (consisting of or composed of similar elements or uniform throughout).

As used herein, the terms "label" or "stains" refer a reagent that is capable of binding to an analyte, being internalized or otherwise absorbed, and being detected, e.g., through shape, morphology, color, fluorescence, luminescence, phosphorescence, absorbance, magnetic properties, or radioactive emission.

As used herein, the term "lymph node" refers to an oval- or kidney-shaped organ of the lymphatic system, present widely throughout the body including the armpit and stomach and linked by lymphatic vessels. Lymph nodes contain a diverse number of immune cells, including but not limited to B cells and T cells. In some embodiments, lymph nodes may contain hidden tumor cells.

As used herein, the term "microfluidic" is meant having at least one dimension of less than 1 mm.

As used herein, the term "next generation sequencing (NGS)" refers to sequencing technologies having high-throughput sequencing as compared to traditional Sanger- and capillary electrophoresis-based approaches, wherein the sequencing process is performed in parallel, for example producing thousands or millions of relatively small sequence reads at a time. Some examples of next generation sequencing techniques include, but are not limited to, sequencing by synthesis, sequencing by ligation, and sequencing by hybridization. These technologies produce shorter reads (anywhere from 25-500 bp) but many hundreds of thousands or millions of reads in a relatively short time. The term "next-generation sequencing" refers to the so-called paralleled sequencing-by-synthesis or sequencing-by-ligation platforms currently employed by Illumina, Life Technologies, and Roche etc. Next-generation sequencing methods may also include nanopore sequencing methods or electronic-detection based methods such as Ion Torrent technology commercialized by Life Technologies.

As used herein, the term "normal tissue" refers to a tissue having no detectable lesion or abnormality that putatively correlates to an increased incidence of disease or in the context of cancer, malignancy. These normal samples may be derived from patients having genetic mutations or conditions that correlate with an increased incidence of disease (genetic or otherwise), cancer or malignancy. Normal tissue can be of the same type of tissue corresponding to the pathologic tissue from the same individual, or different individual; or normal tissue that is not related (e.g., either from a different location in the body or with a different histologic type) to the pathologic tissue either from the same individual or form other individuals.

As used herein, the term "obstacle" refers to an impediment to flow in a channel, such as a flow channel in a microfluidic device, e.g., a protrusion from one surface. For example, an obstacle may refer to a post outstanding on a base substrate or a hydrophobic barrier for aqueous fluids. In some embodiments, the obstacle may be partially permeable. For example, an obstacle may be a post made of porous material, wherein the pores allow penetration of an aqueous component but are too small for the particles being separated to enter.

As used herein, the terms "representative sample" and "representative sampling" as used herein refer to a sample (or a subset of a sample) that accurately reflects the components of the entirety and, thus, the sample is an unbiased indication of the entire population. In general, this means that the different types of cells and their relative proportion or percentages within the representative sample or a portion thereof essentially accurately reflects or mimics the relative proportion or percentages of these cell types within the entire tissue specimen, generally a solid tumor or portion thereof.

As used herein, "sequencing" or "DNA sequencing" refers to biochemical methods for determining the order of the nucleotide bases, adenine, guanine, cytosine, and thymine, in a DNA oligonucleotide. Sequencing, as the term is used herein, can include without limitation parallel sequencing or any other sequencing method known of those skilled in the art, for example, chain-termination methods, rapid DNA sequencing methods, wandering-spot analysis, Maxam-Gilbert sequencing, dye-terminator sequencing, or using any other modern automated DNA sequencing instruments.

As used herein, the term "substantially" means the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. In some embodiments, "substantially" means within about 20%. In some embodiments, "substantially" means within about 15%. In some embodiments, "substantially" means within about 10%. In some embodiments, "substantially" means within about 5%.

As used herein, the term "tumor" refers to a mass or a neoplasm, which itself is defined as an abnormal new growth of cells that usually grow more rapidly than normal cells and will continue to grow if not treated sometimes resulting in damage to adjacent structures. Tumor sizes can vary widely. A tumor may be solid or fluid-filled. A tumor can refer to benign (not malignant, generally harmless), or malignant (capable of metastasis) growths. Some tumors can contain neoplastic cells that are benign (such as carcinoma in situ) and, simultaneously, contain malignant cancer cells (such as adenocarcinoma). This should be understood to include neoplasms located in multiple locations throughout the body. Therefore, for purposes of the disclosure, tumors include primary tumors, lymph nodes, lymphatic tissue, and metastatic tumors.

As used herein, the term "tumor sample" encompasses samples prepared from a tumor or from a sample potentially comprising or suspected of comprising cancer cells, or to be tested for the potential presence of cancer cells, such as a lymph node.

Separation of Cellular Particles from Tissue

Figure 2:
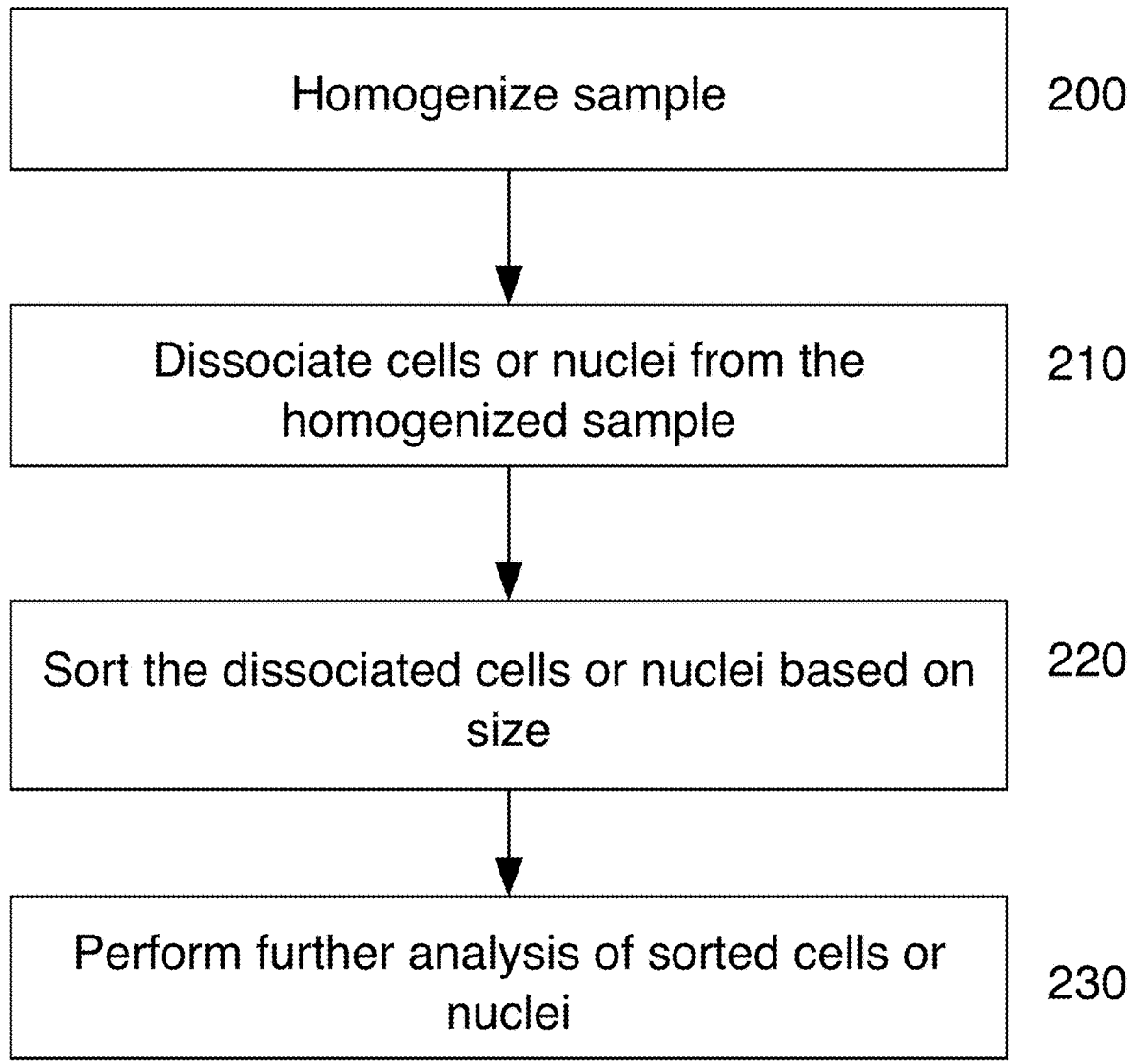
FIG. 2 sets forth a flow chart illustrating a method according to another embodiment of the present disclosure.
Figure 3:
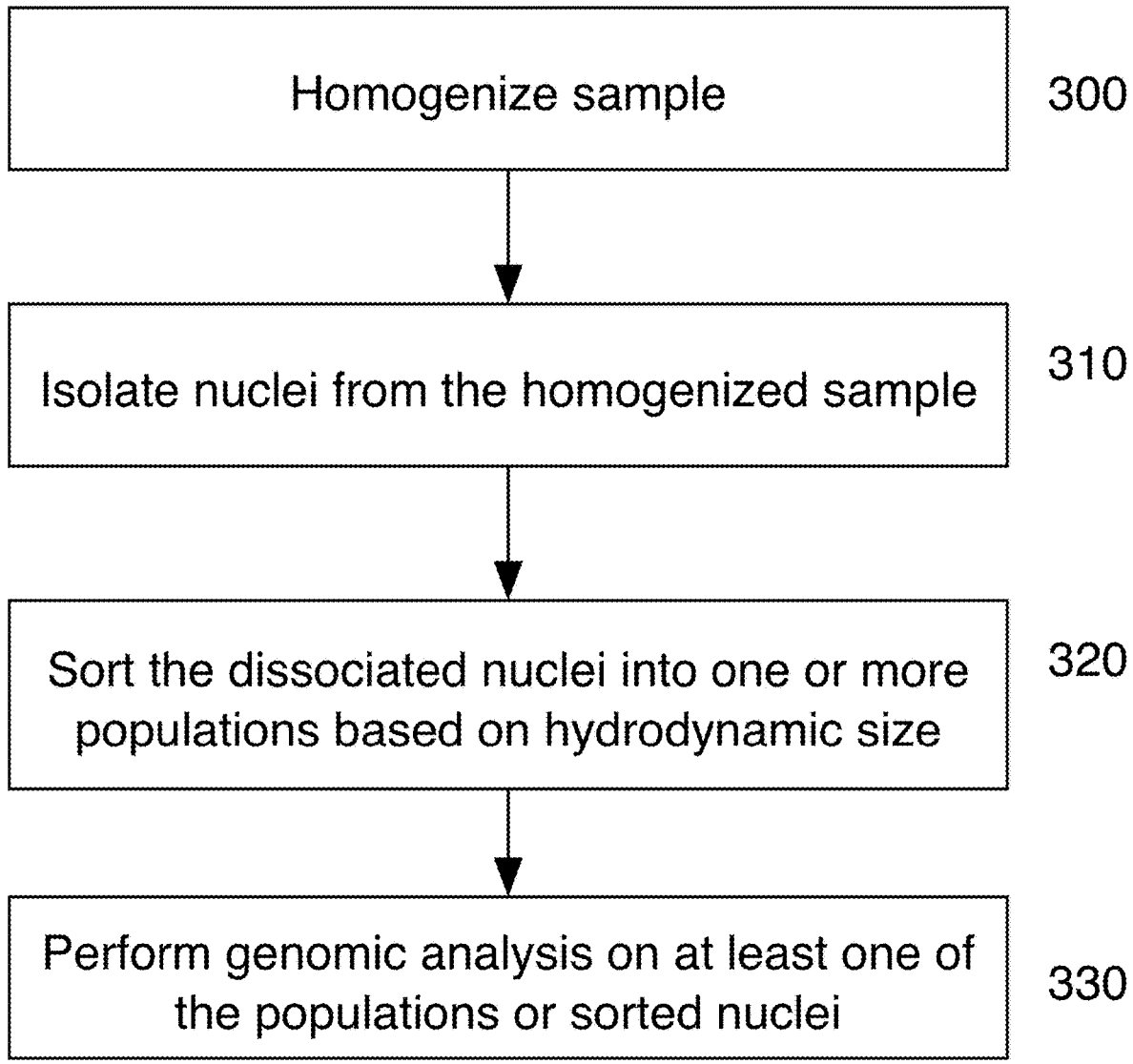
FIG. 3 sets forth a flow chart illustrating a method according to another embodiment of the present disclosure.

With reference to FIGS. 1 and 2, in some embodiments, cellular particles (e.g. cells, nuclei, and/or small tissue aggregates) are separated from tissue (step 100), such as by homogenizing the tissue sample (step 200) and then dissociating the cellular particles present in the homogenized sample (step 210). The dissociated cellular particles may then be sorted (step 220) and analyzed (step 230).

In some embodiments, the tissue sample for homogenization (step 200) and dissociation (step 210) is derived from a tumor (cancerous or non-cancerous), a metastatic lesion, normal tissue, whole blood, or a lymph node. In some embodiments, the tissue sample is a residual surgical sample, a biopsy sample, or a histological sample. In some embodiments, the tissue sample is a fresh sample, namely one that has not been preserved. In some embodiments, the tissue sample is a fixed tissue sample. In some embodiments, the tissue sample is derived from a formalin-fixed paraffin-embedded tissue block. In some embodiments, multiple tissue sources may be combined and then the cellular particles, such as cells and/or nuclei, are separated from the collective tissue samples. In some embodiments, cellular particles are dissociated from the tissue sample without a homogenization step.

Particular embodiments for homogenizing and/or dissociating cellular particles from tissue are set forth in the Examples herein.

Homogenization of Tissue Samples

In some embodiments, a tumor sample, lymph node sample, and/or other tissue sample is homogenized (step 200) by placing the sample into a mechanical shearing apparatus, e.g. a blender or an ultra sonicator. The homogenization produces a range of tissue fragments. Methods of preparing homogenized tumor samples or lymph node samples are disclosed in co-pending PCT Application No. PCT/US2016/060861 (filed Nov. 1, 2016), the disclosure of which is hereby incorporated by reference herein in its entirety.

In some embodiments, the homogenized sample is a representative sample, as defined herein. Accordingly, following sufficient mechanical shearing to disassociate the tumor, lymph node, and/or other tissue sample, all the subpopulations of tumor cells that were originally spatially segregated within the original sample are distributed throughout the newly homogenized sample. That is, as a result of homogenizing a tumor, one or more lymph nodes, or any combination thereof, any heterogeneity of cells within the tumor is substantially homogeneously (uniformly) distributed within the resultant homogenate or a portion or fraction thereof, such that the homogenate (or any fraction thereof) substantially homogeneously expresses the heterogeneity of the tumor and/or lymph node sample which was the input. By homogenizing tumors and/or lymph nodes to generate a sample (or homogenate) that is representative of the tumor in its entirety, it is possible, in some embodiments, to characterize the landscape (such as the heterogeneity) of the tumor, e.g. it may be possible to sequence each of the different populations of cells or nuclei contained throughout (step 230), including different tumor subpopulations, i.e. those having different genomic profiles.

Dissociation of Cells, Nuclei, and/or Small Tissue Aggregates from Tumors

The homogenized samples (from step 200) may be further dissociated and/or treated to provide dissociated cellular particles (such as dissociated cells or nuclei) and/or small tissue aggregates (step 210). In general, there are three primary methods for tissue dissociation including enzymatic dissociation, chemical dissociation and mechanical dissociation or any combination thereof. The selection of a method for dissociation is usually made based on the tissue type and tissue origin.

Enzymatic dissociation is the process of using enzymes to digest tissue pieces thereby releasing cells from tissue. Many different types of enzymes may be used in this process and, as the skilled artisan will appreciate, certain enzymes are more effective with certain tissue types. The skilled artisan will also appreciate any enzymatic dissociation process may use one or more enzymes in combination with each other, or one or more enzymes in combination with other chemical and/or mechanical dissociation methods. Examples of suitable enzymes include, but are not limited to, collagenase, trypsin, elastase, hyaluronidase, papain, DNase I, neutral protease, and trypsin inhibitor.

Collagenase is a proteolytic enzyme used to digest proteins found in the extracellular matrix. Unique to enzymatic proteases, collagenase can attack and degrade the triple-helical native collagen fibrils that are commonly found in connective tissue. There exist four basic collagenase types, namely: Type 1, which is suitable for use in epithelial, liver, lung, fat and adrenal tissue cell specimens; Type 2, which is suitable for use in heart, bone, muscle, thyroid and cartilage tumor originating tissues given its high proteolytic activity; Type 3, which is suitable for use in mammary cells given its low proteolytic activity; and Type 4: which is suitable for islets and other research protocols where receptor integrity is important, given its tryptic activity.

Trypsin is described as a pancreatic serine (an amino acid) protease that has specificity for peptide bonds that involve the carboxyl group of arginine and lysine amino acids. It is considered one of the most highly specific proteases. Trypsin alone is not usually effective for tissue dissociation because it shows minimal selectivity to extracellular proteins. It is usually combined with other enzymes such as collagenase or elastase.

Elastase is another pancreatic serine protease, which has specificity for peptide bonds that are next to neutral amino acids. It is unique among proteases in its ability to hydrolyze native elastin. Elastase can also be found in blood components and bacteria. In some embodiments, it is suitable for isolation of Type II cells from lung tissue.

Hyaluronidase is a polysaccharidase, this enzyme is often used for dissociation of tissues, typically when combined with a more crude protease such as collagenase. It has affinity for bonds found in just about all connective tissues.

Papain is a sulfhydryl protease, it has wide specificity and so can degrade most protein substrates more thoroughly than pancreatic proteases, i.e. trypsin or elastase. Papain is frequently used to isolate neuronal materials from tissues.

Deoxyribonuclease I (DNase I) is frequently included in enzymatic cell isolation procedures to digest nucleic acids that leak into the dissociation medium and can increased viscosity and recovery problems. Without wishing to be bound by any particular theory, it is believed that DNaseI will not damage intact cells.

Neutral protease, such Dispase® (available from Worthington Biochemical), is a bacterial enzyme with mild proteolytic activity, Dispase® is useful for isolating primary and secondary cell cultures because of its ability to maintain cell membrane integrity. It has been found to more efficiently dissociate fibroblast-like cells as compared to epithelial-like cells. It is inhibited by EDTA.

A trypsin inhibitor is derived mainly from the soybean, it inactivates trypsin, and so is sometimes used for specific cell isolation protocols.

Chemical dissociation takes advantage of the fact that cations participate in the maintenance of intracellular bonds and the intracellular matrix. By introducing EDTA or EGTA, which binds these cations, the intercellular bonds are disrupted, thereby allowing for dissociation of the tissue structures.

Lastly, mechanical dissociation requires cutting, scraping or scratching the tissue into small pieces, then the minced-up tissue is washed in medium in order to separate the cells from the tissue and sometimes gentle agitation is also used to help loosen the cells. In other embodiments, mechanical dissociation may involve homogenizing a sample, as described further herein.

In some embodiments, cells within the homogenized sample, or filtered homogenized sample, are lysed to release cellular components. For example, cells may be lysed using a French press or similar type of lysis apparatus, microfluidizers, grinding, milling, chemical or enzymatic lysis (including those described above), and/or using other techniques known in the art. In some embodiments, membrane lipids and proteins (include histones) are removed from the sample containing the cellular components (e.g. by adding surfactants or enzymes (proteases)).

Further processing of the homogenized, representative, or dissociated samples into individual nuclei requires the removal of the cell membrane. Current nuclear isolation methods for fresh cells do not require enzymes to liberate nuclei, and nuclear isolation from formalin fixed sample is not a common method. To efficiently isolate individual nuclei, while maintaining cytoskeletal markers that would enable differentiation between normal and tumor nuclei, enzymes (e.g. pronase, proteinase K, pepsin, trypsin, Accumax, collagenase H) may be used to reveal nuclei without undue damage that would liberate DNA from the treated nuclei. Particular methods of isolating nuclei from a homogenate or a representative sample are disclosed in co-pending PCT Application No. PCT/US2016/060861, the disclosure of which is hereby incorporated by reference herein in its entirety.

Sorting of Separated Cellular Particles

Following the separation of cellular particles (such as cells or nuclei) and/or small tissue aggregates, from a tissue sample (step 100) or, more specifically, the homogenization (step 200) and dissociation (step 210) of cellular particles and/or small tissue aggregates, the cellular particles and/or small tissue aggregates are sorted (step 110 or 220). In some embodiments, the sorting of the separated cellular particles and/or small tissue aggregates, occurs without the need for staining the cellular particles and/or small tissue aggregates.

In some embodiments, the cellular particles and/or small tissue aggregates are sorted into two or more populations based on the size of the cellular particles and/or small tissue aggregates. In some embodiments, the cellular particles and/or small tissue aggregates are sorted based upon their hydrodynamic size. For example, it is believed that tumor cells, nuclei, and/or tumor tissue aggregates are generally larger in size than normal cells, normal nuclei, and normal tissue aggregates, respectively. As such, it is believed that a sorting device may be used to reproducibly distribute a heterogeneous sample comprising both tumor cells or nuclei and normal cells or nuclei into at least two discrete populations (step 220) prior to downstream processing or analysis (step 230).

Applicants have discovered that dissociated, fixed tumor tissues reproducibly distribute into particles of two different size distributions (see Examples herein). In fact, upon staining samples for a fluorescent tumor marker and FACS sorting "tumor" and "normal" populations, Applicants discovered that there exist a significant and reproducible size difference between tumor and normal material (both cells and nuclei). Applicants have shown that cellular particles in the smaller fraction are negative for the tumor marker and contain diploid DNA, while cellular particles in the larger fraction are positive for the tumor marker and have a higher DNA content, indicative of cycling or aneuploid cells (confirming that they are likely tumor cells) (see Examples herein).

In some embodiments, it is believed that normal cells have a size ranging from between about 4 μm to about 12 μm depending, of course, on the type of cell or the tissue in which the cell originated, and whether the tissue from which the cell originated was preserved, e.g. formalin-fixed a paraffin embedded. In some embodiments, normal cells isolated from formalin-fixed tissues have a size which ranges from between about 5 μm to about 12 μm. In yet other embodiments, normal cells from fixed tissue have a size which is less than 12 μm.

In some embodiments, it is believed that tumor cells have a size ranging from between about 9 μm to about 100 μm depending, of course, on the type of cell or the tissue in which the cell originated, and whether the tissue from which the cell originated was preserved, e.g. formalin-fixed a paraffin embedded. In some embodiments, tumor cells isolated from fixed tissue have a size which ranges from between about 9 μm to about 20 μm. In other embodiments, tumor cells isolated from fixed tissue have a size which ranges from between about 9 μm to about 50 μm. In other embodiments, tumor isolated from fixed tissue cells have a size which ranges from between about 12 μm to about 25 μm. In yet other embodiments, tumors cells isolated from fixed tissue have a size which is greater than 12 μm.

In some embodiments, a tumor cell may have an average size that is at least about 30% larger than a corresponding normal cell. In other embodiments, a tumor cell may have an average size that is at least about 35% larger than a corresponding normal cell. In yet other embodiments, a tumor cell may have an average size that is at least about 40% larger than a corresponding normal cell. In further embodiments, a tumor cell may have an average size that is at least about 45% larger than a corresponding normal cell. In yet further embodiments, a tumor cell may have an average size that is at least about 50% larger than a corresponding normal cell. In even further embodiments, a tumor cell may have an average size that is at least about 55% larger than a corresponding normal cell. In even further embodiments, a tumor cell may have an average size that is at least about 70% larger than a corresponding normal cell. In even further embodiments, a tumor cell may have an average size that is at least about 90% larger than a corresponding normal cell.

In even further embodiments, a tumor cell may have an average size that is at least about 100% larger than a corresponding normal cell.

It is believed that tumor and normal cells isolated from fresh solid tumor tissues would have different relative sizes similar to fixed tissue. Freshly dissociated tissue refers to tissue that has been removed from the body and processed to single cells within a predetermined time period, for example tissue that has been removed and processed within 24 hours, within 18 hours, within 12 hours, or within 6 hours, without being placed in formalin and prior to any fixation process, resulting in predominantly intact, viable cells. Following dissociation, cells derived from the fresh tissue can either be cultured or briefly fixed (typically in about 3% paraformaldehyde) prior to analysis. Dissociation of fresh tissue can be achieved using a number of previously described protocols or commercially available kits, typically involving both mechanical and enzymatic steps (such as disclosed herein In some embodiments, it is believed that normal nuclei isolated from fixed tissue have a size ranging from between about 4.5 µm to about 9 µm depending, of course, on the type of cell or the tissue in which the nuclei originated, and whether the tissue from which the nuclei originated was preserved, e.g. formalin-fixed a paraffin embedded. In other embodiments, normal nuclei have a size which ranges from between about 5 µm to about 8.5 µm. In yet other embodiments, normal cells have a size which is less than 8.5 µm. It is anticipated that normal nuclei isolated from fresh tissue may have a size range that is similar or slightly larger than those isolated from fixed tissue.

It is believed that tumor nuclei isolated from fixed tissue have a size ranging from between about 7.5 µm to about 20 µm depending, of course, on the type of cell or the tissue in which the nuclei originated, and whether the tissue from which the nuclei originated was preserved, e.g. formalin-fixed a paraffin embedded. In other embodiments, tumor nuclei have a size which ranges from between about 8.5 µm to about 20 µm. In other embodiments, tumor nuclei have a size which ranges from between about 9 µm to about 18 µm. In other embodiments, tumor nuclei have a size which ranges from between about 9.5 µm to about 15 µm. In yet other embodiments, tumors cells have a size which is greater than about 8.5 µm.

In some embodiments, dissociation may yield singlet normal cells that dissociate more readily (e.g. immune cells) and produce aggregates of tumor cells that are less readily dissociated. In some embodiments, tumor cell aggregates may be distinguished from singlet normal cells by size. In some embodiments, dissociated fixed normal cells range in size from about 4 to about 8.5 µm. Tumor cell aggregates could consist of about 2 to greater than 100 cells, depending upon the properties of the tissue and dissociation methods used. Tumor cell aggregates could be composed of groups of cells collectively larger than about 20 µm, about 50 µm, about 100 µm, about 300 µm, or about 500 µm.

In some embodiments, the cellular particles (e.g. cells or cell nuclei) having a first size range are sorted into a first population, and the cellular particles (e.g. cells or cell nuclei) having a second size range are sorted into a second population, wherein the first population comprises at most 30% of cellular particles having the second size range. In some embodiments, the first population comprises at most 25% of cellular particles having the second size range. In some embodiments, the first population comprises at most 20% of cellular particles having the second size range. In some embodiments, the first population comprises at most 15% of cellular particles having the second size range. In some embodiments, the first population comprises at most 10% of cellular particles having the second size range. In some embodiments, the first population comprises at most 7.5% of cellular particles having the second size range. In some embodiments, the first population comprises at most 5% of cellular particles having the second size range. In some embodiments, the first population comprises at most 2.5% of cellular particles having the second size range. In some embodiments, the first population comprises at most 1% of cellular particles having the second size range.

Sorting Devices

In some embodiments, the sorting device is an instrument or apparatus which directs cells or nuclei having a first size in a first direction, and cells or nuclei having a second size in a second direction, without first staining the cells or nuclei or labeling them with any agent (e.g. magnetic particles, etc.).

In some embodiments, the sorting device is a microfluidic device. Microfluidics is one technique where sorting of cells and/or nuclei according to size may be accomplished. Accordingly, in some embodiments, sorting is achieved using a microfluidics-based technique. In some embodiments, sorting is achieved using a microfluidics device, such as a disposable microfluidics device. Non-limiting examples of microfluidic techniques are described herein. Additional examples of microfluidic techniques which may be implemented as part of the present method are disclosed in the following references, each of which are incorporated by reference herein in their entireties: (i) C. Wyatt Shields IV, Dr. Catherine D. Reyes, and Prof. Gabriel P. López, Microfluidic Cell Sorting: A Review of the Advances in the Separation of Cells from Debulking to Rare Cell Isolation, Lab Chip. 2015 Feb. 16; 15(5): 1230-1249; and (ii) P. Sajeesh and Ashis Kumar Sen, Particle Separation and Sorting in Microfluidic Devices: A Review, Microfluid Nanofluid (2014) 17:1-52.

In some embodiments, the sorting device is a device employing an array of a network of gaps, wherein a fluid passing through a gap is divided unequally into subsequent gaps. By "gap" it is meant an opening through which fluids or particles can flow. For example, a gap can be a space between two obstacles wherein fluids can flow, or a hydrophilic pattern on an otherwise hydrophobic surface wherein aqueous fluids are confined. The array includes a network of gaps arranged such that fluid passing through a gap is divided unequally, even though the gaps may be identical in dimensions. In some embodiments, the method utilizes a flow that carries cells to be separated through the array of gaps. In some embodiments, the flow is aligned at a small angle (flow angle) with respect to a line-of-sight of the array. In some embodiments, cells or nuclei having a hydrodynamic size larger than a critical size migrate along the line-of-sight, i.e., laterally, through the array, whereas those having a hydrodynamic size smaller than the critical size follow the average flow direction. Without wishing to be bound by any particular theory, it is believed that flow in the device occurs under laminar flow conditions. Devices of the present disclosure are optionally configured as continuous-flow devices. In some embodiments, the critical size is at least 8.5 µm. In other embodiments, the critical size is at least 9 µm. In yet other embodiments, the critical size is at least 10 µm. In further embodiments, the critical size is at least 12 µm. Of course, the skilled artisan will appreciate that the critical size may be modified to accommodate different types of cells, cells from different origins, and cells that are fresh as opposed to fixed. One skilled in the art will also appreciate that the critical size may be increased or decreased to improve the purity or yield of the collected population.

In some embodiments, separation of cells by a sorting device may be based on differential rolling characteristics of at least one target cell as compared to non-target cells. In certain embodiments, target cells are cells that share a common characteristic that is recognized by cell adhesion entities coated on the three-dimensional structure(s). In general, target cells are diverted away from the direction of bulk flow by cell rolling, whereas non-target cells that are not recognized by cell adhesion entities do not roll and are not diverted from the direction of bulk flow. While the present disclosure refers generally to the diverted cells as "target cells" it will be appreciated that this is an arbitrary designation and that, in certain embodiments, separation of cells may be performed in a negative selection mode whereby the real "target cells" are in fact the cells that are not diverted.

The skilled artisan will appreciate that multiple sorting devices may be used in tandem, e.g. the cells may be passed through first and second devices, both employing deterministic lateral displacement, or the cells may be passed through a first device utilizing deterministic lateral displacement and a second device employing a different microfluidic technique. In some embodiments, the first sorting device sorts the input material into first and second populations, and the second sorting device refines the sorting, e.g. sorting the first population into first and second subpopulations. In some embodiments, the sorting device may be coupled with a secondary enrichment technique, the secondary enrichment technique optionally requiring the staining or labeling of the separated cells or nuclei (e.g. flow cytometry, magnetic separation).

Deterministic Lateral Displacement

Figure 11:
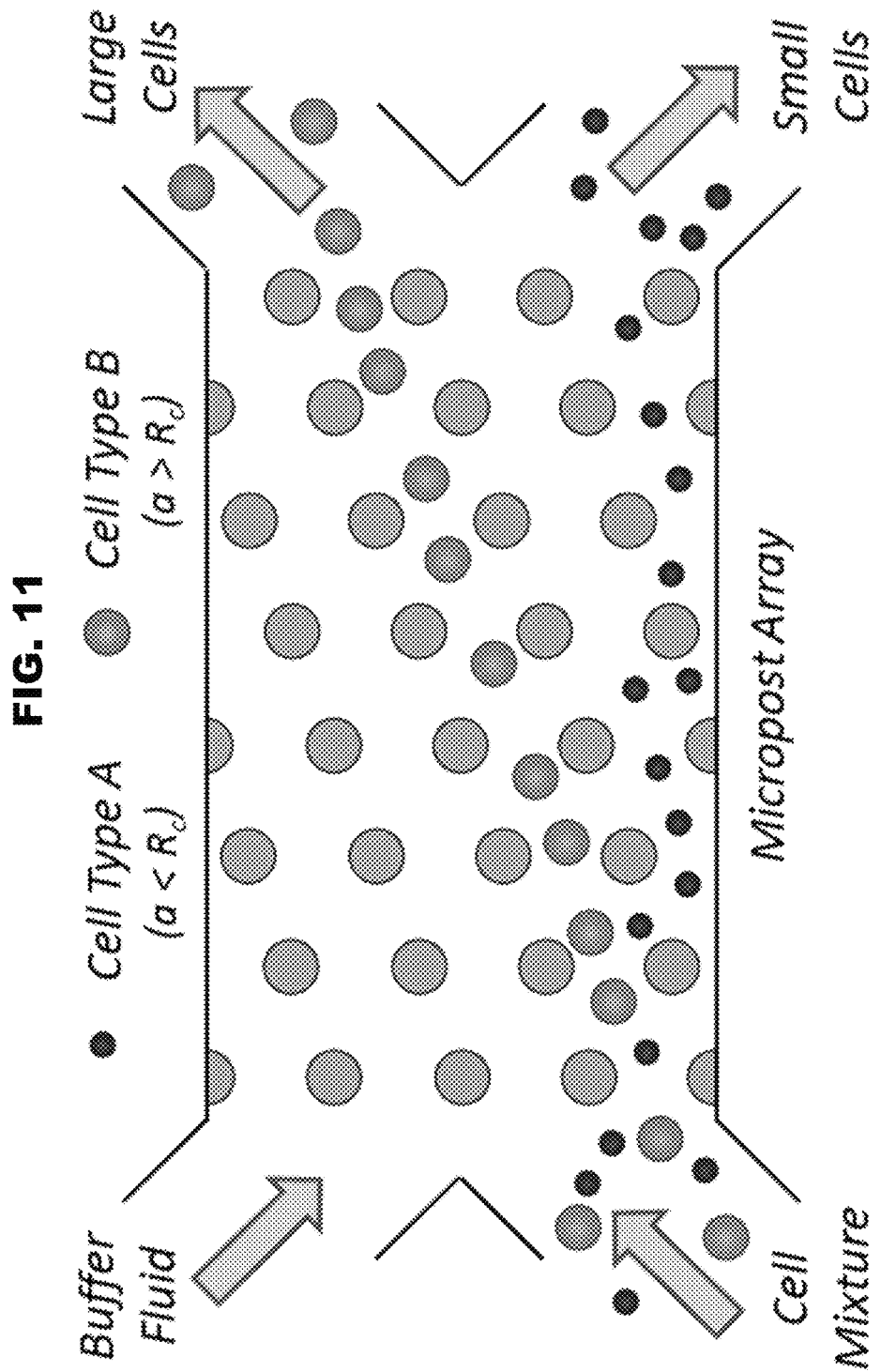
FIG. 11 illustrates cell sorting by deterministic lateral displacement. Large cells (depicted in blue) migrate away from the small cells (depicted in red) in the initial streamline due to the engineered size and spacing of the microposts in the microfluidic channel.

Deterministic lateral displacement (DLD) is a steric method of continuous separation that makes use of asymmetric bifurcation of laminar flow around obstacles (see FIG. 11). For example, particles (here cells or nuclei) moving through an array of obstacles with gaps larger than the particle size select their path deterministically on the basis of their size and deformability. It is believed that particles of given size and deformability follow an equivalent migration path leading to an efficient separation method.

In general, a critical diameter for separation is described by $Dc=2\eta d\epsilon$, where $\eta$ is a unit-less parameter, d is the distance between the edges of adjacent obstacles and $\epsilon$ is the row shift fraction (see, for example, Huang et al., Science 2004, 304, (5673), 987-990). $\epsilon$ is defined as $\epsilon=\Delta d/W$, where W is the distance from center to center of two adjacent obstacles in the same row and $\Delta d$ is the lateral shift between two adjacent obstacles in successive rows. Particles (e.g., cells) that are larger than Dc are forced to move at an angle relative to the direction of bulk flow by repetitively bumping against the obstacles. The repetitive bumping can be advantageously used in the context of the present disclosure to promote interactions between cells and surfaces of the obstacles that are coated with a cell adhesion entity.

Obstacles in the array are typically protrusions from an internal surface (e.g., lower surface, upper surface, side walls or combination thereof) of a sorting channel. In certain embodiments, protrusions span the distance between the lower and upper surface of a sorting channel. An obstacle may have any shape, e.g., without limitation, squares, rectangles, triangles, trapezoids, hexagons, tear-drops, polygons, ellipses, circles, arcs, waves, and/or combinations thereof.

In some embodiments, the device is designed for use with cells that have an average diameter D and the critical diameter Dc is designed to be less than D. In some embodiments, a sorting channel may have a critical diameter Dc that is less than about 7 µm, about 7.5 µm, about 8 µm, about 8.5 µm, about 9 µm, about 10 µm, or less than about 12 µm. In some embodiments, a sorting channel may have a critical diameter Dc that is greater than about 7 µm, about 7.5 µm, about 8 µm, about 8.5 µm, about 9 µm, about 10 µm, or greater than about 12 µm. In certain embodiments, a sorting channel may have a critical diameter Dc in a range that is between any two of these values. For example, in certain embodiments, a sorting channel may have a critical diameter Dc in the range of about 6 µm to about 8.5 µm, e.g., about 7 µm to about 9 µm, about 9 µm to about 12 µm, etc. One skilled in the art will appreciate that the critical diameter may be increased or decreased to improve the purity or yield of the collected population.

Hydrodynamic Focusing

In some embodiments, a sorting channel utilizes hydrodynamic focusing to separate cells. Generally, a sorting channel that relies on hydrodynamic focusing will comprise a constriction region and an expansion region. Hydrodynamic focusing works by forcing cells to line up single file along the longitudinal direction by covering a sample flow with a sheath flow. In certain embodiments of the present disclosure, the position of a cell in the expansion region (in the absence of cell rolling) can be determined by $Wp=\{W2/W1\}d$, where d is the diameter of the cell, W1 is the width of the constriction region and W2 is the width of the expansion region. Typically, the sheath flow forces cells to contact with a side wall of the constriction region and in the context of the present disclosure this can be used to promote interactions between cells and a surface of the side wall that is coated with a cell adhesion entity. As shown in FIG. 13, the presence of a coating can cause a cell that would otherwise reach the expansion region at position Wp to roll along the side wall of the expansion region and exit at a different position in the expansion region. It will be appreciated that the specific dimensions W1 and W2 as well as the flow velocities of the sheath and sample flows can be adjusted depending on the nature of the cells that are being sorted and the nature of the coating.

Acoustophoresis

Label-free acoustofluidic systems generally sort cells based on differences in their size. This method of cell sorting relies on the initial placement of cells in streamlines away from the pressure node(s) for their rapid displacement to the node(s) upon actuation of the device, thereby separating cells of disparate size or acoustic properties.

In some embodiments, hydrodynamic forces are used to direct cells or nuclei to a side walls of an acoustofluidic device whereupon they migrate toward a node of an acoustic standing wave at a rate proportional to their volume. It is believed that larger cells experience greater forces in an acoustic standing wave, and thus respond faster to the radiation forces, thus directing larger cells to the center outlet (e.g. the node) and smaller cells to the side outlets. Acoustophoreetic methods are further described at least by (i) Petersson F, Nilsson A, Holm C, Jonsson H, Laurell T. The Analyst. 2004; 129:938-943. [PubMed: 15457327]; (ii) Petersson F, Nilsson A, Holm C, Jonsson H, Laurell T. Lab Chip. 2005; 5:20-22. [PubMed: 15616735]; (iii) Petersson F, Aberg L, Sward-Nilsson A M, Laurell T. Analytical Chemistry. 2007; 79:5117-5123. [PubMed: 17569501]; (iv) Dykes J, Lenshof A, Astrand-Grundstrom I, Laurell T, Scheding S. PloS one. 2011; 6:e23074. [PubMed: 21857996]; (v)

Augustsson P, Magnusson C, Nordin M, Lilja H, Laurell T. Anal. Chem. 2012; 84:7954-7962. [PubMed: 22897670]; (vi) Yang A H, Soh H T. Analytical chemistry. 2012; 84:10756-10762. [PubMed: 23157478]; and (vii) Fong E J, Johnston A C, Notton T, Jung S Y, Rose K A, Weinberger L S, Shusteff M. The Analyst. 2014; 139:1192-1200. [PubMed: 24448925], the disclosure of which are hereby incorporated by reference herein in their entireties.

Inertial Focusing in Curved Channels

Inertial forces can result in the induced migration of cells or particles across streamlines in laminar flow streams. Typically, inertial forces emanate from boundary effects of fluid flow adjacent to the walls of a microfluidic channel, causing lift. Inertial focusing in curved channels refers to a subset of distinct phenomenological techniques for cell fractionation, which includes the use of serpentine or Archimedean spiral patterns for cell ordering and sorting.

Devices and techniques for implementing inertial focusing in curved channels are further described in at least the following references, the disclosure of which are hereby incorporated by reference herein in their entireties: (i) Di Carlo D, Edd J F, Irimia D, Tompkins R G, Toner M. Analytical Chemistry. 2008; 80:2204-2211. [PubMed: 18275222]; (ii) Oakey J, Applegate R W Jr, Arellano E, Di Carlo D, Graves S W, Toner M. Analytical chemistry. 2010; 82:3862-3867. [PubMed: 20373755]; (iii) Russom A, Gupta A K, Nagrath S, Di Carlo D, Edd J F, Toner M. New J Phys. 2009; 11:75025; (iv) Kuntaegowdanahalli S S, Bhagat A A, Kumar G, Papautsky I. Lab Chip. 2009; 9:2973-2980. [PubMed: 19789752]; (v) Hou H W, Warkiani M E, Khoo B L, Li Z R, Soo R A, Tan D S-W, Lim W-T, Han J, Bhagat A A S, Lim C T. Scientific Reports. 2013; 3:1-8; (vi) Nivedita N, Papautsky I. Biomicrofluidics. 2013; 7:54101. [PubMed: 24404064]; and (v) Guan G, Wu L, Bhagat A A, Li Z, Chen P C, Chao S, Ong C J, Han J. Sci Rep. 2013; 3:1475. [PubMed: 23502529].

Pinched Flow and Hydrodynamic Spreading

Figure 10:
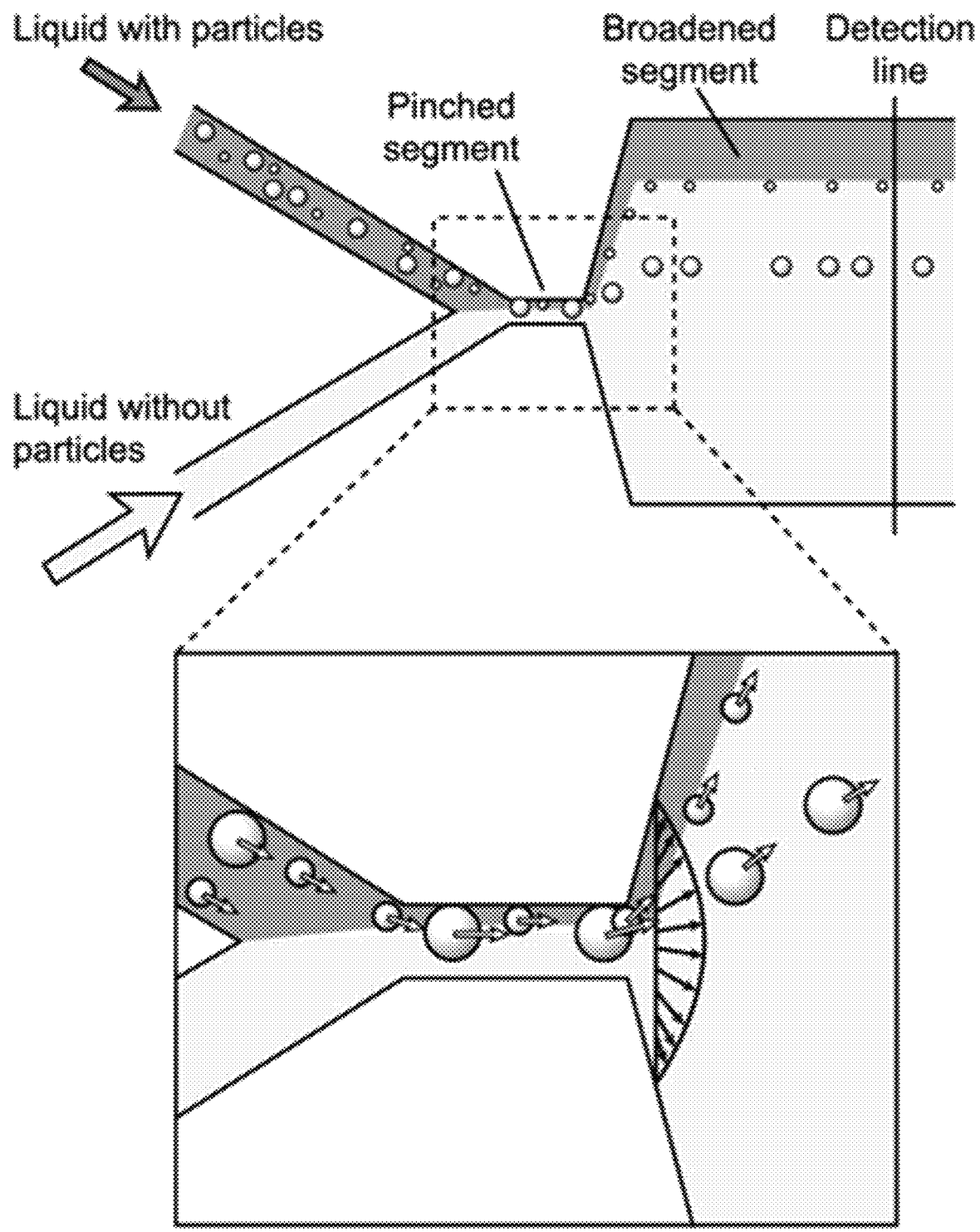
FIG. 10 illustrates cell sorting by pinched flow fractionation. In particular, the figure shows that a pinched segment where cells are first pushed against the wall, and then separated by size upon broadening of the microfluidic channel. The enlarged section of the figure further illustrates that cells are aligned in the pinched segment of the channel and follow separate streamlines for sorting by size after exiting the pinched segment.

In addition to curved channels (noted above), inertial forces can play a critical role in straight channels. Pinched flow fractionation and hydrodynamic spreading are two examples where inertial forces play a role in the ordering of cells for subsequent sorting. Pinched flow fractionation occurs when a flow stream of cells is pinched by a narrow channel cross section such that cells are constrained and aligned against a side wall and subsequently separate by size once the channel broadens due to the laminar flow profile (see FIG. 10). This alignment effect is typically enhanced by sheath fluid, which pushes cells against a wall such that the center of the larger cells are farther from the wall surface than the center of smaller cells, thus giving cells of different sizes slightly different flow trajectory upon broadening of the channel. This method for sorting has been expanded by the addition of multiple asymmetric outlets for better hydrodynamic control as well as by the spatial reorientation of the microfluidic device for gravitationally enhanced separation between cell populations of different size and mass.

Devices and techniques for implementing pinched flow and hydrodynamic spreading are further described in at least the following references, the disclosure of which are hereby incorporated by reference herein in their entireties: (i) Di Carlo D. Lab Chip. 2009; 9:3038-3046. [PubMed: 19823716]; (ii) Di Carlo D, Irimia D, Tompkins R G, Toner M. Proceedings of the National Academy of Sciences of the United States of America. 2007; 104:18892-18897. [PubMed: 18025477]; (iii) Di Carlo D, Edd J F, Irimia D, Tompkins R G, Toner M. Analytical Chemistry. 2008; 80:2204-2211. [PubMed: 18275222]; (iv) Oakey J, Applegate R W Jr, Arellano E, Di Carlo D, Graves S W, Toner M. Analytical chemistry. 2010; 82:3862-3867. [PubMed: 20373755]; (v) Russom A, Gupta A K, Nagrath S, Di Carlo D, Edd J F, Toner M. New J Phys. 2009; 11:75025; (vi) Kuntaegowdanahalli S S, Bhagat A A, Kumar G, Papautsky I. Lab Chip. 2009; 9:2973-2980. [PubMed: 19789752]; (vii) Hou H W, Warkiani M E, Khoo B L, Li Z R, Soo R A, Tan D S-W, Lim W-T, Han J, Bhagat A A S, Lim C T. Scientific Reports. 2013; 3:1-8; (viii) Nivedita N, Papautsky I. Biomicrofluidics. 2013; 7:54101. [PubMed: 24404064]; (ix) Guan G, Wu L, Bhagat A A, Li Z, Chen P C, Chao S, Ong C J, Han J. Sci Rep. 2013; 3:1475. [PubMed: 23502529]; (x) Warkiani M E, Guan G, Luan K B, Lee W C, Bhagat A A, Chaudhuri P K, Tan D S, Lim W T, Lee S C, Chen P C, Lim C T, Han J. Lab Chip. 2014; 14:128-137. [PubMed: 23949794]; (xi) Parichehreh V, Medepallai K, Babbarwal K, Sethu P. Lab Chip. 2013; 13:892-900. [PubMed: 23307172]; and (xii) Yamada M, Nakashima M, Seki M. Analytical Chemistry. 2004; 76:5465-5471. [PubMed: 15362908].

Hydrophoretic Filtration

Ridge-induced hydrophoretic filtration relies on the formation of a lateral pressure gradient within a microfluidic channel due to flow-altering micropatterns. A successive array of slanted obstacles on the microchannel floor and ceiling induces a pressure gradient across the width of the channel to focus cells to precise locations within the generated local pressure field according to type and then separates those cells. Devices and techniques for hydrophoretic filtration are further described in at least the following references, the disclosure of which are hereby incorporated by reference herein in their entireties: (i) Choi S, Song S, Choi C, Park J K. Lab Chip. 2007; 7:1532-1538. [PubMed: 17960282]; (ii) Hsu C H, Di Carlo D, Chen C, Irimia D, Toner M. Lab Chip. 2008; 8:2128-2134. [PubMed: 19023476]; (iii) Stott S L, Hsu C H, Tsukrov D I, Yu M, Miyamoto D T, Waltman B A, Rothenberg S M, Shah A M, Smas M E, Korir G K, Floyd F P Jr, Gilman A J, Lord J B, Winokur D, Springer S, Irimia D, Nagrath S, Sequist L V, Lee R J, Isselbacher K J, Maheswaran S, Haber D A, Toner M. Proceedings of the National Academy of Sciences of the United States of America. 2010; 107:18392-18397. [PubMed: 20930119]; (iv) Sollier E, Go D E, Che J, Gossett D R, O'Byrne S, Weaver W M, Kummer N, Rettig M, Goldman J, Nickols N, McCloskey S, Kulkarni R P, Di Carlo D. Lab Chip. 2014; 14:63-77. [PubMed: 24061411]; and (v) Hyun K A, Kwon K, Han H, Kim S I, Jung H I. Biosensors & bioelectronics. 2013; 40:206-212. [PubMed: 22857995].

Size Exclusion Filtration

Instead of engineering the size and pattern of uniformly spaced posts to sort cells, size exclusion filtration refers to the use of posts with tiered (i.e., decreasing) spacing as a function of distance for sorting cells in a non-binary fashion. Size exclusion filters consist of a series of linear arrays of pillars that selectively group cells by size and shape.

Cross-Flow Filtration

The filtration of cell-containing fluids is one of the earliest methods used to fractionate cell populations. Examples of these filters include weir filters, which contain large barriers to trap large cells, pillar filters, which contain a row of same-sized microposts to trap large cells, and membrane filters, which contain an array of pores on the floor or ceiling to trap large cells.

Cross-flow filtration, sometimes referred to as tangential flow filtration, uses an array of lateral slits aligned in the direction of flow to fractionate cell populations by size. Without wishing to be bound by any particular theory, it is believed that this method of filtration is a major advancement over early types of filters such as weir, pillar, and membrane because of their decreased likelihood for clogging because the behave more like a sieve than a dead-end filter.

Hydrodynamic Filtration

Figure 12:
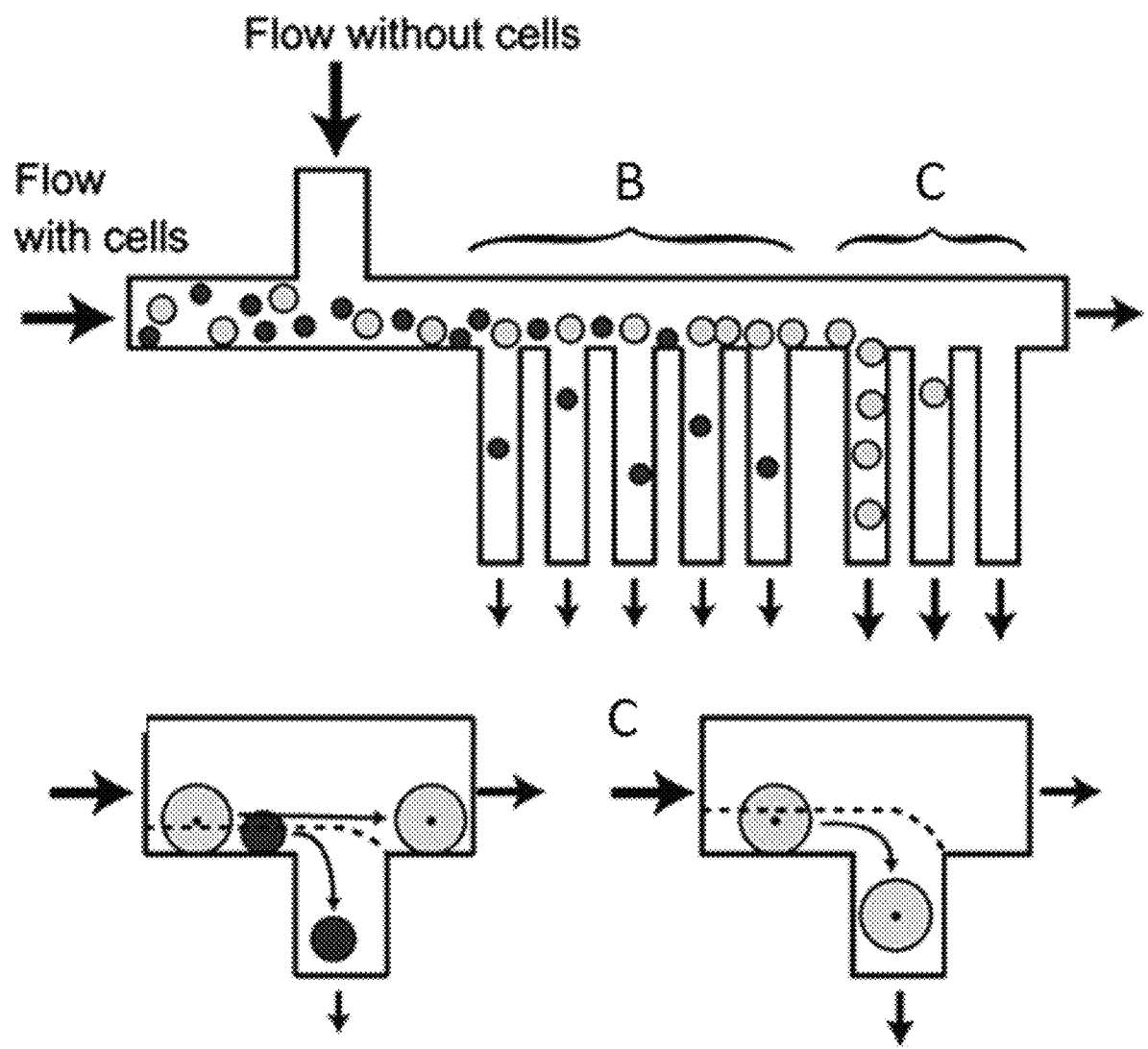
FIG. 12 illustrates cell sorting by hydrodynamic filtration. Step A) Cells are injected into the microfluidic device and are pushed toward the outlets. Step B) Small cells exit out of the proximal branches whereas, in Step C) large cells exit out of the distal branches.

In hydrodynamic filtration, cells are separated by multiple branched outlets, whereby the fluid draining from the outlets pulls cells from the walls of the main channel at rates that scale according to their size (see FIG. 12). Smaller cells exit the proximal outlets because their center is closer to the wall of the microfluidic channel, enabling their controlled shunting from larger cells.

Figure 13A:
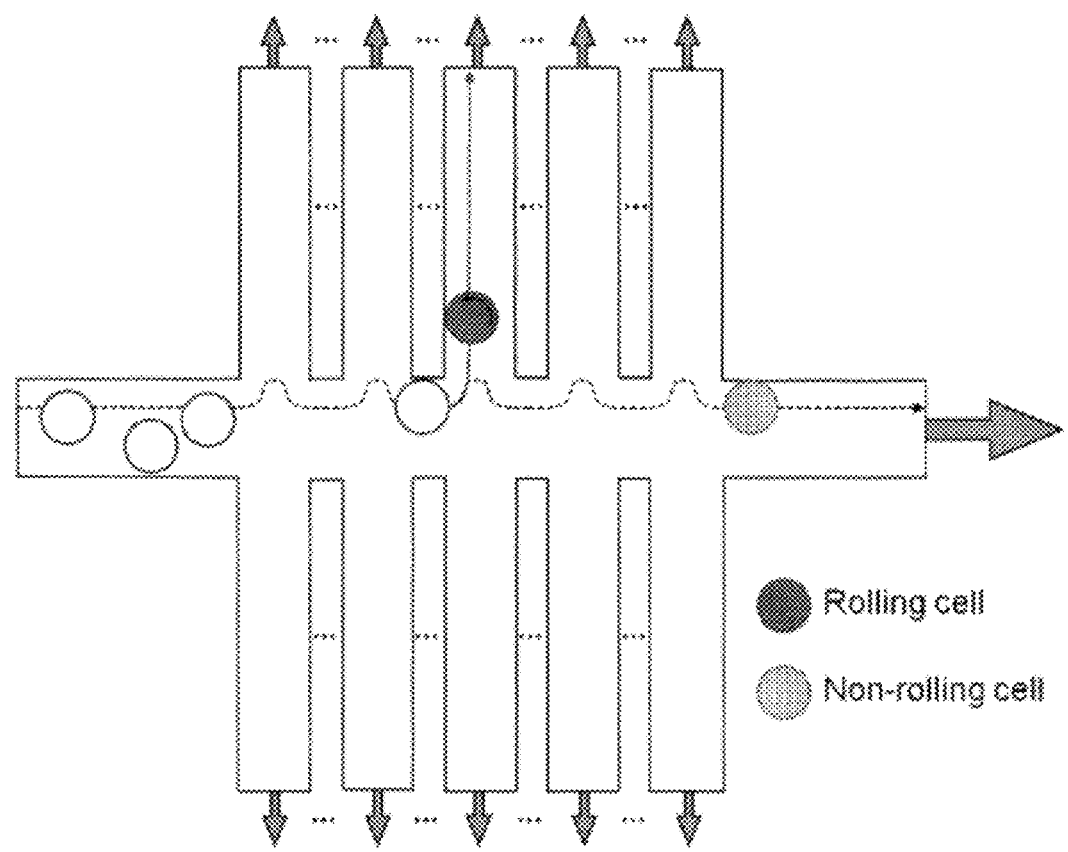
FIG. 13A illustrates an approach to geometry-directed rolling in a hydrodynamic filtration device that includes a main channel and multiple side channels.
Figure 13B:
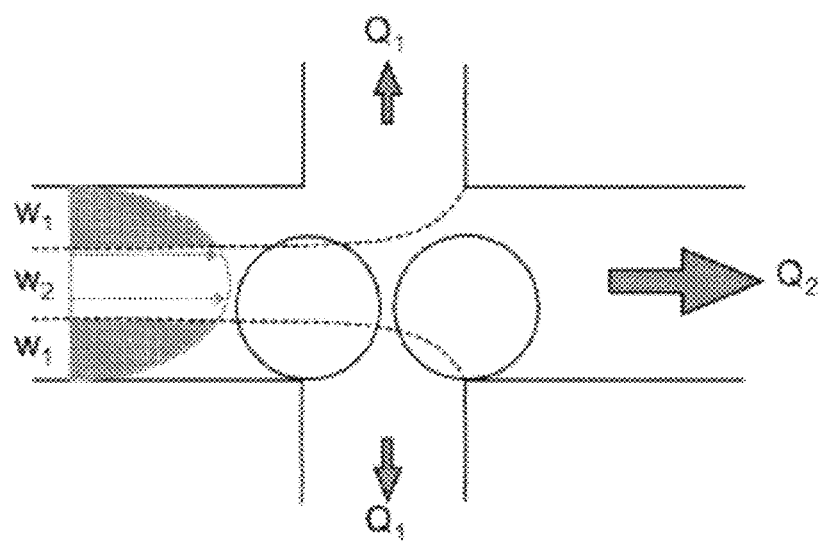
FIG. 13B provides a close-up view of the flow rate distribution at a branch between the main channel and a side channel.
Figure 13C:
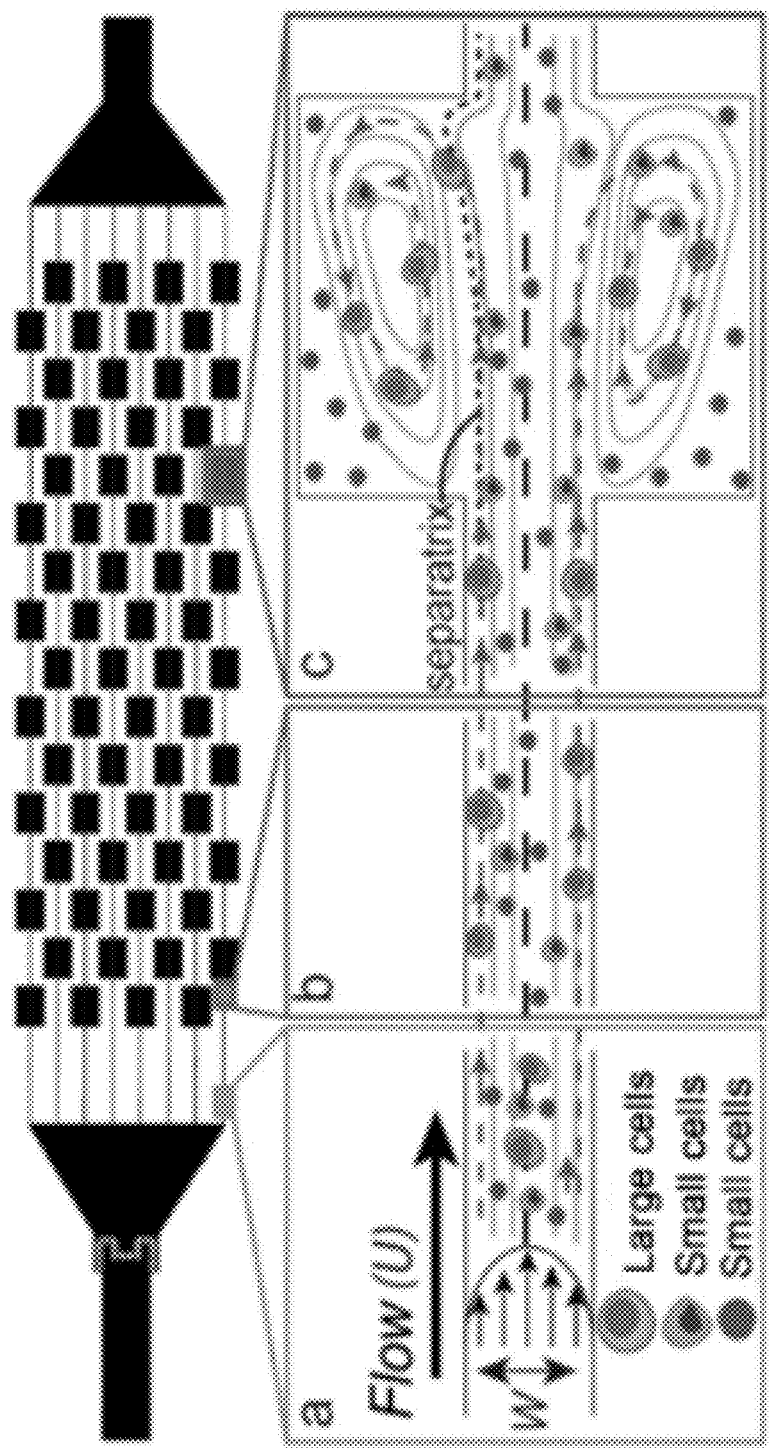
FIG. 13C illustrates another microfluidic device contemplated for use within the presently disclosed methods. The Vortex HE, disclosed herein, device has 8 reservoirs in series and 8 in parallel. (Step a) Initially cells are distributed throughout the channel cross-section. (Step b) After traveling a predetermined distance, the larger cells (e.g. tumor cells) that experience higher inertial lift force migrate towards the channel walls. (Step c) The larger cells (e.g. tumor cells) located near the wall experience enough lift force to enter the reservoir and remain stably trapped, while smaller cells (e.g. normal cells) either do not enter the reservoirs or do not remain trapped and return to the main flow.

As shown in FIG. 13A, a sorting channel that relies on hydrodynamic filtration can comprise a main channel and a plurality of side channels. As shown in FIG. 13B, at a branch between the main and side channels, a flow rate ratio determines whether cells (or nuclei) continue to flow through the main channel or exit into a side channel. Generally, in the absence of cell rolling, cells that are larger than a certain width are forced to flow through the main channel, not the side channel by repetitively aligning against a sidewall. In the context of the present disclosure, such repetitive alignment can be used to promote interactions between cells and surfaces of the channel walls that are coated with a cell adhesion entity. Advantageously, cells (or nuclei) that would normally continue to travel down the main channel can be caused to roll into the side channel as shown in FIG. 13A. In certain embodiments, a sidewall of the main channel is therefore coated with a cell adhesion entity, so that a target cell can tether and roll on the sidewall.

Vortex Sorting Devices

Figure 14:
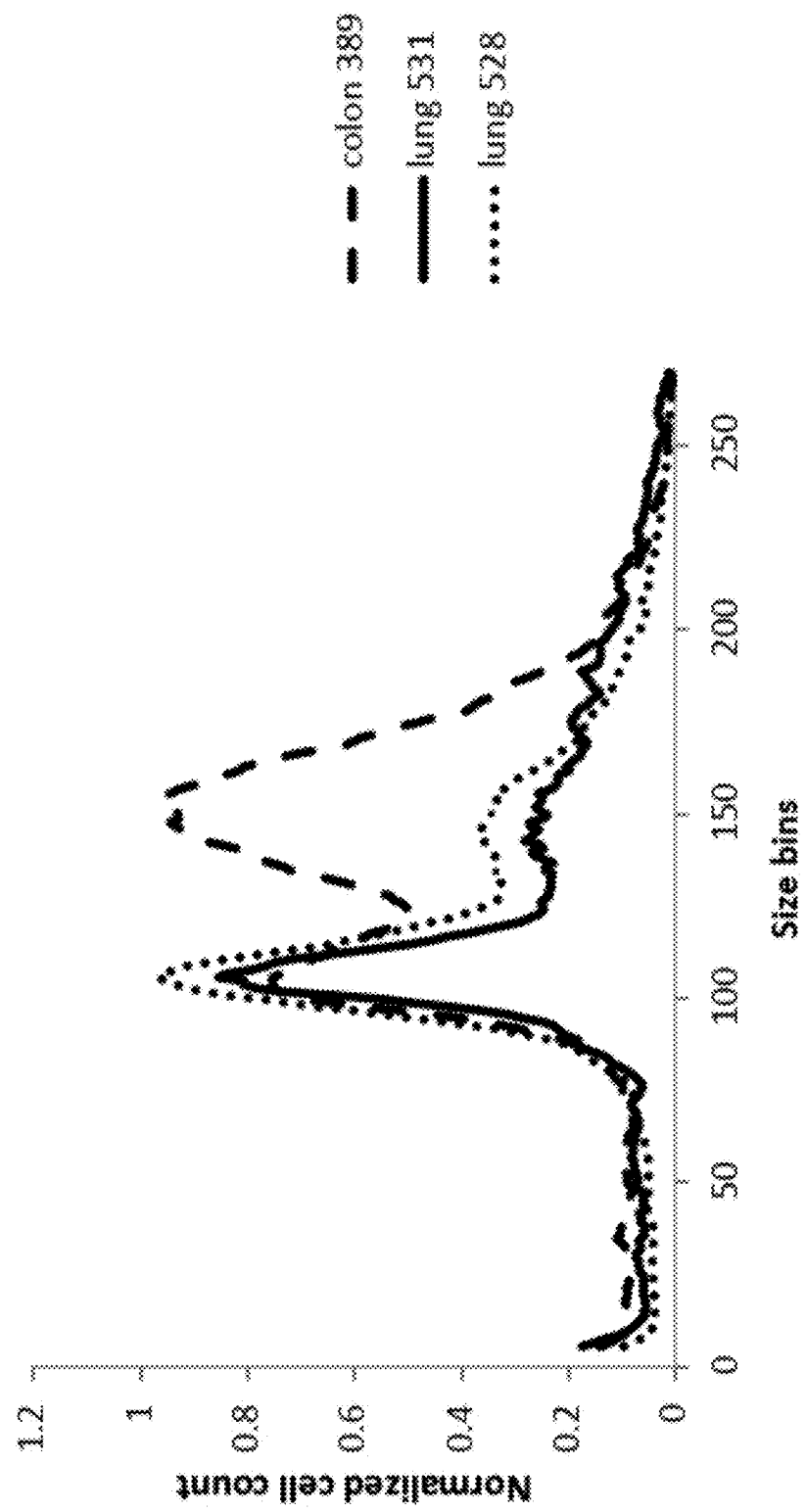
FIG. 14 illustrates the distribution of relative cell sizes for colon and lung tumor samples.
Figure 15A:
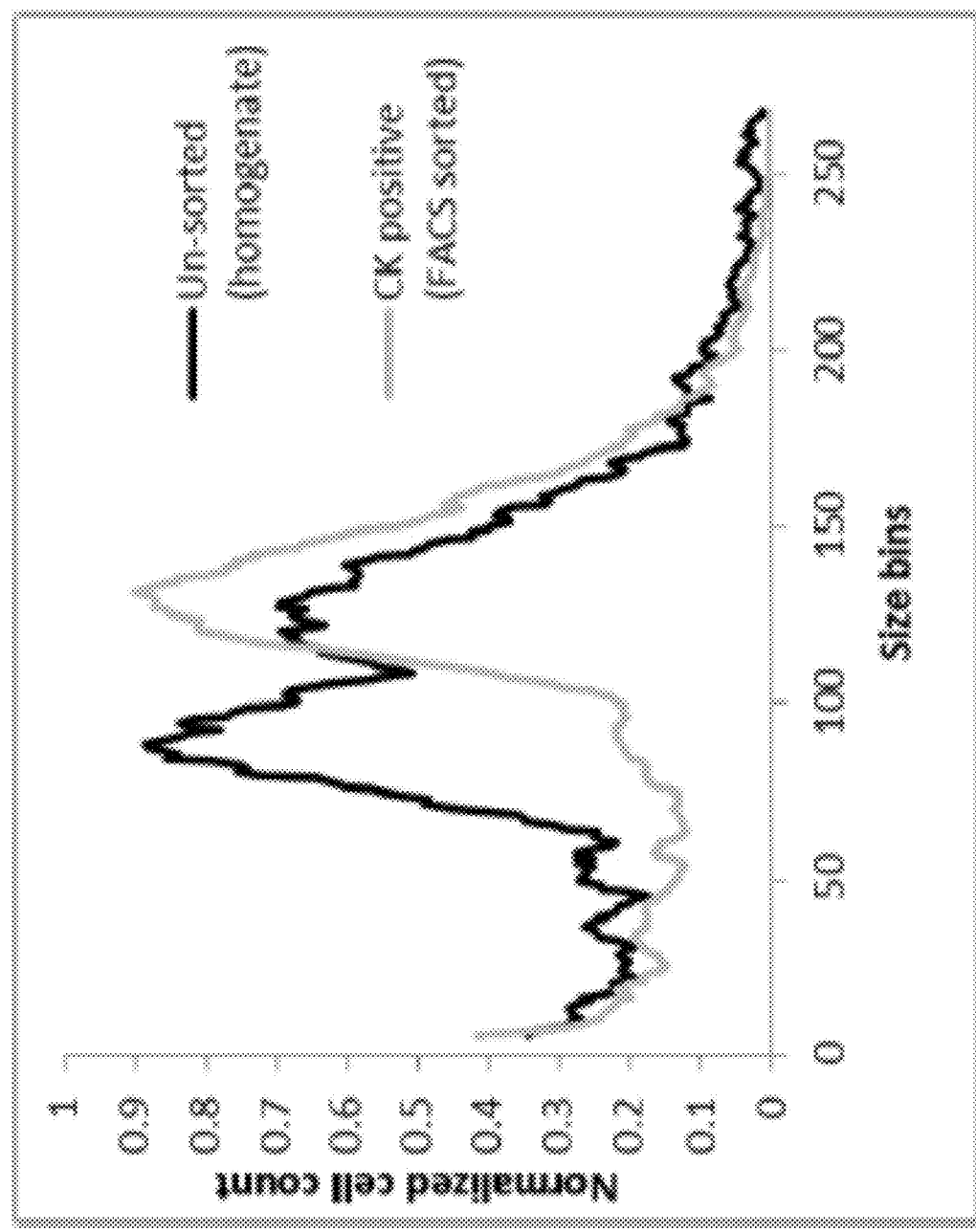
FIG. 15A illustrates sequencing data for FACS-enriched tumor samples, where large cells are identified as tumor cells based upon an increased allele fraction of clonal tumor mutations. Here, Coulter counter traces show the relative sizes of unsorted and FACS-enriched tumor nuclei from Colon adenocarcinoma.
Figure 15B:
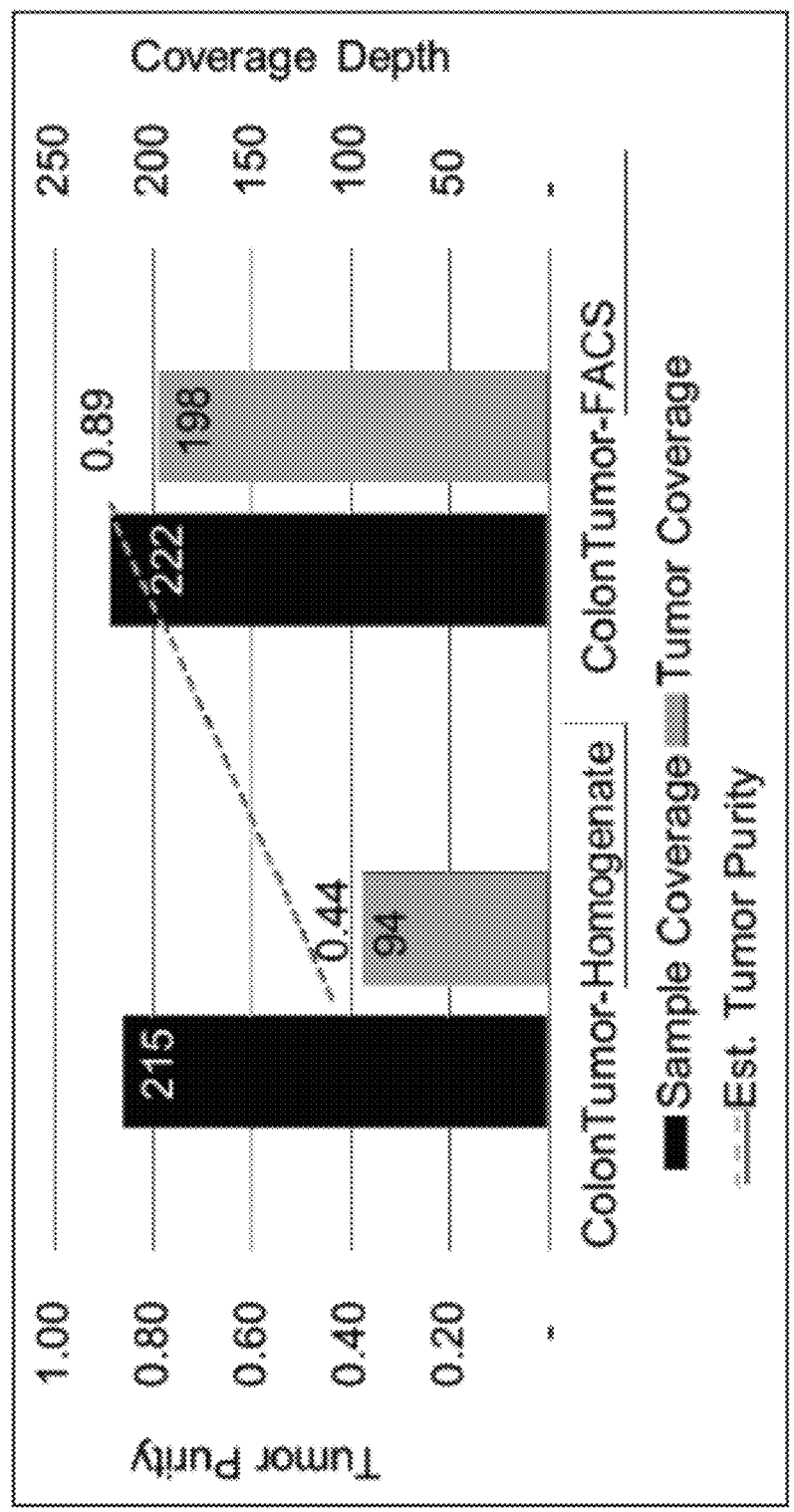
FIG. 15B illustrates sequencing data for FACS-enriched tumor samples, where large cells are identified as tumor cells based upon an increased allele fraction of clonal tumor mutations. Here, bar graphs show the sample coverage and tumor purity for sequencing data from the colon tumor representative sample homogenate (unsorted) and FACS sorted tumor nuclei (CK-positive) from (FIG. 15A).
Figure 15C:
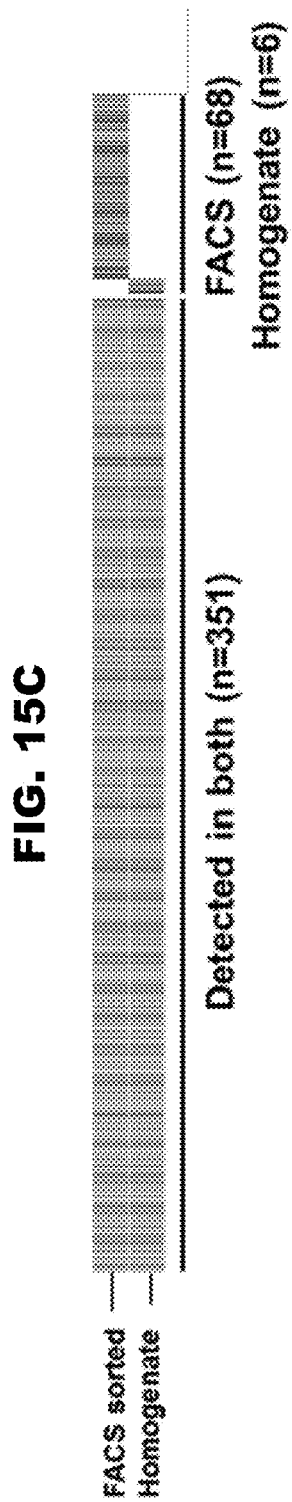
FIG. 15C illustrates sequencing data for FACS-enriched tumor samples, where large cells are identified as tumor cells based upon an increased allele fraction of clonal tumor mutations. Here, tumor mutations are detected in both the bulk representative sample homogenate and FACS sorted tumor nuclei (n=351). Additionally, some tumor mutations are detected in FACS sorted nuclei only (n=68) and homogenate only (n=6). Greater detection of tumor mutations in FACS sorted nuclei indicates increased sensitivity of genomic assay due to enrichment of tumor nuclei.

In some embodiments, the sorting device is a Vortex HE device, available from Vortex Biosciences. In some embodiments, the Vortex HE device is a microfluidic device that uses high aspect ratio microfluidic channels that are used for particle focusing followed by a plurality of expansion regions (see, FIG. 14). Without wishing to be bound by any particular theory, it is believed that particle (or cell) entry into the expansion regions that follow narrow focusing channels occurs due to the shear gradient lift force. The lift force is a balance between wall lift force pushing particles away from the wall and a transverse shear-gradient lift force determined by the fluid velocity profile around the particle. Small particles (or cells) do not experience enough shear-gradient lift force, and focus towards the middle of the channel, and do not enter the expansion regions. Increasing the lift force by decreasing the cross-sectional area of the upstream focusing channels allow smaller particles (or cells) to migrate across the mainstream and enter the expansion regions (e.g., trapped cells in expansion regions). The Vortex HE device is further described in PCT/US2016/038230, the disclosure of which is hereby incorporated by reference in its entirety. Vortex separation methods are also disclosed by Manjima Dhar, et al. "High Efficiency Vortex Trapping of Circulating Tumor Cells," Biomicrofluidics 9, 064116 (2015), the disclosure of which is hereby incorporated by reference herein in its entirety.

Additional Sorting Devices

The separated samples may also be sorted by other devices or instruments including conventional filtration (for example using cell strainers or sieve); tangential filtration; column-based filtration; and centrifugation (density-gradient centrifugation).

Microfluidic Device Manufacturing

In general, lithographic or other techniques known to those of skill in the art may be used to pattern practically any material for use as a microfluidic device. Exemplary methods for preparing suitable devices are disclosed in U.S. Pat. No. 6,197,575, U.S. Patent Publication No. 2010/0112026 and U.S. Patent Publication No. 2010/0304485 the entire contents of which are incorporated herein by reference. In various embodiments, a microfluidic device may be fabricated in whole or in part from poly(dimethyl siloxane) (PDMS), glass, silicon dioxide, or a fluoropolymer. In certain embodiments, the walls of the channel may be treated with a material to modify hydrophilicity, protein affinity, cell affinity, or any combination of these. Exemplary treatment materials, include but are not limited to, polyethylene glycols (e.g., poly(3-trimethoxysilyl)-propylmethacrylate-r-poly(ethylene glycol) methyl ether or TMSMA-r-PEGMA), organosilanes that form self-assembled monolayers, ethanol, etc.

Further Analysis

In some embodiments, the sorted or enriched populations of cells, nuclei, and/or small tissue aggregates are further analyzed (steps 120, 230, 330, 430, and 440). In some embodiments, the sorting device may be in fluidic communication with a detector, a microscope, a cell counter (e.g. a Coulter counter), a mass spectrometer, FACS, a PCR device, a RT-PCR device, a genome sequencer, an imaging system, etc. Alternatively, and in other embodiments, the sorting device may provide several populations of cells, nuclei, or small tissue aggregates that are preserved for later analysis.

Sequencing

In some embodiments, at least one of the populations of sorted cells or nuclei (step 320 or 420) is sequenced (step 330 or 440). Methods of preparing the cells and/or sorted nuclei for sequencing are disclosed, for example, in PCT/US2016/060835, the disclosure of which is hereby incorporated by reference herein in its entirety.

Sequencing (steps 330 or 440) may be performed according to any method known to those of ordinary skill in the art. In some embodiments, sequencing methods include Sanger sequencing and dye-terminator sequencing, as well as next-generation sequencing technologies such as pyrosequencing, nanopore sequencing, micropore-based sequencing, nanoball sequencing, MPSS, SOLiD, Illumina, Ion Torrent, Starlite, SMRT, tSMS, sequencing by synthesis, sequencing by ligation, mass spectrometry sequencing, polymerase sequencing, RNA polymerase (RNAP) sequencing, microscopy-based sequencing, microfluidic Sanger sequencing, microscopy-based sequencing, RNAP sequencing, tunneling currents DNA sequencing, and in vitro virus sequencing. See WO2014144478, WO2015058093, WO2014106076 and WO2013068528, each of which is hereby incorporated by reference in its entirety.

In some embodiments, sequencing (steps 330 or 440) can be performed by a number of different methods, such as by employing sequencing by synthesis technology. Sequencing by synthesis according to the prior art is defined as any sequencing method which monitors the generation of side products upon incorporation of a specific deoxynucleoside-triphosphate during the sequencing reaction (Hyman, 1988, Anal. Biochem. 174:423-436; Rhonaghi et al., 1998, Science 281:363-365). One prominent embodiment of the sequencing by synthesis reaction is the pyrophosphate sequencing method. In this case, generation of pyrophosphate during nucleotide incorporation is monitored by an enzymatic cascade which results in the generation of a chemo-luminescent signal. The 454 Genome Sequencer System (Roche Applied Science cat. No. 04 760 085 001), an example of sequence by synthesis, is based on the pyrophosphate sequencing technology. For sequencing on a 454 GS20 or 454 FLX instrument, the average genomic DNA fragment size is in the range of 200 or 600 bp, respectively, as described in the product literature.

In some embodiments, a sequencing by synthesis reaction can alternatively be based on a terminator dye type of sequencing reaction. In this case, the incorporated dye deoxynucleotriphosphates (ddNTPs) building blocks comprise a detectable label, which is preferably a fluorescent label that prevents further extension of the nascent DNA strand. The label is then removed and detected upon incorporation of the ddNTP building block into the template/primer extension hybrid for example by using a DNA polymerase comprising a 3'-5' exonuclease or proofreading activity.

In some embodiments, and in the case of the Genome Sequencer workflow (Roche Applied Science Catalog No. 04 896 548 001), in a first step, (clonal) amplification is performed by emulsion PCR. Thus, it is also within the scope of the present disclosure, that the step of amplification is performed by emulsion PCR methods. The beads carrying the clonally amplified target nucleic acids may then become arbitrarily transferred into a picotiter plate according to the manufacturer's protocol and subjected to a pyrophosphate sequencing reaction for sequence determination.

In some embodiments, sequencing is performed using a next-generation sequencing method such as that provided by Illumina, Inc. (the "Illumina Sequencing Method"). Without wishing to be bound by any particular theory, the Illumina next-generation sequencing technology uses clonal amplification and sequencing by synthesis (SBS) chemistry to enable rapid, accurate sequencing. The process simultaneously identifies DNA bases while incorporating them into a nucleic acid chain. Each base emits a unique fluorescent signal as it is added to the growing strand, which is used to determine the order of the DNA sequence.

In some embodiments, sequencing is performed using a single-molecule real-time sequencing, such as PacBio available from Pacific Biosciences of California, Inc.

In some embodiments, the sorted cells are stained and/or labeled for particular biomarkers. For example, one or both populations of cells may be stained and/or labeled for the presence of a particular surface marker.

Flow Cytometry

Figure 4:
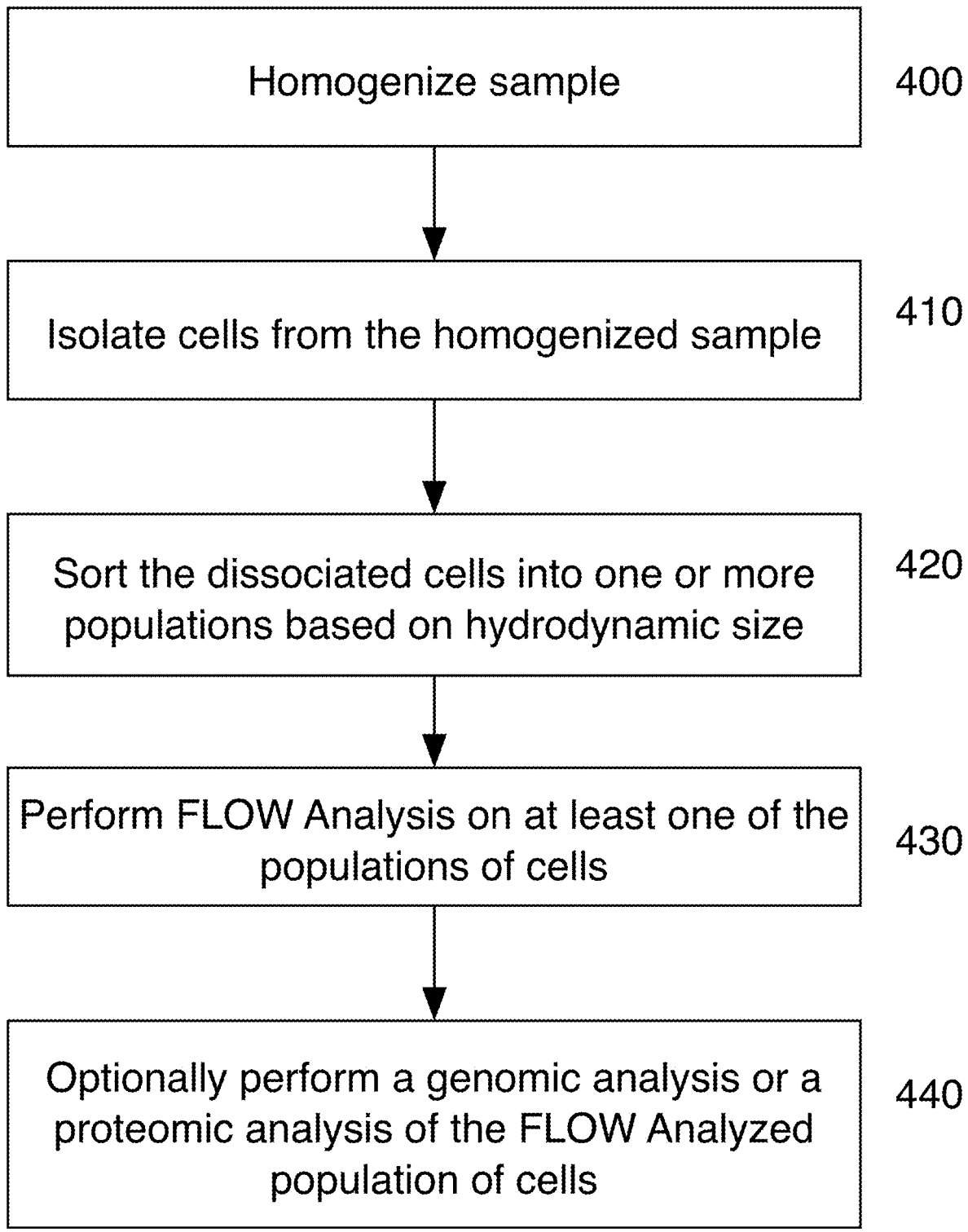
FIG. 4 sets forth a flow chart illustrating a method according to another embodiment of the present disclosure.

In some embodiments, a flow cytometry analysis is conducted (step 430) following sorting of the dissociated cells (step 420) (FIG. 4). Flow cytometry is a technique that allows for simultaneous multiparametric analysis of the physical and/or chemical characteristics of single cells flowing through an optical/electronic detection apparatus. Flow cytometry and its uses are well known to those skilled in the art (see, for example, Ormerod, Flow Cytometry 2nd ed., Springer-Verlag, New York (1999), which is incorporated herein by reference. Such uses include, but are not limited to, immunofluorescence labeling of cell surface antigens using monoclonal antibodies. Clinical applications include, but are not limited to, immunophenotypic analysis of leukemias and lymphomas, detection of minimal residual disease, stem cell enumeration, solid organ transplantation, including T cell cross matching and postoperative monitoring, detection of auto-antibodies, HIV infection, feto-maternal hemorrhage, immunodeficiency diseases, paroxysmal nocturnal hemoglobinuria, reticulocyte analysis, cell cycle analysis, cell proliferation, apoptosis, RNA content, protein content, kinetic analysis of intracellular enzymes, membrane permeability, membrane potential, production of intracellular oxidative species, measurement of drug uptake, binding and endocytosis of ligands, intracellular calcium ions, intracellular pH, intracellular glutathione, chromosome analysis and sorting, tracking cells, measuring cell viability, monitoring electropermeabilization, monitoring fusion or clustering of cells, microbead technology, and the like.

Applicants have found flow cytometric analysis of dissociated tumor samples to be a challenge because of the variety of cells in a tumor having different physical characteristics. Certain routine procedures such as doublet discrimination rely upon having a population of cells with fairly homogenous features; for example, in a mixed population, doublets of normal cells might be difficult to distinguish from tumor cells. A size-based fractionation of the dissociated sample would simplify flow cytometric analysis by providing two cell populations—one enriched for tumor, one enriched for normal cells—that would each individually be simpler to stain and analyze. Following size-based enrichment, staining and FACS would allow one to easily sort an immune population that is positive for a specific marker, or a tumor population positive for a specific marker, and analyze the genomics or proteomics of that specific population. It would also permit the determination of percentages of tumor cells or immune cells positive for a specific marker, even if one did not care to collect and further analyze the population.

Biomarker Analysis

In some embodiments, the populations of enriched cells, nuclei, or small tissue aggregates are stained in an assay to identify particular target molecules. The target molecules can be nucleic acid sequences or proteins. The skilled artisan will appreciate that a target protein may be produced from a target nucleic acid sequence associated with (e.g., correlated with, causally implicated in, etc.) a disease. In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

In other examples, a target protein produced from a nucleic acid sequence (e.g., genomic target nucleic acid sequence) that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC-000013, nucleotides 47775912-47954023), p53 (17p13.1; e.g., GENBANK™ Accession No. NC-000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC-000012, complement, nucleotides 56196638-56200567), FUS (16p11.2; e.g., GENBANK™ Accession No. NC-000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF1, AP1 (1p32-p31; e.g., GENBANK™ Accession No. NC-000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC-000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC-000022, nucleotides 27994271-28026505); FLI1 (11q24.1-q24.3; e.g., GENBANK™ Accession No. NC-000011, nucleotides 128069199-128187521), PAX3 (2q35-q37; e.g., GENBANK™ Accession No. NC-000002, complement, nucleotides 222772851-222871944), PAX7 (1p36.2-p36.12; e.g., GENBANK™ Accession No. NC-000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC-000019, complement, nucleotides 45431556-45483036), MYCL1 (1p34.2; e.g., GENBANK™ Accession No. NC-000001, complement, nucleotides 40133685-40140274), REL (2p13-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

Kits

In some embodiments, the present disclosure provides a kit comprising components needed to homogenize, dissociate, and sort cells, nuclei, or small tissue aggregates from an input sample. For example, the kit may include reagents needed to dissociate cells from a particular type of tissue, and the kit may also include a microfluidic device appropriate for sorting cells having particular sizes.

EXAMPLES

Materials

Mechanical dissociation was performed with an IKA Works Tube Mill Control system from IKA-Works (0004180001; Staufen im Breisgau, Germany). All filters used were from Pluriselect (San Diego, Calif.). Buffers used were from the following companies: CC1 (950-124; Ventana Medical Systems, Tucson, Ariz.), autoMACS buffer (130-091-221, Miltenyi Biotech), dPBS (14190, Fisher Scientific, USA). Tween 20 was purchased from Fisher Scientific, USA (AC233362500). The following reagents were purchased from Sigma, USA: Spermine tetrachloride (S2876), DAPI (D9542), Pepsin (P7012). Proteinase K was purchased from VWR, USA (0706). Tyramide-Rhodamine 101 was synthesized in house using chemicals purchased from Sigma. Mouse anti-cytokeratin 8/18 antibody (760-4344) and Goat anti-mouse HRP-conjugated antibody (760-4310) were from Ventana Medical Systems. Goat-anti-Mouse antibodies conjugated with Alexa 488 or Alexa 647 were purchased from Invitrogen (A-11001).

Tissue Models and Clinical Samples

All tissue samples were fixed in 10% neutral buffered formalin for 24 hours at Ventana Medical Systems. Human tonsils were obtained from Northwest Medical Center (Tucson, Ariz.). Tumor samples were obtained from GLAS/ (Winston-Salem, N.C. http://glaswpcopy.wpengine.com/).

Example 1—Fixed Tissue Dissociation

Fixed tonsil tissue was mechanically dissociated in an IKA blender in CC1 buffer (1:5) that had been heated to 85° C., incubated for 30 min at 85° C., and then blended again in an IKA blender (2 min, 10 second intervals). Blended material was exchanged into 1:10 MACS buffer (1:10) and filtered through a 40 µm filter. Filtered dissociated cells were analyzed using a Coulter counter for yield and size distribution.

For tumor tissue, bulk mechanical dissociation was first carried out in MACS buffer in an IKA blender at a 1:1 tumor:MACS ratio. Aliquots of the total homogenate were further blended in CC1 buffer as described for tonsil above. The blended material was filtered through a 1 mm×1 mm metal sieve. CC1 buffer was exchanged for dPBS (1:10) by centrifugation at 300×g for 1 min in a benchtop microcentrifuge (Eppendorf); all subsequent liquid exchanges were performed in the same manner. After centrifugation, the pellet was resuspended 1:1 in dPBS containing 1 mg/ml proteinase K and incubated at 50° C. for 10 min. To quench proteinase K and for further dissociation, the sample was exchanged into 5 mg/ml pepsin in 150 mM NaCl, pH 1.5. The pH of the solution was tested with pH strips and re-adjusted to 1.5-2 using 5 M HCl as needed. The sample was incubated for 30 min at 37° C., with gentle mixing every 10 min. Pepsin was inactivated by the adjustment of the pH to above 8 with 5 M NaOH, and then the solution containing the pepsin was exchanged for autoMACS buffer, 1% Tween 20 and 1.5 mM spermidine tetrachloride (MACS-T-STC). The digested sample was filtered through a 40-µm filter using 10 ml of MACS-T-STC, collected by centrifugation, and resuspended in 500 µl MACS-T-STC for storage prior to downstream applications.

Example 2—Single Cell Extraction from Fixed Tissue

Fixed tissues (tonsil or tumor) were first blended in MACS buffer at 1:1 ratio in an IKA blender to generate a homogenate that can be stored for further use. To extract intact single cells the following steps were performed:

1. The homogenate was suspended in CC1 buffer at 1:5 ratio and heated at 85 C. for 30 min 2. The pre-heated suspension was blended in IKA blender (2 times, 2 min each with 10 second intervals)

3. The blended suspension was filtered with 1 mm metal sieve

4. The filtrate was filtered again with 20 µm cell strainer

5. The filtrate was filtered with 10 µm cell strainer

6. The filtrate contained mostly single cells while the residuals contained different size fragments.

7. Single cell suspension was centrifuged at 500 g and re-suspended in PBS

Example 3—Extraction of Tissue from Paraffin Blocks

Paraffin blocks containing tissue were melted at 65° C. for 30 min, and excess wax was discarded. Warm tissue was diced into pieces less than 1 mm2 in size, and tissue pieces were placed in a cassette with mesh sides. Cassettes were placed in a Leica autoprocessor and incubated in xylene at 42° C. with stirring for 2 h. Cassettes were exchanged into ethanol and incubated at room temperature with stirring for 1 h. Tissue was rehydrated using two exchanges of 1.5 L dH2O with stirring at room temperature for 1 h. Rehydrated tissue was dissociated as described above.

Example 4—Sample Procedure for Obtaining a Single Cell Suspension from a Primary Human Tumor (Dissociation of Cells from a Tumor Sample)

1. Before digestion with tumor collagenase, primary human tumors are cross-cut into small pieces and minced completely until nearly liquid by using scalpels; be sure to cut the tissue and not tear the tissue.

2. Add collagenase based on amount of tissue. Collagenase: 9 parts medium 199 to every 1 part collagenase/hyaluronidase. Make up 200-250 units of collagenase mix per mL of tumor, total volume adjusted to the size of the tumor, not to exceed 3-4 mL.

3. Transfer the cut-up tumor in collagenase solution into a 50 mL conical tube.

4 Put the 50 mL conical tube into a 37° C. shaker or water bath. If in shaker, set motion at 65 rpm for 30 minutes to 1 hour, mixing half way in between. Otherwise, incubate for up to 1 hour in water bath, mixing every 15 minutes.

5. Titrate the mixture 20-25 times using a 5 mL syringe with either 18 or 23 gauge needle. The suspension should go through the needle.

6. Stop digestion by adding 2% FBS/HBSS mix in at least equal amount of collagenase mix added.

7. Cells are then either centrifuged for 30 seconds at 40 g to separate single cells/fibroblasts from organoids (supernatant will contain single cells, pellet organoids) or filtered through a 40 µm nylon mesh cell strainer then centrifuged for 5 minutes at 1000 rpm, supernatant aspirated off, and pellet re-suspended in 2% FBS/HBSS mix.

8. Wash twice with 2% FBS/HBSS mix.

9. Optional differential sedimentation step, to separate the aggregates of cells from the single cells, as described below:

9.1 After first wash with M-199, resuspend cells in 10 mL M-199. Agitation by hand and then let sit for 15 minutes 9.2 Carefully, remove the liquid from the cells that have settled to the bottom of the tube and set aside.

9.3 Repeat previous two steps once and proceed. Be sure to do a cell count both to the supernatant and the pelleted cells.

10. After last wash, resuspend cells in 5 to 10 mL media and/or freeze organoids. Take a 50 µL aliquot to Coulter Count. Count the nuclei so you know how many cells are present.

11. Plate the cells in 5% IH at as desired density, usually at 106 cells per 35 mm plate. Freeze cells that are not plated at 5-10×106 cells per ampule in Freezing Media.

Example 5—Cell Size Analysis

Staining using Tyramide Signal Amplification (TSA)

Nuclei ($3\times10^7$ particles per tube) were centrifuged at 300×g for 2 min prior to resuspension in 0.3 ml 3% H2O2. After 15 min incubation, cells were washed 3 times with 0.1% Tween 20, 0.1% BSA in PBS. TSA blocking buffer (0.3 ml) was added for 5 min, followed by incubation in 0.2 ml primary antibody for 30 min at 37° C. Cells were washed 3 times with 0.1% Tween 20, 0.1% BSA in PBS and then resuspended in 0.2 ml goat anti-species antibody conjugated to horseradish peroxidase for 30 min at 37° C. Cells were diluted in 1.2 ml 20 µM Tyramide-Rhodamine 101 and incubated for 5 min, followed by 1.2 ml TSA H2O2 for 30 min. Cells were washed with 0.5% dextran, 0.1% Tween20, 0.1% BSA in PBS 3× and resuspended in MACS-T-STC for storage. Prior to imaging or flow cytometry, cells were stained with 3 µM DAPI for 10 min.

Flow Cytometry

Samples were filtered through a 40 µm filter prior to analysis. Analysis and sorting were carried out on a Sony SH800 cell sorter. Doublet discrimination was carried out using DAPI pulse width and area.

Measurement of the Yield and Size Distribution of Cells/Nuclei

Samples were diluted 1:10,000 in Isoton II solution (Beckman Coulter) and analyzed on a Multisizer 4e (Beckman Coulter). Reproducibility was assessed by monitoring the size distribution of the particles from different preps for the same tumor. Size distributions were similarly measured for FACS-sorted cells and nuclei.

Measurement of Size Distribution of Cells/Nuclei from Images.

Nuclei/cell samples were diluted to around $10^5$ particles per ml and plated on glass slides. Brightfield images were taken at 20× magnification across multiple fields of view (at least 6 per sample) on a Zeiss Axio microscope for which the pixel:micron conversion has previously been calibrated. Images were thresholded in ImageJ to create binary masks, which were then used to determine the area of singlet cells. Area measurements were used to calculate diameters for all singlet cells or nuclei in each field of view.

Results

Analysis of the Size Distribution of Dissociated Tumor Nuclei

Figure 5A:
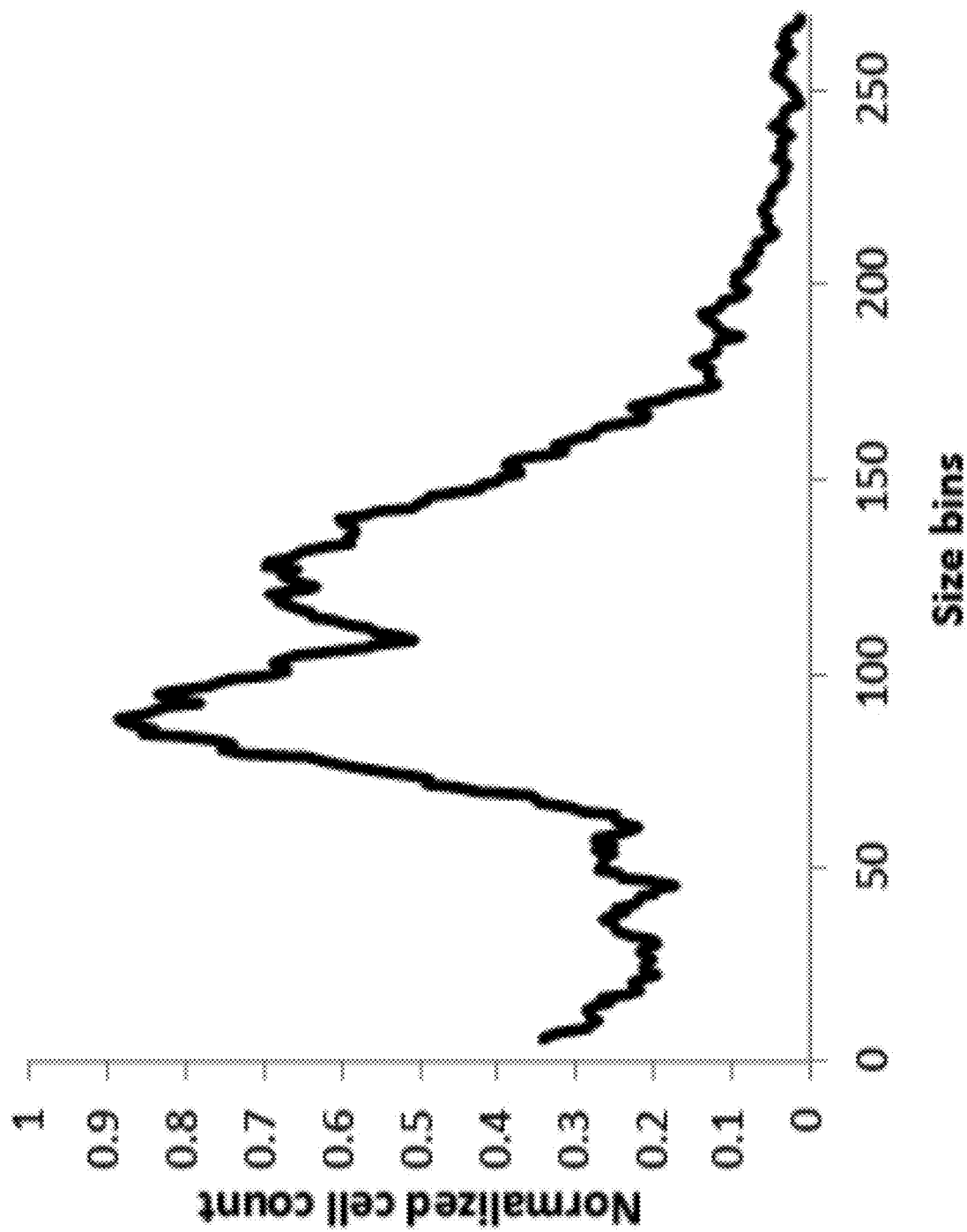
FIG. 5A sets forth a size distribution of nuclei prepared from a representative colon adenocarcinoma tumor sample, the graph showing a Coulter counter analysis, with traces smoothed using a moving average. The Coulter method of sizing and counting particles is based upon measurable changes in electrical impedance produced by nonconductive particles suspended in an electrolyte. Particles measured on a coulter counter are grouped into bins of the same size (size bins). Size bin numbers reported on the horizontal axis refer to increasing diameters of particles. Using microscopic images, we have empirically estimated that the size bin of about "50" roughly correlates to about 6 µm diameter; size bin of about "100" roughly correlates to about 9 µm diameter, and size bin of about "150" roughly correlates to about 14 µm diameter.
Figure 5B:
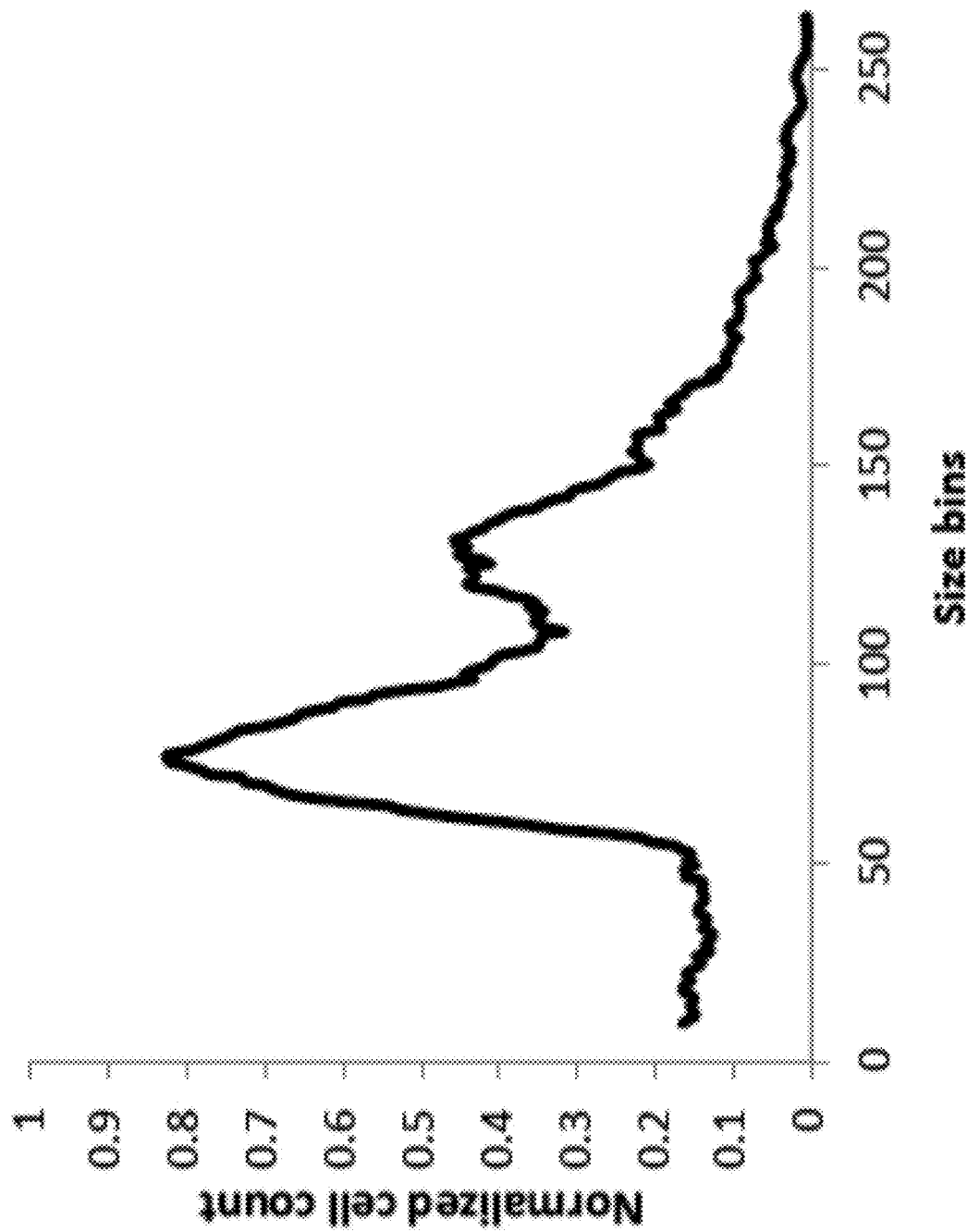
FIG. 5B sets forth a size distribution of nuclei prepared from a representative lung squamous cell carcinoma tumor sample, the graph showing a Coulter counter analysis, with traces smoothed using a moving average.

While determining the reproducibility of yields of tissue dissociation methods using a Coulter counter, we noted that nuclei from tumors of different types distributed into two populations of similar relative size distributions as depicted in FIGS. 5A and 5B.

FACS Sorting of Dissociated Tumor Nuclei

Figure 6A:
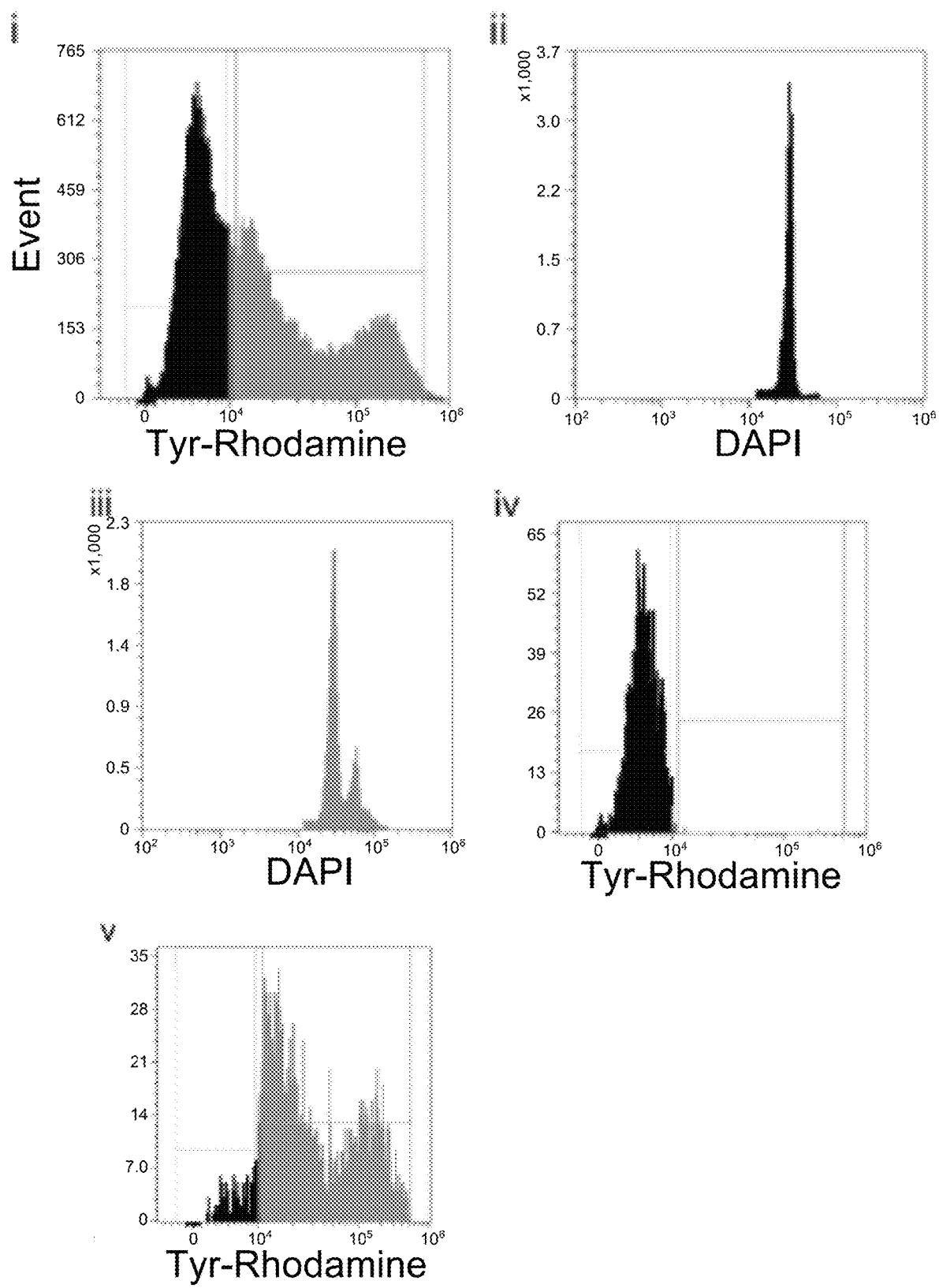
FIG. 6A compares histograms of flow cytometry data for nuclei isolated from a colon tumor representative sample and further illustrates that positive cytokeratin (CK) staining may distinguish tumor nuclei from normal. Panel (i) represents CK staining intensity, visualized by TSA-Rhodamine 101. Gates were established for CK-positive and CK-negative nuclei. Panels (ii and iii) represent DAPI staining intensity as a readout of DNA content for the CK-negative and -positive populations defined by gates in panel (i). Note the single peak of DAPI staining intensity in panel (ii) (CK-negative) and the multiple peaks in panel (iii) (CK-positive). Panels (iv) and (v) show histograms of CK staining intensity for nuclei that have been flow sorted according to the gates determined in panel (i). Panel (iv) shows an analysis of the enriched particles defined as CK-negative; and panel (v) shows enrichment for those defined as CK-positive.
Figure 6B:
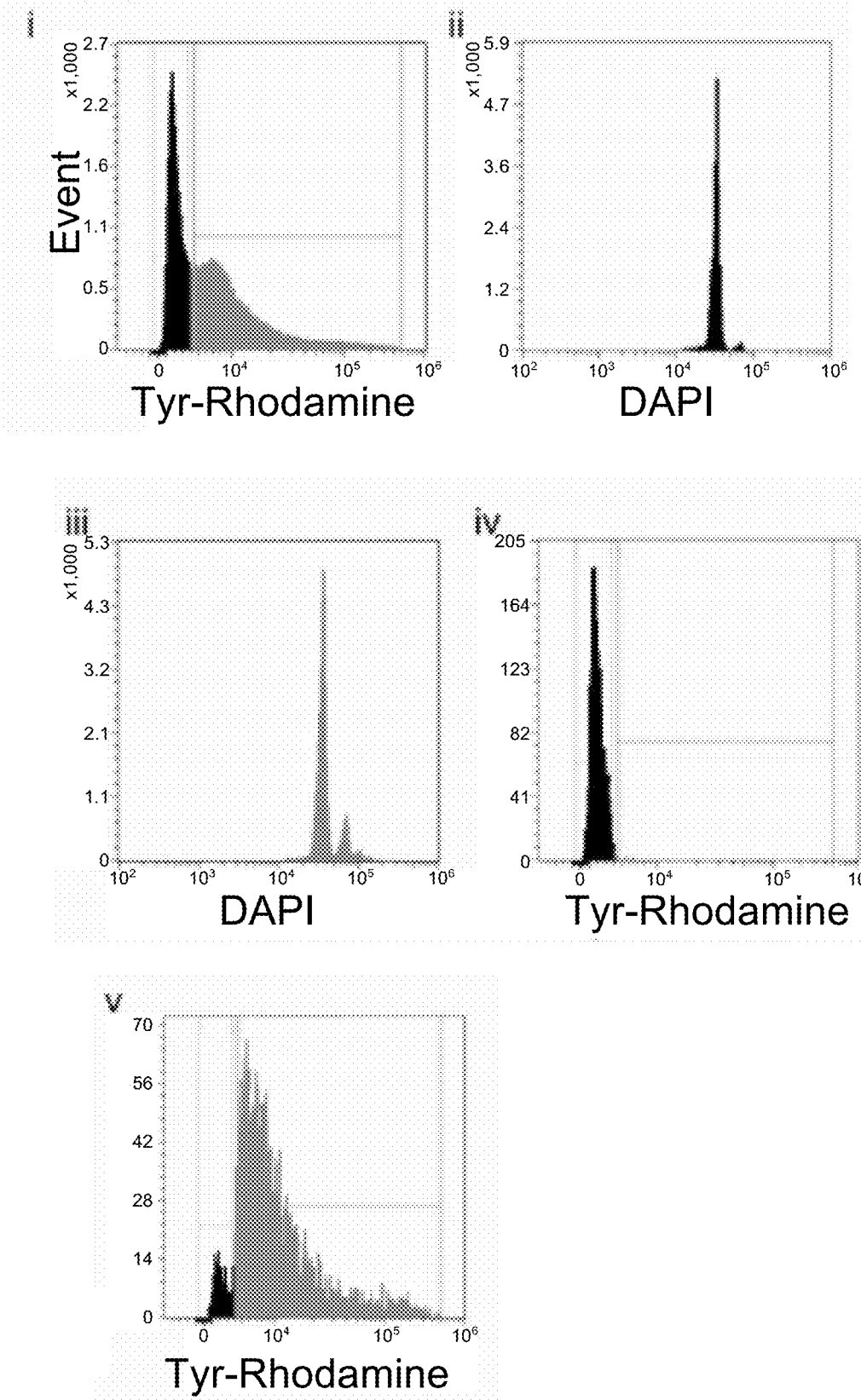
FIG. 6B compares histograms of flow cytometry data for nuclei isolated from a lung tumor representative sample and further illustrates that positive cytokeratin (CK) staining may distinguish tumor nuclei from normal. Panels (i) represent CK staining intensity, visualized by TSA-Rhodamine 101. Gates were established for CK-positive and CK-negative nuclei. Panels (ii and iii) represent DAPI staining intensity as a readout of DNA content for the CK-negative and -positive populations defined by gates in panel (i). Note the single peak of DAPI staining intensity in panel (ii) (CK-negative) and the multiple peaks in panel iii (CK-positive). Panels (iv) and (v) show histograms of CK staining intensity for nuclei that have been flow sorted according to the gates determined in panel (i). Panel (iv) shows an analysis of the enriched particles defined as CK-negative; and panel (v) shows enrichment for those defined as CK-positive.

To determine whether tumor nuclei could be analyzed by flow cytometry and sorted using FACS, we stained nuclei from the same dissociated tumor samples for cytokeratin. Cytokeratin remains associated with nuclei and serves as a "nuclear surface marker" for nuclei of tumor origin. We additionally stained the nuclei with DAPI, which reveals DNA content. FIG. 6 shows that for both the colon and lung cancer samples, we were able to identify a cytokeratin positive population that contained higher DNA content than the cytokeratin negative (normal) population (panels i-iii), confirming that cytokeratin positive nuclei were likely derived from tumor cells, and cytokeratin negative nuclei were likely derived from normal cells in the representative sample. These nuclei were sorted using FACS (a purity check of the sort is shown in panels iv-v). This experiment provided cytokeratin positive and negative nuclei for analysis by Coulter counter.

Analysis of Size Distribution of Sorted Tumor Nuclei

Figure 7A:
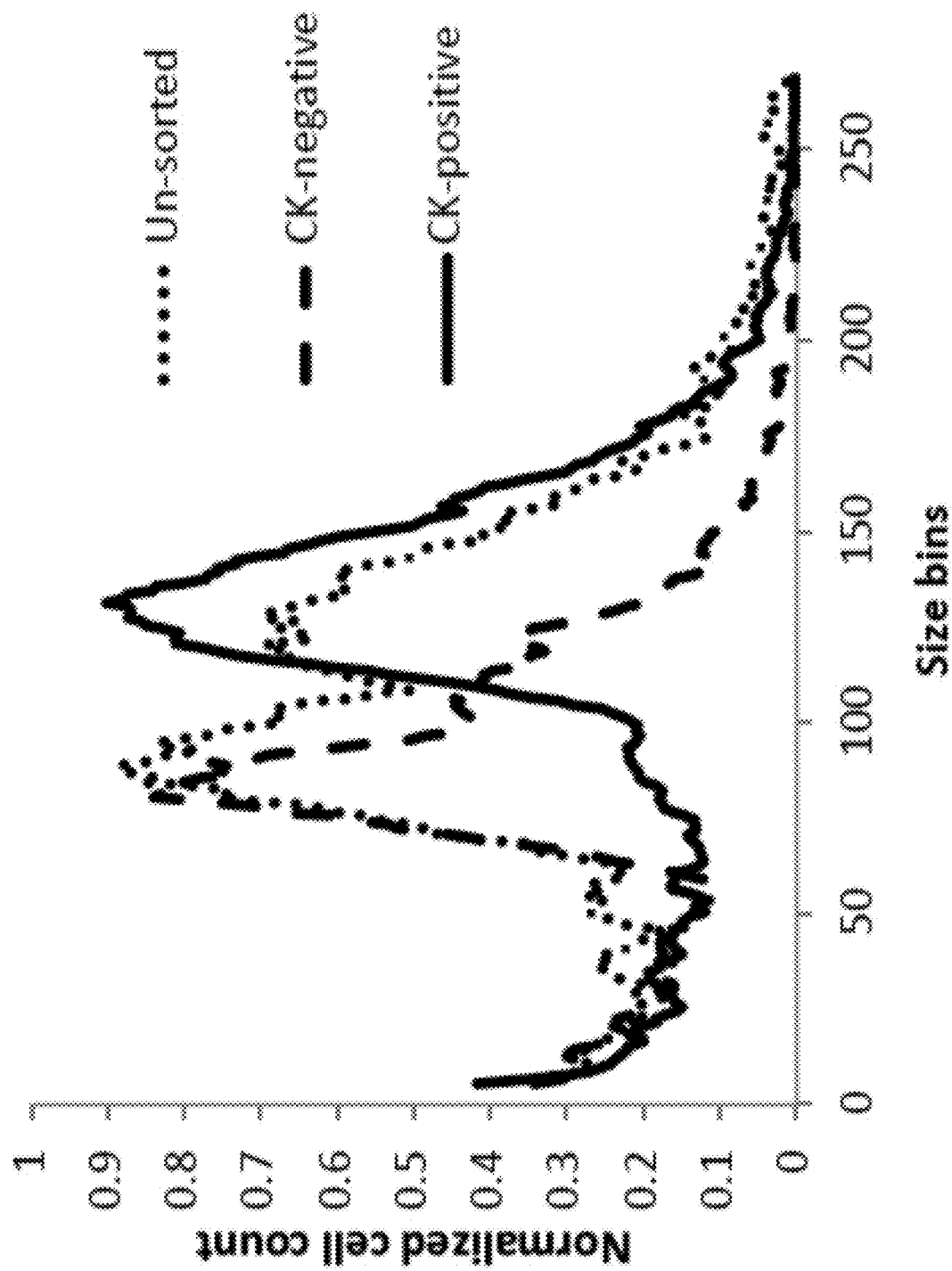
FIG. 7A sets forth a size distribution of sorted nuclei from representative colon adenocarcinoma tumor samples. The graphs show Coulter counter analysis, with traces smoothed using a moving average. Dotted traces correspond to unsorted nuclei; dashed traces correspond to cytokeratin (CK)-negative nuclei sorted using FACS; solid traces correspond to cytokeratin (CK)-positive nuclei sorted using FACS.

We next analyzed the size distribution of the cytokeratin positive and cytokeratin negative nuclei using a Coulter counter. FIG. 7 shows analyses of the sorted populations from the colon and lung tumors obtained in the previous experiment, overlaid on the relative size distributions from FIG. 4. Cytokeratin negative nuclei (dashed traces) aligned with the smaller populations, while cytokeratin positive nuclei (solid traces) aligned with the larger populations. These data support that the smaller nuclei derive from normal cells, while the larger nuclei derive from tumor cells. These data are in agreement with the larger size of tumor nuclei relative to immune nuclei seen in histological H&E stained slides (not shown).

Figure 8:
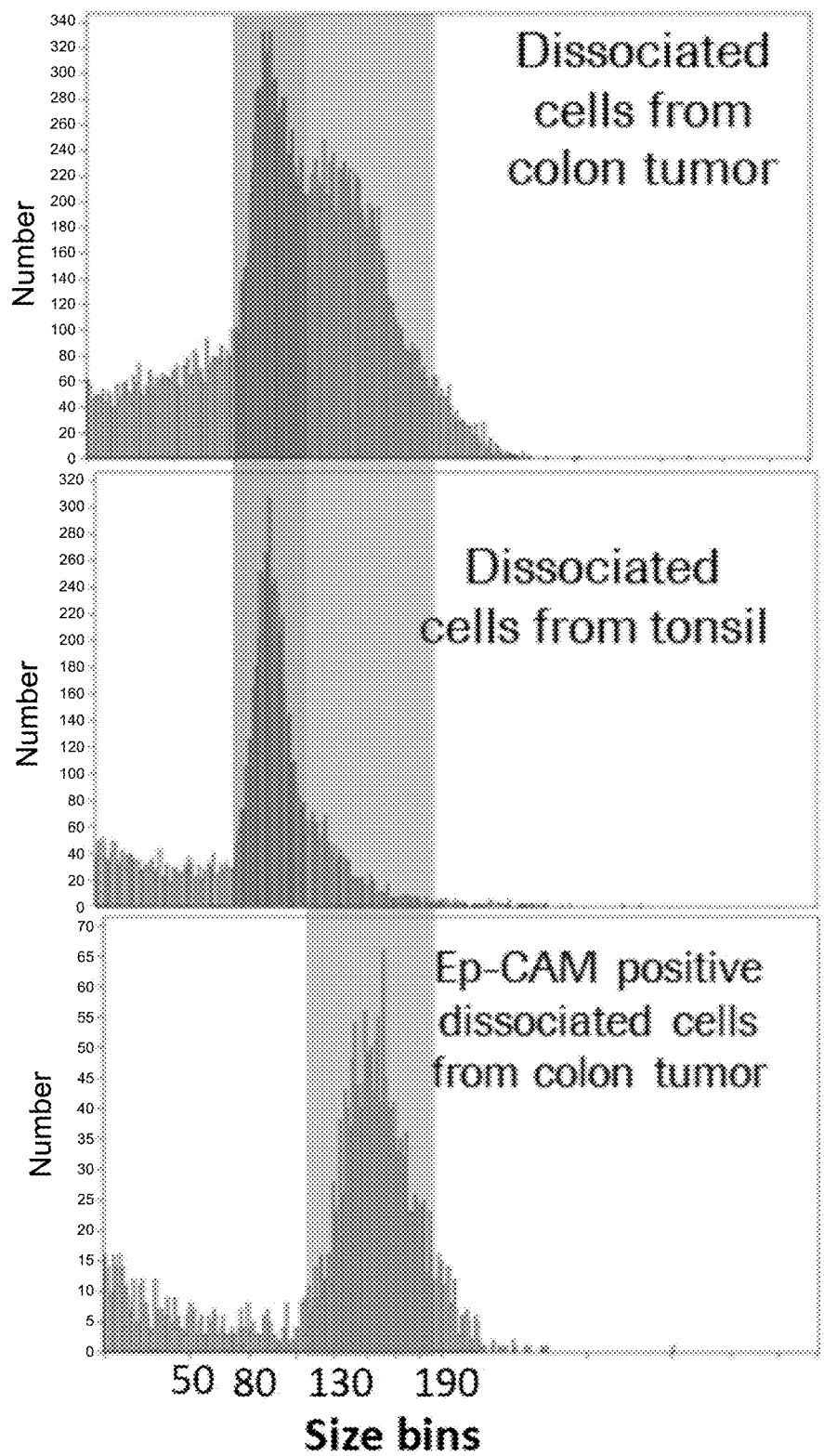
FIG. 8 sets forth a distribution of extracted single cells from representative tumor samples. Graphs show Coulter counter analysis of single cells dissociated from colon tumor (top), single cells dissociated from tonsil (bottom), and Ep-CAM positive cells dissociated from colon tumor then sorted with FACS.

Analysis of the Size Distribution of Dissociated Tumor Cells:

The size-based analysis of cells dissociated from fixed tumors (colon and lung) by Coulter counter reproducibly yielded a bimodal distribution (FIG. 8). To better understand the nature of the distribution, EpCAM positive cells dissociated from fixed colon tumor were analyzed. The size of the Ep-CAM positive cells aligned with the size of the larger cell population within the dissociated tumor cells. Fixed tonsil was also blended, and the size of the extracted single cells was compared to size of tumor dissociated cells. The size of the tonsil dissociated cells aligned with the size of the smaller cell population within the dissociated tumor cells (FIG. 8).

Analysis of Size Distribution of Tissue Extracted from Paraffin

Figure 9:
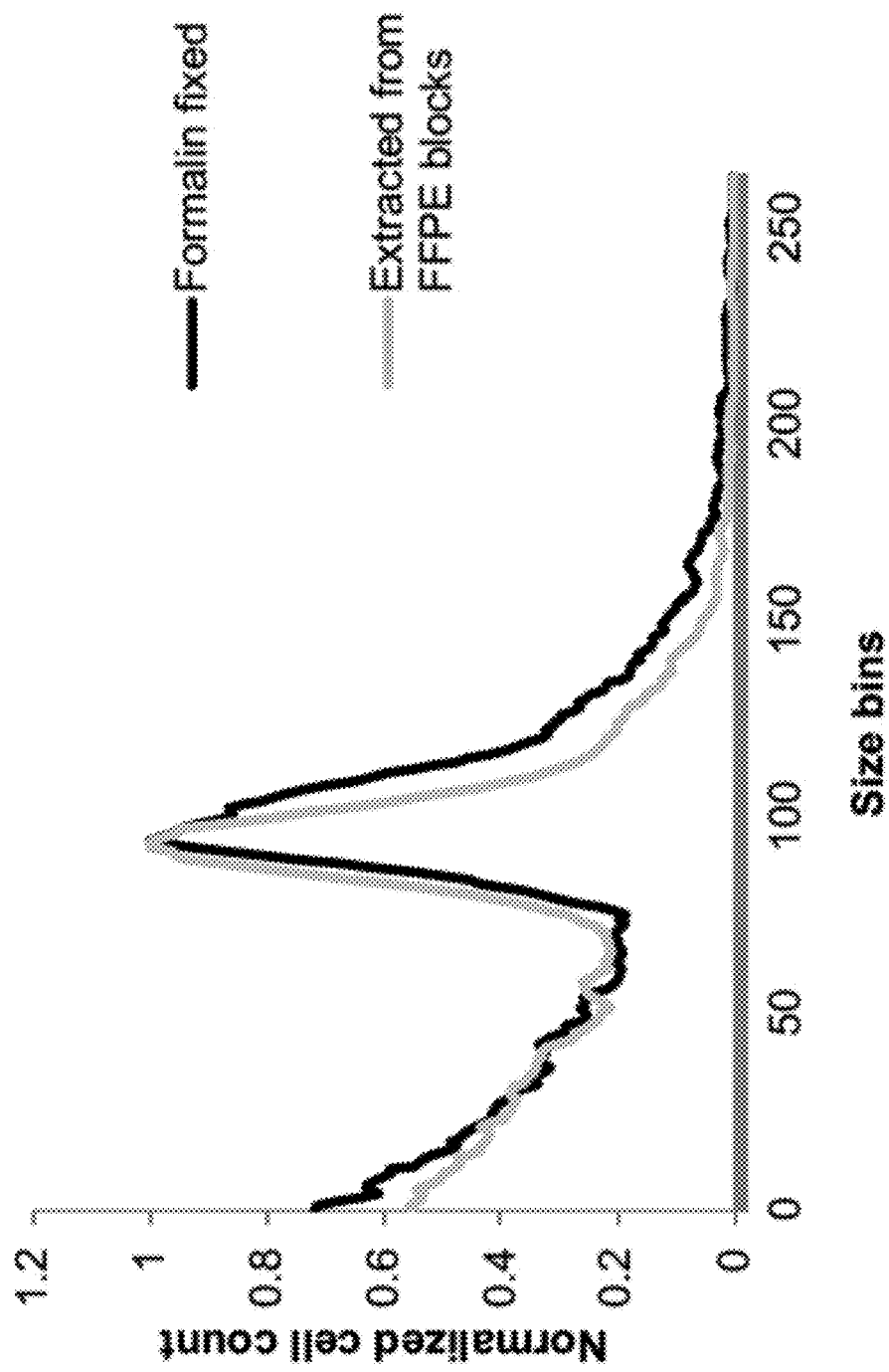
FIG. 9 sets forth size distribution of cells dissociated from formalin fixed tonsil (black trace) and formalin fixed, paraffin-embedded tonsil (grey trace). Graphs show Coulter counter analysis with traces smoothed using a moving average.

We next sought to determine whether tissue extracted from paraffin blocks can be dissociated into cells that are similar in size to those isolated from formalin fixed tissue that has not been embedded in wax. The aim of this experiment is to determine whether any size-based discrimination of particles may be applied to tissue that has been extracted from wax, such as archival tumor block samples. To test this, we mechanically dissociated formalin fixed tonsil tissue that had never been embedded in wax and analyzed cells using a Coulter counter (FIG. 9, black). We also extracted tonsil tissue from paraffin blocks (see methods), and dissociated and analyzed it similarly (FIG. 9, grey). These data show that there is a similar size distribution of cells isolated from tissue that has never been embedded compared to tissue that has been extracted from paraffin.

Figure 16A:
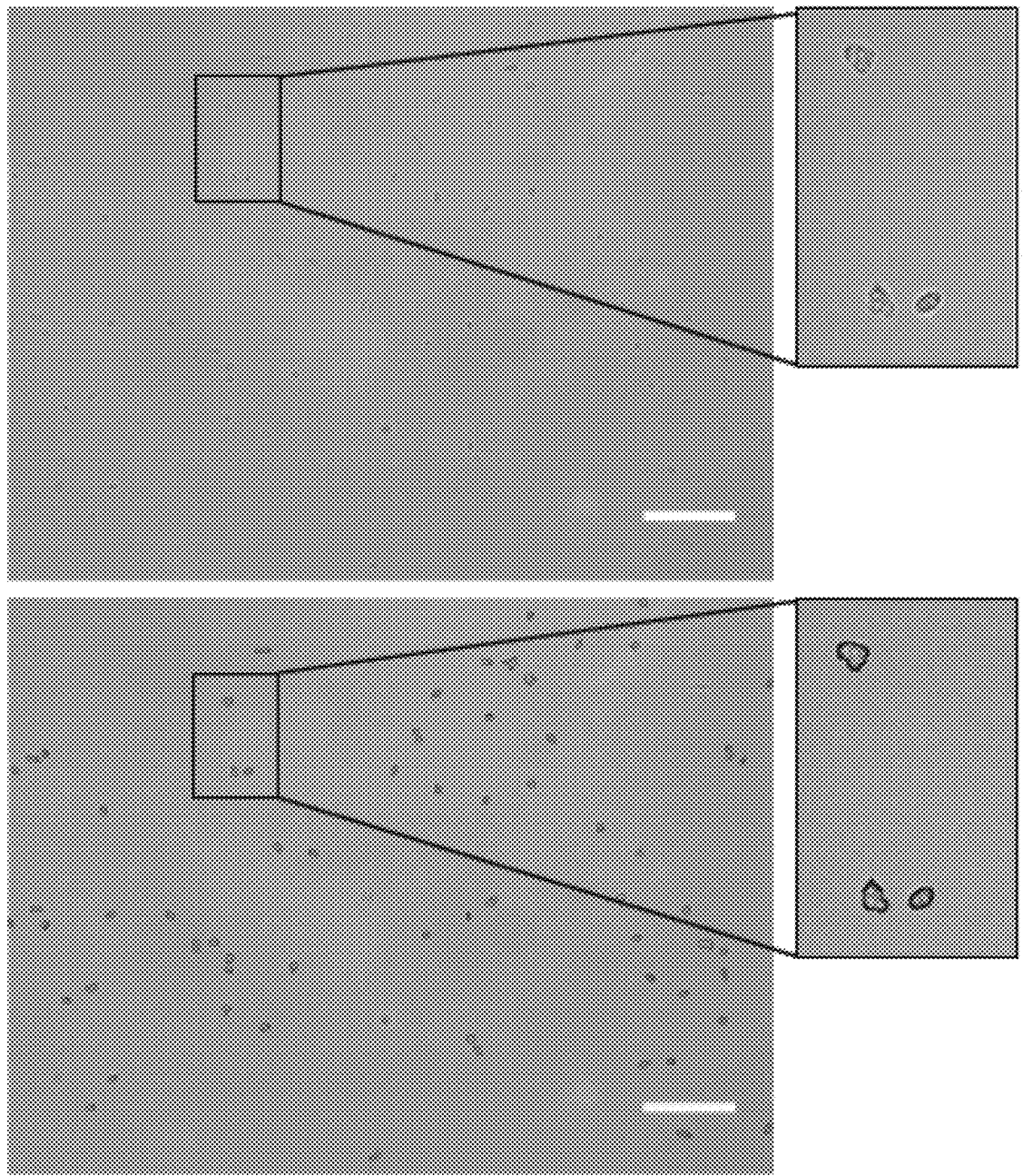
FIG. 16A provides a brightfield image of dissociated nuclei from fixed tonsil tissue. The illustrated inset shows increased magnification of nuclei. The lower panel shows a mask (black outline) used for area calculation in ImageJ. The scale bar is 100 µm.
Figure 16B:
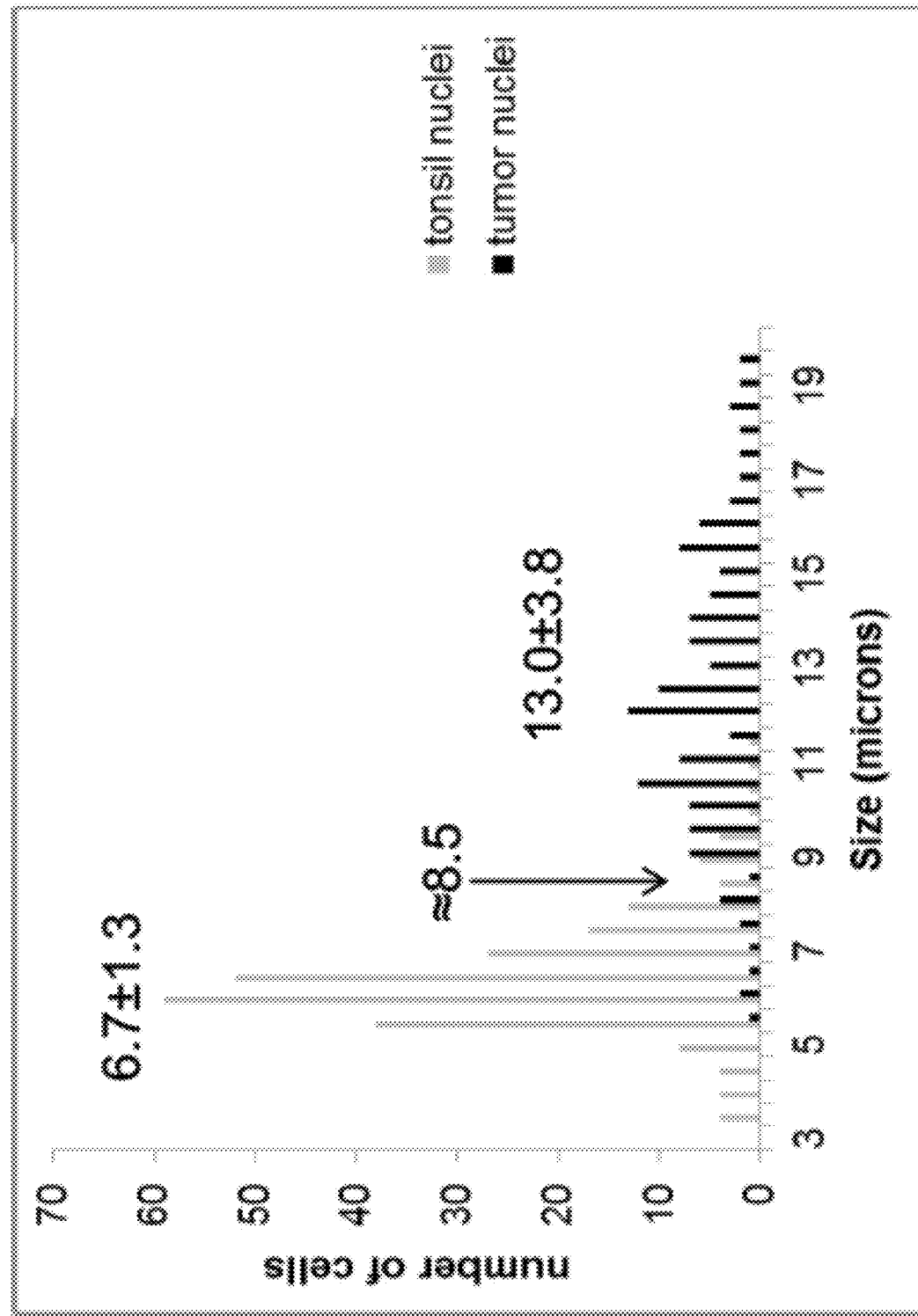
FIG. 16B provides a graph showing size ranges calculated using images as in (A) of tonsil nuclei, and of tumor nuclei from an ovarian tumor containing greater than 80% tumor content. Average size of tonsil nuclei was calculated at 6.7 µm, while average size of tumor nuclei was 13.0 µm. A cutoff of 8.5 µm would allow for separation of the two populations.
Figure 16C:
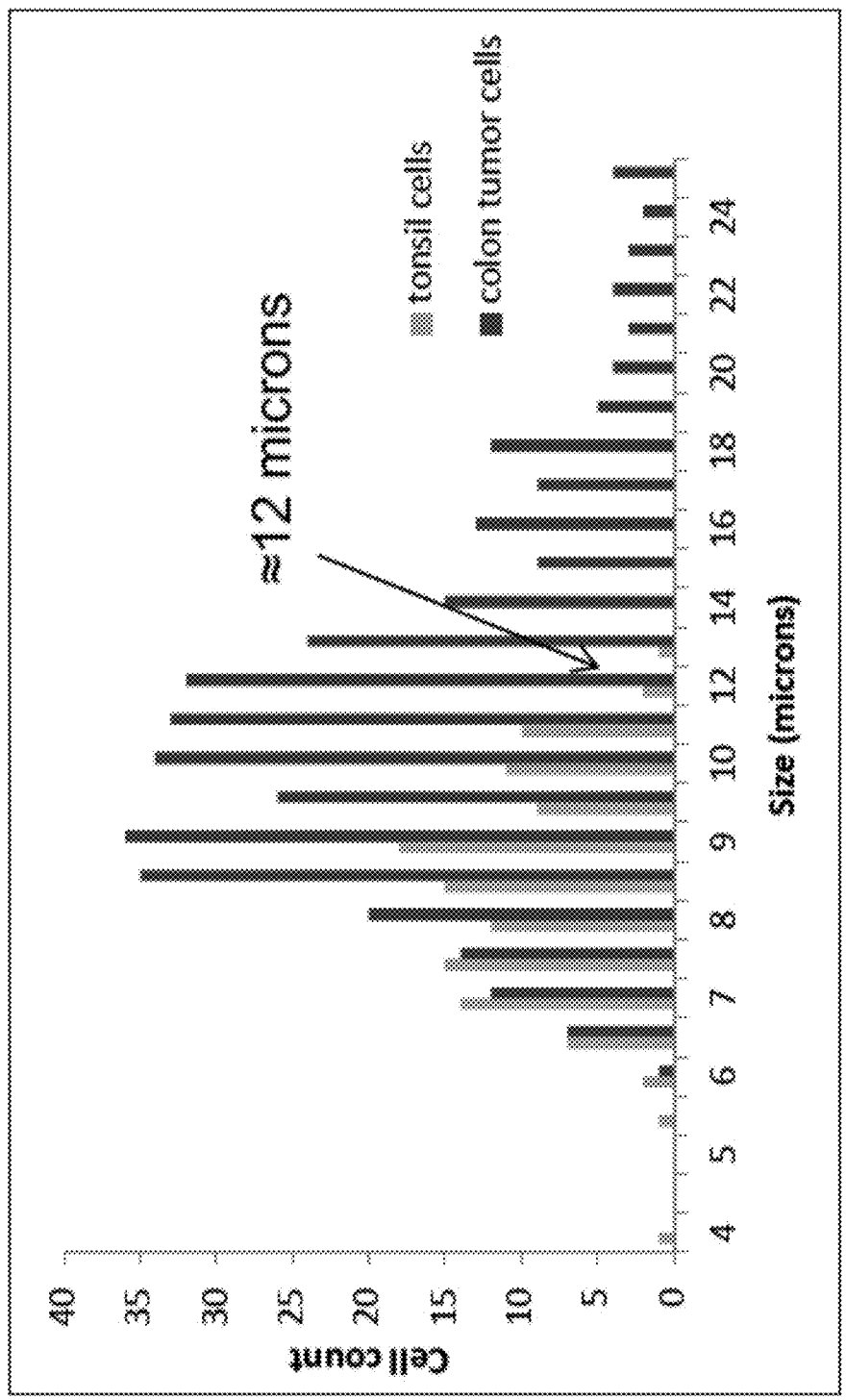
FIG. 16C provides a graph showing size ranges calculated using images of tonsil cells, and of tumor cells from a colon cancer containing around 40% tumor cell content (measured by flow cytometry, not shown). Average size of a tonsil cell was calculated at 8.7+/−1.5 µm, while average size of cells in the colon tumor sample, which consists of around 40% tumor cells, 60% normal cells, is 12.0+/−4.2 µm. Assuming normal cells follow the size distribution of tonsil cells, a cutoff of around 12 µm would allow for enrichment of tumor cells. In support of this, 40% of the cells in the colon tumor sample are 12 µm or larger.

Analysis of Size Distribution of Nuclei and Cells from Tonsil Tissue and Tumor Tissue Using an Orthogonal Image Based Method To validate the exact sizes of nuclei and cells, we performed an image based analysis of nuclei and cells isolated from tonsil and tumor tissue (FIG. 16). These data support the size difference between tumor and normal cellular particles identified using the coulter method and provide an estimation of the exact diameters that could be used to separate the populations.

Example 6—Next Generation Sequencing Methodology

Genomic DNA was purified from each sample using Roche High Pure FFPET DNA Isolation Kit (Roche, Product No.: 06650767001) following manufactures recommended procedure, with exception of increasing proteinase K digestion time to 2 hours at 56° C. in shaking incubator. Yield of purified gDNA was measured by analysis on NanoDrop 8000 (ThermoFisher).

Libraries were constructed from 1 ug of purified input gDNA using the SeqCap EZ HyperCap Workflow User's Guide, v1.0 (Roche Sequencing Solutions), brief details follow only to highlight key steps from user-guide. Extracted gDNA was enzymatically fragmented, repaired, and readied for target enrichment by using the KAPA HyperPlus library prep kit according to manufacturer's instructions (Roche Sequencing Solutions). Specifically, 1 ug of gDNA from each sample was fragmented for 40 minutes at 37° C., end-repaired and A-tailed for 30 minutes at 65° C., and adapter-ligated for 16 hours at 16° C. using SeqCap single-index adapters (Roche SeqCap Adapter Kit A and B) at final adapter concentration of 45 picomolar. No Pre-cap LM-PCR amplification was performed on libraries. Target enrichment was performed using SeqCap EZ MedExome Enrichment Kit (Roche), following user guide mentioned above; specifically, 16 hours at 47° C. Post-capture LM-PCR performed for a total of 14 cycles, instead of 7 to 9 as recommended in user guide.

Libraries were pooled, readied for sequencing, and sequenced on Illumina HiSeq 2500 instrument using HiSeq HO V3 kit by following HiSeq 2500 System Guide (Illumina Document #15035786 v01)

STATEMENT OF INDUSTRIAL APPLICABILITY

The present disclosure has industrial applicability in the field of medicine and diagnostics.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

Additional Embodiments

Additional Embodiment 1. A method of segregating cells from a tissue sample comprising: homogenizing the tissue sample to provide a homogenized tissue sample; sorting cells in the homogenized sample by size, wherein the cells are sorted into at least first and second cell populations, the first cell population enriched in cells having an average diameter ranging from about 4 µm to about 12

μm, and the second cell population enriched in cells having an average diameter ranging from about 12 μm to about 50 μm.

Additional Embodiment 2. The method of additional embodiment 1, wherein at least 90% of the cells in the first cell population have an average diameter ranging from 4 μm to 12 μm, and wherein at least 90% of the cells in the second cell population have an average diameter ranging from 12 μm to 50 μm.

Additional Embodiment 3. The method of any of the preceding additional embodiments, wherein the first population of cells is enriched with non-tumor cells, and wherein the second population of cells is enriched with tumor cells.

Additional Embodiment 4. The method of any of the preceding additional embodiments, wherein the tumor cells have an average diameter ranging from about 12 μm to about 50 μm.

Additional Embodiment 5. The method of any of the preceding additional embodiments, wherein the tissue sample is derived from a whole tumor, a partial tumor, and/or lymph nodes.

Additional Embodiment 6. The method of any of the preceding additional embodiments, wherein the tissue sample is derived from residual surgical material or a biopsy sample.

Additional Embodiment 7. The method of additional embodiment 6, wherein the tissue sample is derived from a sample embedded in paraffin.

Additional Embodiment 8. The method of any of additional embodiments 1 to 6, wherein the homogenized tissue sample is further processed prior to sorting.

Additional Embodiment 9. The method of additional embodiment 8, further processing comprises the steps of digesting proteins within the homogenized sample and filtering the homogenized sample.

Additional Embodiment 10. The method of any of additional embodiments 1 to 6, wherein the sorting of the cells in the homogenized sampled by size does not require the step of staining the cells.

Additional Embodiment 11. The method of additional embodiment 10, wherein a microfluidic device is utilized to sort the cells in the homogenized sample by size.

Additional Embodiment 12. The method of additional embodiment 11, wherein the microfluidic device is a deterministic lateral displacement device.

Additional Embodiment 13. The method of additional embodiment 12, wherein cells within the homogenized tissue sample having a critical diameter of less than about 12 μm move with a convective flow of fluid passing through the device, while cells within the homogenized tissue sample having a critical diameter of greater than about 12 μm move in a direction dictated by an arrangement of arrays.

Additional Embodiment 14. The method of additional embodiment 11, wherein the microfluidic device is a hydrophoretic filtration device.

Additional Embodiment 15. The method of additional embodiment 11, wherein the microfluidic device is a hydrodynamic filtration device.

Additional Embodiment 16. The method of additional embodiment 11, wherein the microfluidic device utilizes inertial focusing in curved channels.

Additional Embodiment 17. The method of additional embodiment 11, wherein the microfluidic device utilizes inertial focusing in straight channels.

Additional Embodiment 18. The method of additional embodiment 17, wherein inertial focusing in straight channels comprises one of a pinched flow fractionation process or a hydrodynamic spreading process.

Additional Embodiment 19. The method of any of additional embodiments 1 to 6, further comprising the step of assaying the cells within the first or second population for a first biomarker.

Additional Embodiment 20. The method of additional embodiment 19, wherein a presence of the first biomarker is indicative of cancer.

Additional Embodiment 21. The method of additional embodiment 19, wherein the first biomarker is an immune cell marker.

Additional Embodiment 22. The method of any of additional embodiments 1 to 6, wherein each of the first and second populations of cells are independently sequenced using next-generation sequencing.

Additional Embodiment 23. The method of any of additional embodiments 1 to 6, wherein the first and second populations of cells provide matched tumor and normal cell samples for a patient.

Additional Embodiment 24. The method of additional embodiment 23, wherein the matched tumor and normal cells are analyzed to identify somatic mutations, copy number variations, or other genetic alterations.

Additional Embodiment 25. A method of sequencing genomic material within a sample comprising: homogenizing a tissue sample to provide a homogenized tissue sample; and sequencing at least a first population of cells which are enriched with tumor cells.

Additional Embodiment 26. The method of additional embodiment 25, wherein cells within the homogenized sample are sorted with a microfluidic device to provide at least two populations of cells, wherein at least 80% of the cells within the first population of cells after sorting are tumor cells.

Additional Embodiment 27. The method of any of additional embodiments 25 to 26, wherein the at least 80% of the cells within the first population of cells have a size greater than 12 μm.

Additional Embodiment 28. The method of any of additional embodiments 25 to 27, wherein the cells are sorted according to their hydrodynamic size.

Additional Embodiment 29. The method of any of additional embodiments 25 to 28, wherein the tumor sample is derived from a surgical resection.

Additional Embodiment 30. The method of any of additional embodiments 26 to 29, wherein the microfluidic device does not require staining of the cells prior to sorting.

Additional Embodiment 31. The method of any of additional embodiments 26 to 30, wherein the microfluidic employs one of deterministic lateral displacement, hydrophoretic filtration, hydrodynamic filtration, inertial focusing in curved channels, and inertial focusing in straight channels.

Additional Embodiment 32. The method of any of additional embodiments 25 to 31, wherein the first population of cells comprises at least 0.05 micrograms of genomic material for sequencing by total weight of the first population of cells.

Additional Embodiment 33. The method of any of additional embodiments 25 to 31, wherein the first population of cells comprises at least 0.1 micrograms of genomic material for sequencing by total weight of the first population of cells.

Additional Embodiment 34. The method of any of additional embodiments 25 to 33, wherein the method comprises at most 4 amplification cycles prior to sequencing.

Additional Embodiment 35. A method of deriving an enriched population of tumor nuclei and an enriched population of normal nuclei from a tumor sample, comprising dissociating the tumor and normal nuclei from the tumor sample; sorting the tumor and normal nuclei by size with a microfluidic sorting device, and where the microfluidic sorting device does not require a step of staining or biomarker analysis prior to sorting.

Additional Embodiment 36. The method of additional embodiment 35, wherein the enriched population of tumor nuclei comprises at least 85% tumor nuclei; and wherein the enriched population of normal nuclei comprises at least 85% normal nuclei.

Additional Embodiment 37. The method of any of additional embodiments 35 to 36, wherein the tumor nuclei within the enriched population of tumor nuclei have an average nucleus size of greater than 8.5 µm.

Additional Embodiment 38. The method of any of additional embodiments 35 to 37, wherein the normal nuclei within the enriched population of normal nuclei comprise an average nucleus size of less than 8.5 µm.

Additional Embodiment 39. The method of any of additional embodiments 35 to 38, further comprising the step of separately sequencing the enriched population of tumor nuclei and the enriched population of normal nuclei.

Additional Embodiment 40. The method of additional embodiment 39, wherein at least one of somatic mutations, copy number variations, or other genetic alterations are identified in the enriched population of tumor cells.

Additional Embodiment 41. The method of any of additional embodiments 35 to 40, wherein the tumor sample is derived from a whole tumor, a partial tumor, one or more lymph nodes, and/or a sample embedded in paraffin.

Additional Embodiment 42. The method of any of additional embodiments 35 to 41, wherein the tumor sample comprises freshly dissociated tissue.

Additional Embodiment 43. A method of treating cancer by identifying cancer subtypes responsive to a particular treatment or active pharmaceutical ingredient, wherein the cancer subtype is identified by sequencing a sample enriched in tumor cells; wherein the method comprises enriching the sample with tumor cells by: (i) homogenizing an input tissue sample comprising at least one of a tumor, one or more lymph nodes, or blood; and (ii) sorting the tumor cells from normal cells with a size-based sorting device, where the size-based sorting device does not require staining the tumor cells prior to sorting.

Additional Embodiment 44. The method of additional embodiment 43, wherein the population of cells enriched in tumor cells comprises a sufficient amount of genomic material such that at most four amplification cycles are conducted prior to sequencing.

Additional Embodiment 45. The method of additional embodiment 44, wherein at most 2 amplification cycles are conducted prior to sequencing.

Additional Embodiment 46. The method of additional embodiment 44, wherein the quantity of genomic material is at least 0.01 micrograms.

Additional Embodiment 47. The method of additional embodiment 44, wherein the quantity of genomic material is at least 0.1 micrograms.

Additional Embodiment 48. The method of additional embodiment 44, wherein the quantity of genomic material is at least 0.2 micrograms.

Additional Embodiment 49. The method of additional embodiment 44, wherein the quantity of genomic material is at least 0.5 micrograms.

Additional Embodiment 50. The method of any of additional embodiments 43 to 49, wherein following identification of the cancer subtype, a course of treatment is provided to a patient from whom the sample was derived.

Additional Embodiment 51. A method of treating cancer by identifying somatic mutations in tumor cells comprising, wherein the method comprises: (i) homogenizing a tissue sample derived from a patient; (ii) dissociating cells within the homogenized tissue sample; and (ii) separating tumor cells from normal cells in the dissociated tumor sample with a microfluidic device to provide: (a) a first population enriched with tumor cells, wherein the tumor cells within the first population have an average diameter of greater than 12 µm, and (b) a second population enriched with normal cells, wherein the normal cells within the second population have an average diameter of less than 12 µm, and wherein the microfluidic device does not require staining or labeling prior to sorting.

Additional Embodiment 52. The method of additional embodiment 51, wherein the microfluidic device employs one of deterministic lateral displacement, hydrophoretic filtration, hydrodynamic filtration, inertial focusing in curved channels, and inertial focusing in straight channels.

Additional Embodiment 53. A method of segregating cells, nuclei, or tissue aggregates from a tissue sample to facilitate downstream analysis comprising:
separating the cells, nuclei, or tissue aggregates from the tissue sample to provide a separated sample;
sorting the cells, nuclei, or tissue aggregates in the separated sample by size using a sorting device, wherein the cells, nuclei, or tissue aggregates are sorted into first and second populations, the first population having a first cell, nuclei, or tissue aggregate average diameter and the second population having a second cell, nuclei, or tissue aggregate average diameter.

Additional Embodiment 54. The method of additional embodiment 53, wherein the first population is enriched with tumor cells, nuclei or tissue aggregates; and the second population is enriched with normal cells, nuclei or tissue aggregates; and wherein the average diameter of the first population is greater than the average diameter of the second population.

Additional Embodiment 55. The method of any of additional embodiments 53 to 54, wherein the sorting device employs one of deterministic lateral displacement, hydrophoretic filtration, hydrodynamic filtration, inertial focusing in curved channels, and inertial focusing in straight channels.

Additional Embodiment 56. The method of any of additional embodiments 53 to 55, further comprising the step of performing a genomic analysis on at least one of the first or second populations.

Additional Embodiment 57. The method of any of additional embodiments 53 to 56, further comprising the step of performing a flow cytometry analysis on at least one of the first or second populations.

Additional Embodiment 58. The method of any of additional embodiments 53 to 57, further comprising the step of staining at least one of the first or second populations for the presence of at least one biomarker.

Additional Embodiment 59. A method of segregating cells from a fresh tissue sample comprising:

homogenizing a fresh tissue sample to provide a homogenized tissue sample; sorting the cells in the homogenized fresh tumor sample by size, wherein the cells are sorted into first and second cell populations, the first cell population enriched in cells having an average diameter ranging from about 6 μm to 12 μm, and the second cell population enriched in cells having an average diameter of greater than 12 μm.

Additional Embodiment 60. The method of additional embodiment 59, wherein the first population of cells is enriched with non-tumor cells, and wherein the second population of cells is enriched with tumor cells.

Additional Embodiment 61. The method of any of additional embodiments 59 to 60, wherein the fresh tumor sample is derived from a fresh whole tumor, a fresh partial tumor, and/or fresh lymph nodes.

Additional Embodiment 62. The method of any of additional embodiments 59 to 60, wherein the fresh tumor sample is derived from fresh residual surgical material or a fresh biopsy sample.

Additional Embodiment 63. The method of any of additional embodiments 59 to 62, wherein the sorting device does not require the step of staining the cells.

Additional Embodiment 64. The method of additional embodiment 63, wherein the sorting device is a microfluidic device.

Additional Embodiment 65. The method of additional embodiment 64, wherein the microfluidic device is a deterministic lateral displacement device.

Additional Embodiment 66. The method of additional embodiment 65, wherein cells within the homogenized fresh tumor sample having a diameter of less than 12 μm move with a convective flow of fluid passing through the deterministic lateral displacement device, while cells within the homogenized sample having a critical diameter of greater than 12 μm move in a direction dictated by an arrangement of arrays.

Additional Embodiment 67. The method of additional embodiment 64, wherein the microfluidic device is a hydrophoretic filtration device.

Additional Embodiment 68. The method of additional embodiment 64, wherein the microfluidic device is a hydrodynamic filtration device.

Additional Embodiment 69. The method of additional embodiment 64, wherein the microfluidic device utilizes inertial focusing in curved channels.

Additional Embodiment 70. The method of additional embodiment 64, wherein the microfluidic device utilizes inertial focusing in straight channels.

Additional Embodiment 71. The method of additional embodiment 70, wherein inertial focusing in straight channels comprises one of a pinched flow fractionation process or a hydrodynamic spreading process.

Additional Embodiment 72. The method of any of additional embodiments 59 to 62, further comprising the step of assaying the cells within the first or second population for a first biomarker.

Additional Embodiment 73. The method of additional embodiment 72, wherein a presence of the first biomarker is indicative of cancer.

Additional Embodiment 74. The method of additional embodiment 72, wherein the first biomarker is an immune cell marker.

Additional Embodiment 75. A method of segregating cells from a tissue sample comprising: homogenizing a tumor sample to provide a homogenized tissue sample; sorting cells in the homogenized tissue sample by size, wherein the cells are sorted into first and second cell populations, the first cell population is enriched in cells having an average diameter of less than 12 μm, and the second cell population is enriched in cells having an average diameter greater than 12 μm.

Additional Embodiment 76. A composition enriched with tumor cells, the tumor cells having a size greater than 12 μm, wherein the tumor cells were separated from normal cells without first staining either the tumor or normal cells.

Additional Embodiment 77. The composition of additional embodiment 76, wherein at least 50% of the composition comprises tumor cells.

Additional Embodiment 78. The composition of additional embodiment 76, wherein at least 65% of the composition comprises tumor cells.

Additional Embodiment 79. The composition of additional embodiment 76, wherein at least 80% of the composition comprises tumor cells.

Additional Embodiment 80. The composition of additional embodiment 76, wherein at least 95% of the composition comprises tumor cells.

Additional Embodiment 81. A kit comprising a first population of cells and a second population of cells, the first population of cells substantially enriched with tumor cells having a size greater than 12 μm, the second population of cells substantially enriched with normal cells having a size less than 12 μm, the first and second populations of cells being derived from the same tumor sample, and wherein the tumor cells and normal cells are unstained.

Additional Embodiment 82. A method of testing for genetic abnormalities comprising performing a genomic analysis on each of the population of cells of additional embodiment 81.

Additional Embodiment 83. The method of additional embodiment 82, further comprising the step of identifying biomarkers on at least one of the populations of cells of additional embodiment 81.

Additional Embodiment 84. A device for separating cells derived from a tissue sample, the device comprising one or more of posts, obstructions, or obstacles such that cells having a size less than 12 μm flow in a first direction, while cells having a size greater than 12 μm flow in a second direction.

Additional Embodiment 85. A composition enriched with tumor nuclei, the tumor nuclei having a size greater than 8.5 μm, wherein the tumor nuclei were separated from normal nuclei without first staining either the tumor or normal nuclei.

Additional Embodiment 86. The composition of additional embodiment 85, wherein at least 50% of the composition comprises tumor nuclei.

Additional Embodiment 87. The composition of additional embodiment 85, wherein at least 65% of the composition comprises tumor nuclei.

Additional Embodiment 88. The composition of additional embodiment 85, wherein at least 80% of the composition comprises tumor nuclei.

Additional Embodiment 89. The composition of additional embodiment 85, wherein at least 95% of the composition comprises tumor nuclei.

Additional Embodiment 90. A kit comprising a first population of nuclei and a second population of nuclei, the first population of nuclei substantially enriched with tumor nuclei having a size greater than 8.5 μm, the second population of nuclei substantially enriched with normal nuclei having a size less than 8.5 μm, the first and second population of nuclei being derived from the same tumor sample, and wherein the tumor nuclei and normal nuclei are unstained.

Additional Embodiment 91. A method of testing for genetic abnormalities comprising performing a genomic analysis on each of the population of cells of additional embodiment 90.

Additional Embodiment 92. A device for separating nuclei derived from a tumor sample, the device comprising one or more of posts, obstructions, or obstacles such that nuclei having a size less than 8.5 μm flow in a first direction, while nuclei having a size greater than 8.5 μm flow in a second direction.

Further Embodiments

Further Embodiment 1. A method of segregating cellular particles from a tissue sample comprising: (i) homogenizing the tissue sample to provide a homogenized sample; and (ii) sorting cellular particles in the homogenized tissue sample by size into at least a first cellular particle population and a second cellular particle population.

Further Embodiment 2. The method of further embodiment 1, wherein the cellular particles include cells.

Further Embodiment 3. The method of any of the preceding further embodiments, wherein the cellular particles include cell nuclei.

Further Embodiment 4. The method of any of the preceding further embodiments, wherein the second cellular particle population comprises cellular particles derived from tumor cells.

Further Embodiment 5. The method of further embodiment 4, wherein the cellular particles derived from tumor cells have an average diameter ranging from between about 12 μm to about 50 μm or from between about 8.5 μm to about 30 μm.

Further Embodiment 6. The method of further embodiment 5, wherein the tumor cells are derived from at least one of a whole tumor, a partial tumor, a metastatic tumor, a partial metastatic tumor, or lymph nodes.

Further Embodiment 7. The method of any of the preceding further embodiments, wherein the tissue sample is derived from at least one of residual surgical material or a biopsy sample.

Further Embodiment 8. The method of any of the preceding further embodiments, wherein the tissue sample is one that was fixed in a crosslinking solution.

Further Embodiment 9. The method of any of the preceding further embodiments, wherein the tissue sample is derived from a sample embedded in paraffin.

Further Embodiment 10. The method of any the preceding further embodiments, wherein the homogenized tissue sample is further processed prior to sorting, wherein the further processing comprises at least one of digesting proteins within the homogenized sample, heating the sample, or filtering the homogenized sample.

Further Embodiment 11. The method of any of the preceding further embodiments, wherein the sorting of the cellular particles in the homogenized sampled by size does not require the step of staining the cellular particles.

Further Embodiment 12. The method of any the preceding further embodiments, wherein the cellular particles within the homogenized tissue sample are sorted with a microfluidic device.

Further Embodiment 13. The method of further embodiment 12, wherein the microfluidic device is a deterministic lateral displacement device.

Further Embodiment 14. The method of further embodiment 13, wherein cellular particles within the homogenized sample having a critical diameter of less than about 12 μm move with a convective flow of fluid passing through the deterministic lateral displacement device, while cells within the homogenized sample having a critical diameter of greater than about 12 μm move in a direction dictated by an arrangement of arrays.

Further Embodiment 15. The method of further embodiment 12, wherein the microfluidic device is a hydrophoretic filtration device.

Further Embodiment 16. The method of further embodiment 12, wherein the microfluidic device is a hydrodynamic filtration device.

Further Embodiment 17. The method of further embodiment 12, wherein the microfluidic device utilizes inertial focusing in curved channels.

Further Embodiment 18. The method of further embodiment 12, wherein the microfluidic device utilizes inertial focusing in straight channels.

Further Embodiment 19. The method of further embodiment 18, wherein inertial focusing in straight channels comprises one of a pinched flow fractionation process or a hydrodynamic spreading process.

Further Embodiment 20. The method of any of the preceding further embodiments, further comprising the step of assaying the cellular particles within the at least first or second populations for a first biomarker.

Further Embodiment 21. The method of further embodiment 20, wherein a presence of the first biomarker is indicative of cancer.

Further Embodiment 22. The method of further embodiment 20, wherein the first biomarker is an immune cell marker.

Further Embodiment 23. The method of any of the preceding further embodiments, wherein each of the first and second cellular particles populations are independently sequenced using next-generation sequencing.

Further Embodiment 24. The method of any of the preceding further embodiments, wherein each of the first and second cellular particles populations are independently analyzed using flow cytometry.

Further Embodiment 25. The method of any of the preceding further embodiments, wherein the first and second cellular particle populations provide matched tumor and normal samples for a patient.

Further Embodiment 26. The method of further embodiment 25, wherein the matched tumor and normal samples are analyzed to identify somatic mutations, copy number variations, or other genetic alterations.

Further Embodiment 27. The method of any of the preceding further embodiments, further comprising analyzing the first and second cellular particle populations for an RNA biomarker.

Further Embodiment 28. The method of any of further embodiments 1 to 26, further comprising analyzing the first and second cellular particle populations for a protein biomarker.

Further Embodiment 29. A method of segregating cells from a tissue sample comprising: homogenizing a tissue sample to provide a homogenized tissue sample;
sorting cells in the homogenized tissue sample by size, wherein the cells are sorted into at least a first cellular population enriched in cells having an average diameter of less than 12 μm and a second cellular population enriched in cells having an average diameter of greater than 12 µm, and wherein the cells within the homogenized tissue sample are sorted using a microfluidic device.

Further Embodiment 30. The method of further embodiment 29, wherein the microfluidic device is selected from the group consisting of a deterministic lateral displacement device, a hydrophoretic filtration device, a hydrodynamic filtration device, a microfluidic device utilizing inertial focusing in curved channels, and a microfluidic device utilizing inertial focusing in straight channels.

Further Embodiment 31. The method of any of further embodiments 29 to 30, wherein the microfluidic device does not require staining of the cells prior to sorting.

Further Embodiment 32. The method of any of further embodiments 29 to 31, further comprising analyzing at least one of the first or second cellular populations for one of an RNA biomarker or a protein biomarker.

Further Embodiment 33. The method of any of further embodiments 29 to 32, further comprising sequencing at least one of the first or second cellular populations.

Further Embodiment 34. The method of further embodiment 33, wherein an amount of genomic material available for sequencing in the first or second cellular populations is at least 0.05 micrograms.

Further Embodiment 35. The method of further embodiment 34, wherein the amount of genomic material is at least 0.1 micrograms.

Further Embodiment 36. The method of any of further embodiments 33 to 35, wherein at most four amplification cycles are conducted prior to sequencing.

Further Embodiment 37. The method of any of further embodiments 33 to 36, wherein the sequencing employs next-generation sequencing.

Further Embodiment 38. The method of any of further embodiments 29 to 37, wherein the first and second cellular populations provide matched tumor and normal samples for a patient.

Further Embodiment 39. The method of any of further embodiments 29 to 38, wherein the first cellular population is enriched in normal cells and the second cellular population is enriched in tumor cells.

Further Embodiment 40. A method of deriving at least an enriched population of tumor nuclei and an enriched population of normal nuclei from a tissue sample, comprising: dissociating the tumor and normal nuclei from the tissue sample; and sorting the tumor and normal nuclei by size with a microfluidic sorting device; wherein the normal nuclei within the enriched population of normal nuclei have an average nucleus size of less than 8.5 µm; and wherein the tumor nuclei within the enriched population of tumor nuclei have an average nucleus size of greater than 8.5 µm.

Further Embodiment 41. The method of further embodiment 40, wherein the microfluidic sorting device does not require a step of staining or biomarker analysis prior to sorting.

Further Embodiment 42. The method of further embodiment 40 or further embodiment 41, further comprising analyzing at least one of the enriched population of tumor nuclei or the enriched population or normal nuclei for one of an RNA biomarker or a protein biomarker.

Further Embodiment 43. The method of any of further embodiments 40 to 42, further comprising sequencing at least one of the enriched population of tumor nuclei or the enriched population or normal nuclei.

Further Embodiment 44. The method of further embodiment 43, wherein an amount of genomic material available for sequencing in the first or second cellular populations is at least 0.05 micrograms.

Further Embodiment 45. The method of further embodiment 44, wherein the amount of genomic material is at least 0.1 micrograms.

Further Embodiment 46. The method of any of further embodiments 40 to 45, further comprising analyzing at least one of the enriched population of tumor nuclei or the enriched population or normal nuclei using flow cytometry.

Further Embodiment 47. The method of any of further embodiments 40 to 46, wherein the tissue sample is derived from at least one of a whole tumor, a partial tumor, a metastatic tumor, a partial metastatic tumor, or lymph nodes.

Further Embodiment 48. The method of any of further embodiments 40 to 47, wherein the tissue sample is derived from at least one of residual surgical material or a biopsy sample.

Further Embodiment 49. The method of any of further embodiments 40 to 48, wherein the tissue sample is one that was fixed in a crosslinking solution.

Further Embodiment 50. The method of any of further embodiments 40 to 49, wherein the tissue sample is derived from a sample embedded in paraffin.

Further Embodiment 51. A method of segregating cellular particles from a tissue sample, comprising: (i) homogenizing a tissue sample to provide a homogenized sample; and (ii) sorting cellular particles within the homogenized tissue sample into at least a first population and a second population, wherein the cellular particles are sorted within a microfluidic device and wherein no staining is conducted prior to sorting.

Further Embodiment 52. The method of further embodiment 51, wherein the cellular particles are cells, and wherein the first population comprises normal cells and the second population comprises tumor cells.

Further Embodiment 53. The method of further embodiment 52, wherein the normal cells have an average diameter of less than 12 µm and the tumor cells have an average diameter of greater than 12 µm.

Further Embodiment 54. The method of further embodiment 51, wherein the cellular particles are nuclei, and wherein the first population comprises normal nuclei and the second population comprises tumor nuclei.

Further Embodiment 55. The method of further embodiment 53, wherein the normal nuclei have an average diameter of less than 8.5 µm and the tumor nuclei have an average diameter of greater than 8.5 µm.

Further Embodiment 56. A method of segregating cellular particles from a tissue sample, comprising: (i) homogenizing a tissue sample to provide a homogenized sample; and (ii) sorting cellular particles within the homogenized tissue sample into at least a first population and a second population, wherein the cellular particles are sorted within a microfluidic device and wherein staining is conducted prior to sorting.

Further Embodiment 57. The method of further embodiment 56, wherein the cellular particles are cells, and wherein the first population comprises normal cells and the second population comprises tumor cells.

Further Embodiment 58. The method of further embodiment 57, wherein the normal cells have an average diameter of less than 12 µm and the tumor cells have an average diameter of greater than 12 µm.

Further Embodiment 59. The method of further embodiment 56, wherein the cellular particles are nuclei, and wherein the first population comprises normal nuclei and the second population comprises tumor nuclei.

Further Embodiment 60. The method of further embodiment 59, wherein the normal nuclei have an average diameter of less than 8.5 μm and the tumor nuclei have an average diameter of greater than 8.5 μm.

The invention claimed is:

1. A method of segregating cellular particles from a representative sample comprising: (i) obtaining the representative sample, wherein the representative sample is derived from at least one fixed tissue specimen that has been homogenized, wherein any heterogeneity of cells within the at least one fixed tissue specimen is substantially uniformly distributed within the representative sample; and (ii) sorting cellular particles in at least a first aliquot of the representative sample by size into at least a first cellular particle population and a second cellular particle population, wherein the cellular particles are not tagged or labeled prior to or during the step of sorting.

2. The method of claim 1, wherein the cellular particles include cells.

3. The method of claim 1, wherein the cellular particles include cell nuclei.

4. The method of claim 1, wherein the second cellular particle population comprises cellular particles derived from tumor cells.

5. The method of claim 4, wherein the cellular particles derived from tumor cells have an average diameter ranging from between about 12 μm to about 50 μm or from between about 8.5 μm to about 30 μm.

6. The method of claim 5, wherein the tumor cells are derived from at least one of a whole tumor, a partial tumor, a metastatic tumor, a partial metastatic tumor, or lymph nodes.

7. The method of claim 1, wherein the representative sample is derived from at least one of fixed residual surgical material or a fixed biopsy sample.

8. The method of claim 1, wherein the representative sample is derived from a fixed tissue specimen embedded in paraffin.

9. The method of claim 1, wherein the cellular particles are sorted with a microfluidic device.

10. A method of segregating cells from a homogenized sample comprising:
(i) obtaining a homogenized sample, wherein the homogenized sample is derived from one or more fixed tissue specimens, and where any aliquot of the homogenized sample substantially uniformly expresses the heterogeneity of the one or more fixed tissue specimens; and
(ii) sorting untagged or unlabeled cells in the homogenized tissue sample by size, wherein the cells are sorted into at least a first cellular population enriched in cells having an average diameter of less than 12 μm and a second cellular population enriched in cells having an average diameter of greater than 12 μm, and wherein the cells within the homogenized sample are sorted using a microfluidic device.

11. The method of claim 10, wherein the microfluidic device is selected from the group consisting of a deterministic lateral displacement device, a hydrophoretic filtration device, a hydrodynamic filtration device, a microfluidic device utilizing inertial focusing in curved channels, and a microfluidic device utilizing inertial focusing in straight channels.

12. The method of claim 10, wherein the microfluidic device does not require staining of the cells prior to sorting.

13. The method of claim 10, further comprising analyzing at least one of the first or second cellular populations for one of an RNA biomarker or a protein biomarker.

14. The method of claim 10, further comprising sequencing at least one of the first or second cellular populations.

15. The method of claim 14, wherein an amount of genomic material available for sequencing in the first or second cellular populations is at least 0.05 micrograms.

16. The method of claim 15, wherein the amount of genomic material is at least 0.1 micrograms.

17. The method of claim 14, wherein at most four amplification cycles are conducted prior to sequencing.

18. The method of claim 14, wherein the sequencing employs next-generation sequencing.

19. The method of claim 10, wherein the first and second cellular populations provide matched tumor and normal samples for a patient.

20. The method of claim 10, wherein the first cellular population is enriched in normal cells and the second cellular population is enriched in tumor cells.

21. A method of segregating cellular particles from a sample comprising sorting cellular particles in the tissue sample by size into at least a first cellular particle population and a second cellular particle population, wherein the cellular particles are not tagged or labeled prior to or during the step of sorting; wherein the sample is derived from at least one fixed tissue specimen, and where any aliquot of the sample substantially homogeneously expresses the heterogeneity of the at least one fixed tissue specimen.

* * * * *